US012636351B2

(12) United States Patent
Maas et al.

(10) Patent No.: US 12,636,351 B2
(45) Date of Patent: May 26, 2026

(54) FUSION PROTEIN FOR TARGETED THROMBOLYSIS FOR TREATMENT OF MICROVASCULAR THROMBOSIS

(71) Applicant: TargED Biopharmaceuticals B.V., Utrecht (NL)

(72) Inventors: Coen Maas, Utrecht (NL); Steven De Maat, Utrecht (NL)

(73) Assignee: TargED Biopharmaceuticals B.V., Utrecht (NL)

( * ) Notice: Subject to any disclaimer, the term of this patent is extended or adjusted under 35 U.S.C. 154(b) by 0 days.

(21) Appl. No.: 18/829,591

(22) Filed: Sep. 10, 2024

(65) Prior Publication Data

US 2025/0249082 A1 Aug. 7, 2025

Related U.S. Application Data

(62) Division of application No. 17/041,459, filed as application No. PCT/EP2019/057731 on Mar. 27, 2019, now abandoned.

(30) Foreign Application Priority Data

Mar. 27, 2018 (EP) .................................... 18164232

(51) Int. Cl.
| | |
|---|---|
| *A61K 38/49* | (2006.01) |
| *A61K 38/17* | (2006.01) |
| *A61P 9/10* | (2006.01) |

(52) U.S. Cl.
CPC .......... *A61K 38/49* (2013.01); *A61K 38/1777* (2013.01); *A61P 9/10* (2018.01)

(58) Field of Classification Search
CPC .... A61K 38/49; A61K 38/1777; A61K 38/16; A61P 9/10; C07K 2317/92; C07K 2319/00; C07K 14/00; C07K 16/00; C07K 19/00
See application file for complete search history.

(56) References Cited

U.S. PATENT DOCUMENTS

2021/0023187 A1 1/2021 Maas et al.

FOREIGN PATENT DOCUMENTS

| WO | 2004/062551 A2 | 7/2004 |
|---|---|---|
| WO | 2006/094536 A1 | 9/2006 |

OTHER PUBLICATIONS

Witkowski et al., Biochemistry 38:11643-11650, 1999.*
Tang et al., Phil Trans R Soc B 368:20120318, 1-10, 2013.*

Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Alfano et al., Thromb Haemost 93:205-211; 2005.*
Absolute Antibody, "Antibody Structure," available online at absoluteantibody.com/antibody-resources/antibody-overview/ antibody-structure/, 4 pages (accessed on Feb. 27, 2024) (Year: 2024).
Berkowitz et al. "Epitope mapping of the van Willebrand factor subunit distinguishes fragments present in normal and type IIA van Willebrand disease from those generated by plasmin," The Journal of Clinical Investigation 79 (2):524-531 (1987).
Bode et al., "Platelet-Targeted Fibrinolysis Enhances Clot Lysis and Inhibits Platelet Aggregation," Circulation, American Heart Association, US 84(2):805-813 (1991).
Chana-Muñoz et al., "Origin and diversification of the plasminogen activation system among chordates," BMC Evolutionary Biology 19(27):1-17 (2019).
Ding et al., "Endothelial targeting of a recombinant construct fusing a PECAM-1 single-chain variable antibody fragment (scFv) with prourokinase facilitates prophylactic thrombolysis in the pulmonary vasculature," Blood 106 (13):4191-4198 (2005).
Drug Bank Online, "Plasminogen Activators", Drug Bank Online, available online at https://go.drugbank.com/categories/ DBCAT000074, 3 pages (accessed on Feb. 29, 2024) (Year: 2024).
George et al., "Syndromes of thrombotic microangiopathy," New England Journal of Medicine 371(7):654-666 (2014).
Tersteeg et al., "Plasm in cleavage of van Wille brand factor as an emergency bypass for ADAMTS13 deficiency in thrombotic microangiopathy," Circulation 129(12): 1320-1331 (2014).
Matsumoto et al. "anti-ADAMTS13 autoantibodies in patients with thrombotic thrombocytopenia purpura." Nihon Rinsho Men'eki Gakkai Kaishi= Japanese Journal of Clinical Immunology 36(2): 95-103 (2013).

* cited by examiner

*Primary Examiner* — Delia M Ramirez
(74) *Attorney, Agent, or Firm* — MEDLER FERRO WOODHOUSE & MILLS PLLC

(57) ABSTRACT

The present invention provides fusion proteins for targeted delivery of plasminogen activators to platelet-VWF complexes, or alternatively to the site where these are located, in a fibrin-independent manner. The fusion protein of the invention are for use in methods for the prevention or treatment of diseases or conditions associated with such platelet-VWF complexes, which may cause microvascular thrombosis in diseases such as e.g. thrombotic thrombocytopenic purpura. Preferred targeting agents for incorporation into the fusion proteins are e.g. nanobodies against VWF or platelets. Preferred plasminogen activators for use in the fusion proteins comprise the protease domains of uPA or tPA. The invention further pertains to nucleic acid molecule encoding the fusion proteins of the invention, e.g. a gene therapy vector, and to pharmaceutical compositions comprising the fusion proteins of the invention or such gene therapy vectors.

3 Claims, 10 Drawing Sheets

Specification includes a Sequence Listing.

FUSION PROTEIN FOR TARGETED THROMBOLYSIS FOR TREATMENT OF MICROVASCULAR THROMBOSIS

CROSS-REFERENCE TO RELATED INVENTIONS

This application is a divisional of U.S. application Ser. No. 17/041,459, filed Sep. 25, 2020 and abandoned after the filing of this application on Sep. 13, 2024, which is a U.S. National Phase Application under 35 USC § 371 of International Application No. PCT/EP2019/057731, filed Mar. 27, 2019, which claims priority to European Application No. 18164232.3, filed Mar. 27, 2018, each of which are hereby incorporated herein in their entirety.

SEQUENCE LISTINGS

The instant application includes a Sequence Listing which has been submitted electronically in XML ST26 format and is hereby incorporated by reference in its entirety. The Sequence Listing, created on Sep. 6, 2024, is named 0271-UM01US2_Sequence_Listing.xml and is 70.7 KB in size.

FIELD OF THE INVENTION

The present invention relates to the field of medicine and pharmacy, in particular to the field of biopharmaceuticals for use in the prevention or treatment of a disease or condition associated with microvascular thrombosis, such as e.g. thrombotic thrombocytopenic purpura. More specifically, the invention relates to fusion proteins comprising a targeting agent and a plasminogen activator, wherein the targeting agent targets the plasminogen activator to at least one of VWF, platelets and activated vascular endothelium with the aim to enzymatically degrade vascular obstructions in a fibrin-independent manner. The invention further relates to gene therapy vectors encoding such fusion proteins.

BACKGROUND ART

Microvascular thrombosis (MVT) is characterized by the formation of microvascular platelet aggregates. They are minimally composed of platelets and VWF. This becomes clear in thrombotic thrombocytopenic purpura (TTP), where platelet- and VWF-rich, but fibrin-poor microthrombi obstruct microvasculature with life-threatening consequences. Thus, fibrin, which is seen in macrovascular thrombosis, is not per se required for these microvascular obstructions. MVT is a shared feature between several disease states including thrombotic thrombocytopenic purpura, hemolytic uremic syndrome, antiphospholipid antibody syndrome and complement-mediated thrombotic microangiopathy (George et al., 2014, N Engl J Med. 371(7):654-66). In severe cases of MVT, multi-organ failure can occur with lethal consequences. Even in less severe cases, organ damage may form and reducing both the quality of life, as well as the life expectancy of the patient. Recent studies suggest that microvascular disease underlies cardiovascular disease/events in patients in the more generalized population with cardiovascular disease, and that do not show overt signs of macrovascular obstruction on radiological examination. This is ultimately thought to cause heart failure, in particular in females.

Patients with TTP experience attacks of microvascular thrombosis, when platelets form complexes with ultra-large multimers of von Willebrand Factor (VWF). This is the result of severely decreased activity of the enzyme ADAMTS13 (a disintegrin and metalloproteinase with a thrombospondin type I motif, member 13). ADAMTS13 normally regulates the thrombogenicity of VWF by enzymatically reducing its multimer size. Hereto, VWF needs to unfold from its globular form into an unrolled conformation, thereby exposing its A2 domain for proteolysis. The majority of TTP patients suffer from neutralizing autoantibodies against ADAMTS13. For a small subgroup, mutations in ADAMTS13 have been described that lead to deficiency (Upshaw-Shulman syndrome).

Current TTP therapy involves extensive plasma exchange to deplete inhibitory antibodies and restore ADAMTS13 activity at the same time. However, persistent autoantibodies impede elimination of microthrombi. This makes therapy time-consuming and very costly (Fijnheer et al., Ned Tijdsch Hematol 2016; 13 (1): 18-24).

Besides ADAMTS13, VWF can be cleaved by the enzyme plasmin (Berkowitz et al., J Clin Invest 1987 February; 79(2):524-31). We previously identified that systemic plasminogen activation (with streptokinase) was therapeutic in a mouse model for TTP, suggesting that plasmin can act as a functional alternative to ADAMTS13 (Tersteeg et al., 2014, Circulation, 129(12):1320-31). Although plasmin(ogen) can directly bind to unrolled VWF, natural plasminogen activators—such as tissue plasminogen activator (tPA) and urokinase plasminogen activator (uPA)—cannot. The natural targets of tPA and uPA are fibrin and the endothelial cell receptor uPAR, respectively. Furthermore, microthrombi in TTP are fibrin-poor and it is uncertain whether fibrin is a prerequisite for other types of MVT. This renders these molecules (i.e. tPA, uPA) that are generally used as thrombolytic agents in the treatment of macrovascular disease ineffective in treating MVT. Moreover, for safety reasons (i.e. low platelet counts) it is desirable to avoid systemic plasminogen activation.

It is an object of the present invention to provide for means and methods for treating MVT and associated conditions. The invention therefore provides fusion proteins for targeted delivery of plasminogen activators to platelet-VWF complexes, or alternatively to the site where these are located, in a fibrin-independent manner. The invention further provides therapeutic methods for conditions that can be prevented or treated by local delivery/stimulation of plasminogen activation to sites of microvascular occlusion.

SUMMARY OF THE INVENTION

In a first aspect, the invention relates to a fusion protein comprising a plasminogen activator and a targeting agent for targeting the plasminogen activator to a site of a thrombus comprising at least one of VWF and platelets. Preferably, the targeting agent in the fusion protein of the invention specifically binds to at least one of VWF, platelets, and activated or injured vascular endothelium. It is further preferred that the targeting agent in the fusion protein of the invention is not a targeting agent that specifically binds to only the activated form of the GPIIb/IIIa receptor on platelets. More preferably, the targeting agent in the fusion protein of the invention is one or more of: a) a targeting agent that at least binds unfolded VWF, wherein preferably the targeting agent preferentially binds unfolded VWF over globular VWF; b) a targeting agent that binds the D3 domain of VWF; c) a targeting agent that binds the GP1B receptor on platelets; d) a targeting agent that binds integrin $\alpha IIb/\beta III$ on platelets; e) a targeting agent that binds to a receptor that is preferentially expressed by activated endothelium, wherein preferably the receptor is selected form the group consisting of E-selectin, P-selectin, uPAR, c1q receptor, kinin B1 receptor, plasminogen receptor KT (PLGR-KT), endothelial protein C receptor, thrombomodulin, n-cadherin, ICAM-1 and VCAM-1; and, f) a targeting agent that binds to a membrane marker for activated or injured endothelium, wherein the membrane marker is one or more of anionic phospholipids, phosphatidylserine and phosphatidylethanolamine. In one embodiment, Preferably, the fusion protein of the invention comprises more than one targeting agent.

A fusion protein according to the invention preferably is a fusion protein wherein the targeting agent comprises at least one of: a) an antibody variable domain that specifically binds to at least one of VWF, platelets, and activated vascular endothelium; and, b) a binding domain from a protein that naturally binds VWF, platelets and activated or injured vascular endothelium, which binding domain specifically binds to at least one of VWF, platelets, and activated or injured vascular endothelium. Thus, in a fusion protein according to the invention, the antibody variable domain preferably is a VHH, more preferably a humanized VHH. Alternatively, in a fusion protein according to the invention, binding domain from a protein that naturally binds VWF, platelets and activated or injured vascular endothelium preferably comprises a binding domain selected from the group consisting of: i) the platelet GP1B receptor-binding A1 domain from VWF; ii) a VWF-binding domain from one of ADAMTS13, Factor XII, Factor H (complement regulator), plasminogen and Factor VIII; and, iii) a membrane binding domain selected from the vitamin K-dependent carboxylation/gamma-carboxyglutamic (GLA) domain, the C-domain from factor V and the C-domain from factor VIII.

In a fusion protein of the invention as defined above, the plasminogen activator preferably comprises the protease domain of tissue plasminogen activator (tPA), urokinase plasminogen activator (uPA), plasminogen, streptokinase or staphylokinase. It is preferred in a fusion protein of the invention that the plasminogen activator further comprises at least the cysteine-containing part of the connecting peptide that naturally occurs in the plasminogen activator immediately upstream of its protease domain. Optionally, a fusion protein of the invention comprises a linker amino acid sequence linking the targeting agent and the plasminogen activator.

Thus, a fusion protein in accordance with the invention preferably comprises in a N- to C-terminal order: a) one or more targeting agents as defined above, whereby, optionally the targeting agents are linked by linker amino acid sequences; b) optionally a linker amino acid sequence; and, c) a plasminogen activator or plasminogen-derived protease domain as defined above.

In a second aspect, the invention relates to a nucleic acid molecule comprising a nucleotide sequence encoding a fusion protein in accordance with the invention as defined above. Preferably, the nucleotide sequence encoding the fusion protein further comprises a nucleotide sequence encoding a signal peptide operably linked to the fusion protein. The nucleic acid molecule further preferably comprises regulatory elements conducive to the expression of the fusion protein, which regulatory elements are operably linked to the nucleotide sequence.

In a third aspect, the invention pertains to a gene therapy vector comprising a nucleic acid molecule according to the invention.

In a fourth aspect, the invention relates to a pharmaceutical composition comprising a fusion protein according to the invention or a gene therapy vector according to the invention and a pharmaceutically acceptable excipient.

In a fifth aspect, the invention pertains a fusion protein according to the invention, a gene therapy vector according to the invention or a pharmaceutical composition according to the invention, for use in the prevention or treatment of a disease or condition associated with thrombi comprising at least one of VWF and platelets, wherein preferably with the disease or condition associated with microvascular thrombosis. More preferably, the disease or condition associated with (micro)thrombi comprising at least one of VWF and platelets is selected from the group consisting of: acquired or hereditary thrombotic thrombocytopenic purpura (TTP) complement-mediated thrombotic microangiopathy, haemolytic uremic syndrome, antiphospholipid antibody syndrome, non-occlusive thrombus, the formation of an occlusive thrombus, arterial thrombus formation, acute coronary occlusion, peripheral arterial occlusive disease, restenosis and disorders arising from coronary by-pass graft, coronary artery valve replacement and coronary interventions such angioplasty, stenting or atherectomy, hyperplasia after angioplasty, atherectomy or arterial stenting, occlusive syndrome in a vascular system or lack of patency of diseased arteries, transient cerebral ischemic attack, unstable or stable angina pectoris, cerebral infarction, HELLP syndrome, carotid endarterectomy, carotid artery stenosis, critical limb ischemia, cardioembolism, peripheral vascular disease, restenosis, sickle cell disease and myocardial infarct.

In a sixth aspect, the invention pertains to a method for treating or reducing the risk of a disease or condition associated with thrombi comprising at least one of VWF and platelets, wherein the method comprises the step of administering to a subject in need thereof, an effective amount of fusion protein according to the invention, a gene therapy vector according to the invention or a pharmaceutical composition according to the invention, and wherein preferably with the disease or condition associated with microvascular thrombosis. More preferably, the disease or condition associated with (micro)thrombi comprising at least one of VWF and platelets is selected from the group consisting of: acquired or hereditary thrombotic thrombocytopenic purpura (TTP) complement-mediated thrombotic microangiopathy, haemolytic uremic syndrome, antiphospholipid antibody syndrome, non-occlusive thrombus, the formation of an occlusive thrombus, arterial thrombus formation, acute coronary occlusion, peripheral arterial occlusive disease, restenosis and disorders arising from coronary by-pass graft, coronary artery valve replacement and coronary interventions such angioplasty, stenting or atherectomy, hyperplasia after angioplasty, atherectomy or arterial stenting, occlusive syndrome in a vascular system or lack of patency of diseased arteries, transient cerebral ischemic attack, unstable or stable angina pectoris, cerebral infarction, HELLP syndrome, carotid endarterectomy, carotid artery stenosis, critical limb ischemia, cardioembolism, peripheral vascular disease, restenosis and myocardial infarct.

DESCRIPTION OF THE INVENTION

Definitions

The terms "homology", "sequence identity" and the like are used interchangeably herein. Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, CA 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred.

Alternatively percentage similarity or identity may be determined by searching against public databases, using algorithms such as FASTA, BLAST, etc. Thus, the nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to oxidoreductase nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information at www.ncbi.nlm.nih.gov/.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. Examples of classes of amino acid residues for conservative substitutions are given in the Tables below.

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes.

| | | | |
|---|---|---|---|
| 1 | A | S | T |
| 2 | D | E | |
| 3 | N | Q | |
| 4 | R | K | |
| 5 | I | L | M |
| 6 | F | Y | W |

Alternative Physical and Functional Classifications of Amino Acid Residues.

| | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P and T |
| Flexible residues | Q, T, K, S, G, P, D, E, and R |

Nucleotide sequences encoding fusion proteins of the invention may also be defined by their capability to hybridize with the nucleotide sequences of encoding fusion proteins as exemplified herein, under moderate, or preferably under stringent hybridization conditions. Stringent hybridization conditions are herein defined as conditions that allow a nucleic acid sequence of at least about 25, preferably about 50 nucleotides, 75 or 100 and most preferably of about 200 or more nucleotides, to hybridize at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridization is performed overnight, i.e. at least for 10 hours and preferably washing is performed for at least one hour with at least two changes of the washing solution.

These conditions will usually allow the specific hybridization of sequences having about 90% or more sequence identity.

Moderate conditions are herein defined as conditions that allow a nucleic acid sequences of at least 50 nucleotides, preferably of about 200 or more nucleotides, to hybridize at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridization is performed overnight, i.e. at least for 10 hours, and preferably washing is performed for at least one hour with at least two changes of the washing solution. These conditions will usually allow the specific hybridization of sequences having up to 50% sequence identity. The person skilled in the art will be able to modify these hybridization conditions in order to specifically identify sequences varying in identity between 50% and 90%.

A "nucleic acid construct" or "nucleic acid vector" is herein understood to mean a man-made nucleic acid molecule resulting from the use of recombinant DNA technology. The term "nucleic acid construct" therefore does not include naturally occurring nucleic acid molecules although a nucleic acid construct may comprise (parts of) naturally occurring nucleic acid molecules. The terms "expression vector" or expression construct" refer to nucleic acid molecules that are capable of effecting expression of a nucleotide sequence or gene in host cells or host organisms compatible with such expression vectors or constructs. These expression vectors typically include regulatory sequence elements that are operably linked to the nucleotide sequence to be expressed to effect its expression. Such regulatory elements usually at least include suitable transcription regulatory sequences and optionally, 3' transcription termination signals. Additional elements necessary or helpful in effecting expression may also be present, such as expression enhancer elements. The expression vector will be introduced into a suitable host cell and be able to effect expression of the coding sequence in an in vitro cell culture of the host cell. The expression vector will be suitable for replication in the host cell or organism of the invention whereas an expression construct will usually integrate in the host cell's genome for it to be maintained. Techniques for the introduction of nucleic acid into cells are well established in the art and any suitable technique may be employed, in accordance with the particular circumstances. For eukaryotic cells, suitable techniques may include calcium phosphate transfection, DEAE-Dextran, electroporation, liposome-mediated transfection and transduction using retrovirus or other virus, e.g. adenovirus, AAV, lentivirus or vaccinia. For microbial, e.g. bacterial, cells, suitable techniques may include calcium chloride transformation, electroporation and transfection using bacteriophage. The introduced nucleic acid may be on an extra-chromosomal vector within the cell or the nucleic acid may be integrated into the genome of the host cell. Integration may be promoted by inclusion of sequences within the nucleic acid or vector which promote recombination with the genome, in accordance with standard techniques. The introduction may be followed by expression of the nucleic acid to produce the encoded fusion protein. In some embodiments, host cells (which may include cells actually transformed although more likely the cells will be descendants of the transformed cells) may be cultured in vitro under conditions for expression of the nucleic acid, so that the encoded fusion protein polypeptide is produced, when an inducible promoter is used, expression may require the activation of the inducible promoter.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer.

The term "selectable marker" is a term familiar to one of ordinary skill in the art and is used herein to describe any genetic entity which, when expressed, can be used to select for a cell or cells containing the selectable marker. The term "reporter" may be used interchangeably with marker, although it is mainly used to refer to visible markers, such as green fluorescent protein (GFP). Selectable markers may be dominant or recessive or bidirectional.

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

The terms "protein" or "polypeptide" are used interchangeably and refer to molecules consisting of a chain of amino acids, without reference to a specific mode of action, size, 3-dimensional structure or origin.

The term "signal peptide" (sometimes referred to as signal sequence) is a short peptide (usually 16-30 amino acids long) present at the N-terminus of the majority of newly synthesized proteins that are destined towards the secretory pathway. At the end of the signal peptide there is usually a stretch of amino acids that is recognized and cleaved by signal peptidase either during or after completion of translocation (from the cytosol into the secretory pathway, i.e. ER) to generate a free signal peptide and a mature protein. Signal peptides are extremely heterogeneous and many prokaryotic and eukaryotic signal peptides are functionally interchangeable even between different species however the efficiency of protein secretion may depend on the signal peptide. Suitable signal peptides are generally known in the art e.g. from Kall et al. (2004 J. Mol. Biol. 338: 1027-1036) and von Heijne (1985, J Mol Biol. 184 (1): 99-105).

The term "gene" means a DNA fragment comprising a region (transcribed region), which is transcribed into an RNA molecule (e.g. an mRNA) in a cell, operably linked to suitable regulatory regions (e.g. a promoter). A gene will usually comprise several operably linked fragments, such as a promoter, a 5' leader sequence, a coding region and a 3' non-translated sequence (3' end) comprising a polyadenylation site. "Expression of a gene" refers to the process wherein a DNA region which is operably linked to appropriate regulatory regions, particularly a promoter, is transcribed into an RNA, which is biologically active, i.e. which is capable of being translated into a biologically active protein or peptide.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically (but not necessarily) be operably linked to another (heterologous) promoter sequence and, if applicable, another (heterologous) secretory signal sequence and/or terminator sequence than in its natural environment. It is understood that the regulatory sequences, signal sequences, terminator sequences, etc. may also be homologous to the host cell. When used to indicate the relatedness of two nucleic acid sequences the term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but has been obtained from another cell or synthetically or recombinantly produced. Generally, though not necessarily, such nucleic acids encode proteins that are not normally produced by the cell in which the DNA is transcribed or expressed. Similarly exogenous RNA encodes for proteins not normally expressed in the cell in which the exogenous RNA is present. Heterologous nucleic acids and proteins may also be referred to as foreign nucleic acids or proteins. Any nucleic acid or protein that one of skill in the art would recognize as heterologous or foreign to the cell in which it is expressed is herein encompassed by the term heterologous nucleic acid or protein. The term heterologous also applies to non-natural combinations of nucleic acid or amino acid sequences, i.e. combinations where at least two of the combined sequences are foreign with respect to each other.

Unless indicated otherwise, the terms "immunoglobulin" and "antibody" whether it used herein to refer to a heavy chain antibody or to a conventional 4-chain antibody is used as a general term to include both the full-size antibody, the individual chains thereof, as well as all parts, domains or fragments thereof (including but not limited to antigen-binding domains or fragments such as VHH domains or $V_H/V_L$ domains, respectively). In addition, the term "sequence" as used herein (for example in terms like "immunoglobulin sequence", "antibody sequence", "variable domain sequence", "VHH sequence" or "protein sequence"), should generally be understood to include both the relevant amino acid sequence as well as nucleic acid sequences or nucleotide sequences encoding the same, unless the context requires a more specific interpretation.

The "variable region" or "variable domain" of an antibody refers to the amino-terminal domains of the heavy or light chain of the antibody. The variable domain of the heavy chain may be referred to as "VH", or to "VHH" in case of a heavy chain antibody such as the camelid antibodies that consist of only heavy chains. The variable domain of the light chain may be referred to as "VL." These domains are generally the most variable parts of an antibody and contain the antigen-binding sites. The term "variable" refers to the fact that certain segments of the variable domains differ extensively in sequence among antibodies. The V domain mediates antigen binding and defines specificity of a particular antibody for its particular antigen. However, the variability is not evenly distributed across the average 110-amino acid span of the variable domains. Instead, the V regions consist of relatively invariant stretches called framework regions (FRs) of about 15-30 amino acids separated by shorter regions of extreme variability called "hypervariable regions" (HVRs) or complementarity determining regions (CDRs) that are each about 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, MD. (1991)).

The terms "VHH", "VHH domain" and "nanobody" are interchangeable herein and are used herein to refer to the variable domain of a heavy chain antibody, i.e. an antibody consisting only of heavy chains and devoid of light chains as are known e.g. from Camelids. The amino acid sequence and structure of a VHH can be considered without however being limited thereto to be comprised of four framework regions or "FR's", which are referred to in the art and herein below as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDRs", which are referred to in the art as "Complementarity Determining Region 1" or "CDR1"; as "Complementarity Determining Region 2" or "CDR2"; and as "Complementarity Determining Region 3" or "CDR3", respectively. The total number of amino acid residues in a VHH can be in the region of 110-120, is preferably 112-115, and is most preferably 113. It should however be noted that parts, fragments or analogs (as further described herein below) of a VHH are not particularly limited as to their length and/or size, as long as such parts, fragments or analogs meet the further functional requirements outlined herein below and are also preferably suitable for the purposes described herein.

The amino acid residues of a VHH (or conventional variable domain) are numbered according to the general numbering for $V_H$ domains given by Kabat et al. ("Sequence of proteins of immunological interest", US Public Health Services, NIH Bethesda, Md., Publication No. 91), as applied to VHH domains from Camelids by Riechmann and Muyldermans (1999, J. Immunol. Methods; 231: 25-38; see for example FIG. 2 of said reference). According to this numbering, FR1 of a VHH comprises the amino acid residues at positions 1-30, CDR1 of a VHH comprises the amino acid residues at positions 31-36, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113. In this respect, it should be noted that as is well known in the art for $V_H$ domains and for VHH domains the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDRs, position 1 according to the Kabat numbering corresponds to the start of FR1 and visa versa, position 36 according to the Kabat numbering corresponds to the start of FR2 and visa versa, position 66 according to the Kabat numbering corresponds to the start of FR3 and visa versa, and position 103 according to the Kabat numbering corresponds to the start of FR4.

Alternative methods for numbering the amino acid residues of $V_H$ domains, which methods can also be applied in an analogous manner to VHH domains from Camelids, are the method described by Chothia et al. (1989, Nature 342, 877-883), the so-called "AbM definition" and the so-called "contact definition". However, in the present description, claims and figures, the numbering according to Kabat as applied to VHH domains by Riechmann and Muyldermans will be followed, unless indicated otherwise.

For a general description of heavy chain antibodies and the variable VHH domains thereof, reference is inter alia made to the following references, which are mentioned as general background art: WO 94/04678, WO 95/04079, WO 96/34103, WO 94/25591, WO 99/37681, WO 00/40968, WO 00/43507, WO 00/65057, WO 01/40310, WO 01/44301, EP 1134231, WO 02/48193, WO 97/49805, WO 01/21817, WO 03/035694, WO 03/054016, WO 03/055527 WO 03/050531, WO 01/90190, WO 03/025020; WO 04/041867, WO 04/041862, WO 04/041865, WO 04/041863 and WO 04/062551 and Hassanzadeh-Ghassabeh et al. (2013, Nanomedicine, 8(6):1013-1026). For a more specific description of single domain VHH antibodies against Von Willebrand Factor or platelet receptor GPIb, reference is made to WO 2004/062551 and WO 2006/122825.

Generally, it should be noted that the term "VHH" (or nanobody) as used herein in its broadest sense is not limited to a specific biological source or to a specific method of preparation. For example, VHHs as used in the invention can be obtained (1) by isolating the VHH domain of a naturally occurring heavy chain antibody; (2) by expression of a nucleotide sequence encoding a naturally occurring VHH domain; (3) by "humanization" (as described below) of a naturally occurring VHH domain or by expression of a nucleic acid encoding a such humanized VHH domain; (4) by "camelization" of a naturally occurring VH domain from any animal species, in particular a species of mammal, such as from a human being, or by expression of a nucleic acid encoding such a camelized $V_H$ domain; (5) using synthetic or semi-synthetic techniques for preparing proteins, polypeptides or other amino acid sequences; (6) by preparing a nucleic acid encoding a VHH using techniques for nucleic acid synthesis, followed by expression of the nucleic acid thus obtained; and/or (7) by any combination of the foregoing. Suitable methods and techniques for performing the foregoing are state of the art and therefore known to the skilled person.

One particularly preferred class of VHHs for use in the invention comprises VHHs with an amino acid sequence that corresponds to the amino acid sequence of a naturally occurring VHH domain, but that has been "humanized", i.e. by replacing one or more amino acid residues in the amino acid sequence of said naturally occurring VHH sequence by one or more of the amino acid residues that occur at the corresponding position(s) in a $V_H$ domain from a conventional 4-chain antibody from a human being. This can be performed in a manner known per se, which will be clear to the skilled person, for example on the basis of the prior art on humanization including e.g. Jones et al. (Nature 321:522-525, 1986); Riechmann et al., (Nature 332:323-329, 1988); Presta (Curr. Op. Struct. Biol. 2:593-596, 1992), Vaswani and Hamilton (Ann. Allergy, Asthma and Immunol., 1:105-115 1998); Harris (Biochem. Soc. Transactions, 23:1035-1038, 1995); Hurle and Gross (Curr. Op. Biotech., 5:428-433, 1994), and specific prior art relating to humanization of VHHs such as e.g. Vincke et al. (2009, J. Biol. Chem. 284:3273-3284). Again, it should be noted that such humanized VHHs of the invention can be obtained in any suitable manner known per se and thus are not strictly limited to polypeptides that have been obtained using a polypeptide that comprises a naturally occurring VHH domain as a starting material.

A "blocking" antibody or an "antagonist" antibody is one which inhibits or reduces biological activity of the antigen it binds. Preferred blocking antibodies or antagonist antibodies substantially or completely inhibit the biological activity of the antigen. An "agonist antibody", as used herein, is an antibody which mimics at least one of the functional activities of a polypeptide of interest.

"Binding affinity" generally refers to the strength of the sum total of non-covalent interactions between a single binding site of a molecule (e.g., an antibody) and its binding partner (e.g., an antigen or target). Unless indicated otherwise, as used herein, "binding affinity" refers to intrinsic binding affinity which reflects a 1:1 interaction between members of a binding pair (e.g., antibody and antigen/target). The affinity of a molecule X for its partner Y can generally be represented by the dissociation constant ($K_d$). Affinity can be measured by common methods known in the art, including those described herein. Low-affinity antibodies generally bind antigen/target slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

A "$K_d$" or "$K_d$ value" can be measured by using an ELISA as described in the Examples herein or by using surface plasmon resonance assays using a BIAcore™-2000 or a BIAcore™-3000 (BIAcore, Inc., Piscataway, NJ) at 25° C. with immobilized antigen CM5 chips at ~10-50 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 μg/ml (~0.2 μM) before injection at a flow rate of 5 μl/minute to achieve approximately 10 response units (RU) of coupled protein. Following the injection of antigen, 1M ethanolamine is injected to block unreacted groups. For kinetics measurements, two-fold serial dilutions of the antibody or Fab (0.78 nM to 500 nM) are injected in PBS with 0.05% Tween 20 (PBST) at 25° C. at a flow rate of approximately 25 μl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant ($K_d$) is calculated as the ratio $k_{off}/k_{on}$. See, e.g., Chen, Y., et al., (1999) J. Mol Biol 293:865-881. If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stir red cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, NJ) as described above.

The phrases "pharmaceutical or pharmacologically acceptable" refers to molecular entities and compositions that do not produce or produce acceptable adverse, allergic or other untoward reaction when administered to an animal, such as, for example, a human, as appropriate. Whether certain adverse effects are acceptable is determined based on the severity of the disease. The preparation of a pharmaceutical composition that contains at least one chimeric polypeptide or additional active ingredient will be known to those of skill in the art in light of the present disclosure, as exemplified by Remington: The Science and Practice of Pharmacy" (Ed. Allen, L. V. 22nd edition, 2012, www.pharmpress.com), incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington: The Science and Practice of Pharmacy" (Ed. Allen, L. V. 22nd edition, 2012, www.pharmpress.com), incorporated herein by reference). Except insofar as any conventional carrier is incompatible with the active ingredient, its use in the therapeutic or pharmaceutical compositions is contemplated.

Any reference to nucleotide or amino acid sequences accessible in public sequence databases herein refers to the version of the sequence entry as available on the filing date of this document.

DESCRIPTION OF EMBODIMENTS

The present inventors have surprisingly found that targeting of plasminogen activation to sites of MVT is a feasible approach for the treatment of TTP. Patients with TTP experience attacks of MVT, when platelets form complexes with ultra-large VWF. We previously reported that systemic plasminogen activation (with streptokinase) was therapeutic in a mouse model for TTP, suggesting that plasmin can act as a functional alternative to ADAMTS13 (Tersteeg et al., 2014, supra). Although plasmin(ogen) can directly bind to VWF, natural plasminogen activators (tPA, uPA) cannot. Furthermore, microthrombi are fibrin-poor and for safety reasons it is desirable to avoid systemic plasminogen activation. To increase therapeutic efficacy and safety, the present invention therefore aims to stimulate cleavage of the thrombogenic multimeric protein VWF by plasmin. More specifically, the invention relates to modified plasminogen activators that have acquired the ability to bind either VWF, platelets or activated/injured (micro)vascular endothelial cells to locally induce plasmin activity for clearance of MVT, in a fibrin-independent manner. The invention further provides therapeutic methods for conditions that can be prevented or treated by local delivery/stimulation of plasminogen activation to sites of MVT.

In a first aspect the invention therefore pertains to a fusion protein comprising a plasminogen activator and a targeting agent for targeting the plasminogen activator to a site of a thrombus comprising at least one of VWF and platelets. The thrombus-site whereto the targeting agent targets the fusion protein of the invention can in principle be any site where a thrombus is present or developing, including sites of macrovascular as well as microvascular thrombi (MVT) and sites of (yet) non-occlusive macro- or microvascular thrombi. However, the fusion proteins of the invention are (also) aimed at clearing site of MVT, which are fibrin-poor, but which do contain VWF, platelets and where the vascular endothelium can be activated or injured. Preferably therefore, the targeting agent in the fusion protein of the invention is a targeting agent that specifically binds to at least one of VWF, platelets, and activated or injured vascular endothelium.

The targeting agent can be any ligand or binding molecule that specifically binds to at least one of VWF, platelets, and activated or injured vascular endothelium. Preferably, however, the targeting agent is a proteinaceous targeting agent. More preferably, the proteinaceous targeting agent is a part of the single amino acid chain of the fusion protein, which chain also comprises the plasminogen activator.

A targeting agent "which binds" a target of interest, e.g. VWF, platelets, or activated/injured endothelium, is an agent that binds the target with sufficient affinity such that the targeting agent is useful as a therapeutic agent in targeting a structure, e.g. an MVT, cell or tissue expressing or exposing the target, and does not significantly cross-react with other proteins or molecules. In such embodiments, the extent of binding of the targeting agent to a "non-target" molecule (e.g. protein) will be less than about 10% of the binding of the targeting agent to its particular target molecule as determined by fluorescence activated cell sorting (FACS) analysis or radioimmunoprecipitation (RIA). With regard to the binding of an targeting agent to a target molecule, the term "specific binding" or "specifically binds to" or "binds to" or is "specific for" a particular target molecule or polypeptide, e.g. an epitope on a particular polypeptide target, means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labelled target. In this case, specific binding is indicated if the binding of the labelled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a $K_d$ for the target (which may be determined as described above) of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a targeting agent binds to a particular target molecule, polypeptide or epitope on a particular polypeptide without substantially binding to any other molecule, polypeptide or epitope.

In one embodiment of the invention, the targeting agent in the fusion protein specifically binds to Von Willebrand factor (VWF), preferably to human VWF. The basic human VWF monomer is a 2050-amino acid protein. Every monomer contains a number of specific domains with a specific function including e.g. the D'/D3 domain, which binds to factor VIII, the A1 domain, which inter alia binds to the platelet GPIb-receptor, the A2 domain (which must partially unfold to expose the buried cleavage site for the specific ADAMTS13 protease that inactivates VWF by making much smaller multimers), the A3 domain, which binds to collagen, the C1 domain, in which the RGD motif binds to platelet integrin $\alpha$IIb$\beta$3 when this is activated and the "cysteine knot" domain (at the C-terminal end of the protein). Multimers of VWF can be extremely large, >20,000 kDa and can consist of over 80 subunits of 250 kDa each. VWF's primary function is binding to other proteins, in particular factor VIII, and it is important in platelet adhesion to wound sites. VWF is not an enzyme and, thus, has no catalytic activity. VWF binds to a number of cells and molecules, including e.g. to collagen (e.g. when is exposed in endothelial cells due to damage occurring to the blood vessel) and to the platelet GP1B receptor. The latter binding occurs under all circumstances, but is most efficient under high shear stress (i.e. rapid blood flow in narrow blood vessels). VWF binds to other platelet receptors when they are activated, e.g., by thrombin (i.e., when coagulation has been stimulated).

A targeting agent in the fusion protein of the invention can specifically bind to any and all forms, conformation, domains and epitopes of VWF. The targeting agent can thus specifically bind to at least one of the unfolded (activated) conformation of VWF and the globular (circulating unactivated) conformation of VWF (sVWF). In one embodiment, the targeting agent that at least binds unfolded VWF, wherein, preferably the targeting agent preferentially binds unfolded VWF over globular VWF (i.e. has a higher affinity for unfolded VWF than for globular VWF), more preferably, the targeting agent binds the unfolded (activated) conformation of VWF and does not bind to circulating unactivated globular forms of VWF. More specifically, the targeting agent in the fusion protein of the invention specifically binds to at least one of the VWF A1 domain, the A1 domain of activated VWF, VWF A2 domain, the A2 domain of activated VWF, the VWF A3 domain and the VWF D3 domain. Suitable examples of targeting agents that bind VWF are the VHH camelid antibody fragments used in the Examples herein, as further detailed below.

In another embodiment of the invention, the targeting agent in the fusion protein specifically binds to platelets (also referred to as thrombocytes), preferably to human platelets. Together with VWF, platelets are the main component of MVT and therefore also suitable targets for the targeting agent in the fusion protein of the invention. A targeting agent in the fusion protein of the invention can specifically bind to any and all forms of platelets. The targeting agent can thus specifically bind to at least one of activated platelets and to non-activated platelets. Preferably, targeting agent (at least) binds to non-activated platelets. Unlike macrovascular thrombosis or regular thrombosis, MVT do necessarily comprise activated platelets, and especially unactivated platelets (together with VWF) are causing the problems in MVT in e.g. TTP. Therefore, the targeting agent in the fusion protein preferably is not a targeting agent that specifically binds to only activated platelets (and not to non-activated platelets). More specifically, the targeting agent preferably is not a targeting agent that specifically binds to only the activated form of the GPIIb/IIIa receptor on platelets, such as e.g. the single-chain antibody SCE5 described by Schwarz et al. (2004, FASEB J. 18:1704-1706). The targeting agent thus preferably specifically binds to the non-active form of integrin $\alpha$IIb/$\beta$III. In a preferred embodiment, the targeting agent in the fusion protein of the invention specifically binds to at least one of: a) the platelet GP1B receptor, and b) integrin $\alpha$IIb/$\beta$III on platelets. A targeting agent that specifically binds to the platelet GP1B receptor is however preferred. Suitable targeting agents that bind platelets are known in the art, as e.g. exemplified by the anti-GPIb$\alpha$ antibody 6B4 described by Fontayne et al. (2006, Thromb Haemost. 96(5):671-84) or by the anti-GP1B the VHH antibody fragment used in the Examples herein.

In a further embodiment of the invention, the targeting agent in the fusion protein specifically binds to activated, injured and/or distressed endothelium (herein further collectively referred to as activated endothelium. The activated endothelium preferably is activated vascular endothelium, more preferably activated microvascular endothelium. The targeting agent can thus specifically bind to at least one of a receptor that is preferentially expressed by activated endothelium and a membrane marker for activated endothelium. Preferably, the receptor that is preferentially expressed by activated endothelium the receptor is selected form the group consisting of E-selectin, P-selectin, uPAR, c1q receptor, kinin B1 receptor, plasminogen receptor KT (PLGR-KT), endothelial protein C receptor, thrombomodulin, n-cadherin, ICAM-1 and VCAM-1. Preferably, the membrane marker for activated endothelium is one or more of anionic phospholipids, phosphatidylserine and phosphatidylethanolamine.

In one embodiment of a fusion protein of the invention, the targeting agent that specifically binds to one of the above-defined targets, preferably comprises at least one of: a) an antibody variable domain that specifically binds to one of said targets; and, b) a binding domain from a protein that naturally binds to one of said targets.

A preferred antibody variable domain that is present as targeting agent in a fusion protein of the invention is a VHH as defined herein above, more preferably the antibody variable domain is a humanized VHH.

In a preferred embodiment, the VHH that is present as targeting agent in a fusion protein of the invention is a VHH that specifically binds VWF. Suitable examples of VHHs that bind VWF and that are part of a fusion protein of the invention as targeting agent in are the VWF-binding VHHs that are part of the fusion protein in the Examples herein or that are described in US2013/0136736-A1, which is incorporated by reference herein.

A preferred VHH that binds soluble globular VWF and that is present as targeting agent in a fusion protein of the invention is VHH-sVWF, having the amino acid sequence of positions 55-178 of SEQ ID NO:7 or a VHH having an amino acid sequence with at least 80, 85, 90, 91, 92, 93, 94, 95, 96, 97, 98 or 99% sequence identity with positions 55-178 of SEQ ID NO:7 and having a $K_d$ for VWF of less than 1, 0.5, 0.2, 0.1, 0.05 or 0.0306 nM.

A preferred VHH that binds the D3 domain of VWF and that is present as targeting agent in a fusion protein of the invention is VHH-D3, having the amino acid sequence of positions 55-178 of SEQ ID NO:8 or a VHH having an amino acid sequence with at least 80, 85, 90, 91, 92, 93, 94, 95, 96, 97, 98 or 99% sequence identity with positions 55-178 of SEQ ID NO:8 and having a $K_d$ for VWF of less than 1, 0.5, 0.4, 0.35, or 0.33 nM.

A preferred VHH that binds the A1 domain of VWF and that is present as targeting agent in a fusion protein of the invention is VHH-A12, having the amino acid sequence of positions 55-179 of SEQ ID NO:11 or a VHH having an amino acid sequence with at least 80, 85, 90, 91, 92, 93, 94, 95, 96, 97, 98 or 99% sequence identity with positions 55-179 of SEQ ID NO:11 and having a $K_d$ for VWF of less than 25, 20, 18, 15 or 13 nM. Another preferred of VHH that binds the A1 domain of VWF and that is present as targeting agent in a fusion protein of the invention is the VHH having the amino acid sequence of SEQ ID NO:13 or its humanized version having the amino acid sequence of SEQ ID NO:14, or a VHH having an amino acid sequence with at least 80, 85, 90, 91, 92, 93, 94, 95, 96, 97, 98 or 99% sequence identity with the SEQ ID NO:13 or 14 and having a $K_d$ for VWF of less than 10, 5 or 2 nM.

A preferred VHH that binds the platelet GP1B receptor and that is present as targeting agent in a fusion protein of the invention is VHH-GP1B17, having the amino acid sequence of positions 55-178 of SEQ ID NO:12 or a VHH having an amino acid sequence with at least 80, 85, 90, 91, 92, 93, 94, 95, 96, 97, 98 or 99% sequence identity with positions 55-178 of SEQ ID NO:12 and having a $K_d$ for the platelet GP1B receptor of less than 20, 15, 10, 5, 2, 1, 0.5, 0.2 or 0.1 nM. Other preferred VHHs that bind the platelet GP1B receptor and that are present as targeting agent in fusion proteins of the invention have an amino acid sequence selected from the group consisting of amino acid sequences of positions 55-175 of SEQ ID NO:20, positions 55-178 of SEQ ID NO:21, positions 55-172 of SEQ ID NO:22, positions 55-171 of SEQ ID NO:23, positions 55-174 of SEQ ID NO:24, positions 55-176 of SEQ ID NO:25; positions 55-178 of SEQ ID NO:26, positions 55-178 of SEQ ID NO:27, positions 55-178 of SEQ ID NO:28, positions 55-166 of SEQ ID NO:29, positions 55-180 of SEQ ID NO:30, positions 55-176 of SEQ ID NO:31, positions 55-176 of SEQ ID NO:32, positions 55-179 of SEQ ID NO:33, positions 55-179 of SEQ ID NO:34, positions 55-177 of SEQ ID NO:35, positions 55-178 of SEQ ID NO:36 and positions 55-181 of SEQ ID NO:37, or have an amino acid sequence with at least 80, 85, 90, 91, 92, 93, 94, 95, 96, 97, 98 or 99% sequence identity with the amino acid sequence in this group and having a $K_d$ for the platelet GP1B receptor of less than 20, 15, 10, 5, 2, 1, 0.5, 0.2 or 0.1 nM.

Another preferred VHH that binds the A1 domain of VWF comprises an amino acid sequence with at least 80, 85, 90, 91, 92, 93, 94, 95, 96, 97, 98 or 99% sequence identity with SEQ ID NO: 46. Preferably a VHH that binds the A1 domain of VWF and that comprises the amino acid sequence of SEQ ID NO:46 is present as targeting agent in a fusion protein of the invention is the VHH having the amino acid sequence of SEQ ID NO:45 or its humanized version having the amino acid sequence of SEQ ID NO:44, or a VHH having an amino acid sequence with at least 80, 85, 90, 91, 92, 93, 94, 95, 96, 97, 98 or 99% sequence identity with the SEQ ID NO:44 or 45 and having a Kd for VWF of less than 10, 5 or 2 nM.

In another embodiment of a fusion protein of the invention, the targeting agent that specifically binds to at least one of VWF, platelets, and activated or injured vascular endothelium comprises a binding domain from a protein that naturally binds to at least one of VWF, platelets, and activated or injured vascular endothelium. Preferably, the binding domain comprises a binding domain selected from the group consisting of: i) the A1 domain from VWF, or at least a part of the VWF A1 domain that binds the platelet GP1B receptor; ii) a VWF-binding domain from one of ADAMTS13, Factor XII, Factor H (complement regulator), plasminogen and Factor VIII, at least a part of these domains that binds VWF; and, iii) a domain that binds to membrane (s) of activated or injured vascular endothelium, which domain is selected from the vitamin K-dependent carboxylation/gamma-carboxyglutamic (GLA) domain, the C-domain from factor V and the C-domain from factor VIII.

In one embodiment of the invention, the fusion protein comprises more than one targeting agent. The fusion protein can thus comprises e.g. two, three, four, five, six or more targeting agents. If more than one targeting agent is present in the fusion protein, there can be more than one copy of the same targeting agent present in the fusion protein. Alternatively, the fusion protein can comprises at least two different targeting agents. For example, the fusion protein can comprise at least two different targeting agents that (each) bind to at least two different domains of VWF or to at least two different receptors on platelets. Or the fusion protein can comprises at least two different targeting agents, of which at least one binds to VWF and at least one other binds to platelets. An advantage of incorporating more than one targeting agent in the fusion protein is the avidity of the multivalent binding at the site of MVT, i.e. the accumulated strength of multiple affinities of individual binding interactions by the individual targeting agents. When more than one targeting agent is present in the fusion protein, the individual targeting agents are preferably arranged in tandem, and preferably with suitable (flexible) spacer- or linker-amino acid sequences between the individual targeting agents.

Suitable flexible linker-amino acid sequences are known in the art (e.g. from Chen et al., 2013, Adv Drug Deliv Rev. 65(10): 1357-1369). Flexible linkers are usually applied when the joined domains require a certain degree of movement or interaction. They are generally composed of small, non-polar (e.g. Gly) or polar (e.g. Ser or Thr) amino acids. The small size of these amino acids provides flexibility, and allows for mobility of the connecting functional domains. The incorporation of Ser or Thr can maintain the stability of the linker in aqueous solutions by forming hydrogen bonds with the water molecules, and therefore reduces the unfavorable interaction between the linker and the protein moieties. Preferred flexible linkers have sequences consisting primarily of stretches of Gly and Ser residues ("GS" linker). An example of preferred (and widely used) flexible linker has the sequence of $(Gly-Gly-Gly-Gly-Ser)_n$. By adjusting the copy number "n", the length of this GS linker can be optimized to achieve appropriate separation of the functional domains, or to maintain necessary inter-domain interactions. Besides the GS linkers, many other flexible linkers have been designed for recombinant fusion proteins. These flexible linkers are also rich in small or polar amino acids such as Gly and Ser, but can contain additional amino acids such as Thr and Ala to maintain flexibility, as well as polar amino acids such as Lys and Glu to improve solubility, such as e.g. the flexible linkers KESGSVSSEQLAQFRSLD (SEQ ID NO:38) and EGKSSGSGSESKST (SEQ ID NO:38), that have been applied for the construction of a bioactive scFv's.

In addition to the above described one or more targeting agents for targeting to an MVT, a fusion protein of the invention further at least comprises a plasminogen activator. Plasminogen activators are serine proteases that catalyze the activation of plasmin via proteolytic cleavage of its zymogen form plasminogen. While plasmin is an important factor in fibrinolysis, in the context of the present invention plasminogen activation is relied upon for its fibrin-independent thrombolytic activity towards MVT. Therefore, a fusion protein according to the invention comprises a plasminogen activator, which plasminogen activation preferably comprises a (catalytic) protease domain from tissue plasminogen activator (tPA), urokinase plasminogen activator (uPA), plasminogen, streptokinase or staphylokinase. The catalytic protease domains of tPA, uPA, plasminogen, streptokinase and staphylokinase are well known in the art. A preferred plasminogen-activating catalytic protease domain for incorporation in a fusion protein of the invention is the catalytic protease domain of uPA, preferably of human uPA, which comprises the amino acid sequence of positions 16-268 of SEQ ID NO:1, or the catalytic protease domain of tPA, preferably of human tPA, which comprises the amino acid sequence of positions 15-266 of SEQ ID NO:19.

In one embodiment, wherein the catalytic domain protease domain for incorporation in a fusion protein of the invention is the catalytic protease domain of uPA, preferably of human uPA, the (human) uPA domain comprises a mutation in its sequence that stabilizes the (human) uPA. Stabilizing mutations have been described in U.S. Pat. No. 5,472,692 and Sun et al (J Biol Chem 1997 Sep. 19; 272 (38): 23818-23823) which incorporated herein in their entirety. In one preferred embodiment, the catalytic domain protease comprises and/or consists of SEQ ID NO: 1 wherein the Lysin (K) located at position 157 of SEQ ID NO:1 is mutated to Histidine (H). In one preferred embodiment, the catalytic domain protease comprises and/or consists of SEQ ID NO: 2 wherein the Lysin (K) located at position 158 of SEQ ID NO:2 is mutated to Histidine (H).

In one embodiment, the plasminogen activator that is incorporated in a fusion protein of the invention is comprises a variant of a catalytic protease domain with reduced susceptibility to natural inhibitors of plasminogen activators, such as plasminogen activator inhibitor-1 (PAI-1). Such variants include e.g. variants of the protease domains of uPA or tPA with one or more modifications in their exosite loops that are involved in the interaction with PAI-1, such as e.g. the 37- and 147-loops in the protease domains of uPA or analogous loops in the protease domain of tPA, e.g. the 37-, 60-, 97-, 147- and 217-loops (see Lin et al. J Biol Chem. 2011 Mar. 4; 286(9): 7027-7032). Examples of such modifications are deletions of exosites that are specific to interaction with PAI-1 (tPA del 296-302) or replacement of specific amino acids that specifically mediate the interaction with PAI-1 (tPA Arg→Glu 304 or Arg→Ser 304) (Madison et al. Nature. 1989 Jun. 29; 339(6227):721-4).

In a preferred embodiment the plasminogen activator that is incorporated in a fusion protein of the invention further comprises at least the cysteine-containing part of the connecting peptide that naturally occurs in the plasminogen activator immediately upstream (N-terminally) of its protease domain. The presence of the connecting peptide including its cysteine avoids that the counterpart cysteine in the protease domain forms unwanted disulfide bridges.

A preferred connecting peptides for inclusion in the plasminogen activator that is incorporated in a fusion protein of the invention is: a) a connecting peptide from uPA that at least includes amino acids 17-27 of SEQ ID NO:16, more preferably the connecting peptide at least includes amino acids 13-27 of SEQ ID NO:16; b) a connecting peptide from tPA that at least includes amino acids 3-14 of SEQ ID NO:17, more preferably the connecting peptide at least includes amino acids 1-14 of SEQ ID NO:17; or c) a connecting peptide from plasminogen that at least includes amino acids 5-18 of SEQ ID NO:18, more preferably the connecting peptide at least includes amino acids 1-18 of SEQ ID NO:18.

In another preferred embodiment, a fusion protein of the invention preferably comprises a linker-amino acid sequence located between the one or more targeting agents on the one hand, and the plasminogen activator on the other hand. It is thereby understood that if the plasminogen activator includes a connecting peptide e.g. as described above, that the linker-amino acid sequence then is located upstream of the plasminogen activator's connecting peptide. The linker-amino acid sequence linking the targeting agents and the plasminogen activator preferably is a flexible linker-amino acid sequence as described above. A preferred linker-amino acid sequence for linking the targeting agents and the plasminogen activator has the sequence of (Gly-Gly-Gly-Gly-Ser)$_n$, whereby n is 1-4, more preferably 2 or 3 and most preferably 2. A particularly preferred linker-amino acid sequence has the amino acid sequence of SEQ ID NO:6.

Thus, a preferred fusion protein in accordance with the invention is a fusion protein that comprises in a N- to C-terminal order: a) one or more targeting agents as defined hereinabove, whereby, optionally the targeting agents are linked by linker amino acid sequences as defined hereinabove; b) optionally a linker amino acid sequence as defined hereinabove; and, c) a plasminogen activator as defined hereinabove. The fusion protein can further comprise additional functional elements, including e.g. isolation tags, such as e.g. a His-tag or a STREP isolation tag, or a cleavage site recognized only by a specific protease such as e.g. a Tobacco Etch Virus cleavage site, so to be able to cleave off undesirable amino acid sequences (e.g. the isolation tag) from the fusion protein. An example of the configuration of a preferred fusion protein in accordance with the invention is shown in FIG. 1, whereby the nucleotide sequence encoding the fusion protein also encodes a (Igκ) signal sequence upstream of the fusion protein to direct its secretion from the cell in which the protein is produced.

In a second aspect, the invention relates to a nucleic acid molecule comprising a nucleotide sequence encoding a fusion protein of the invention as defined hereinabove. The nucleotide sequence encoding the fusion protein further preferably comprises a nucleotide sequence encoding a signal peptide operably linked to the fusion protein. A preferred signal peptide for directing secretion of the fusion proteins of the invention is the Igκ signal peptide, having the amino acid sequence of SEQ ID NO: 3. A nucleic acid molecule comprising a nucleotide sequence encoding a fusion protein of the invention, further preferably comprises regulatory elements conducive to the expression of the fusion protein in an appropriate host cell, which regulatory elements are operably linked to the nucleotide sequence.

In a third aspect, the invention relates to a vector comprising a nucleic acid molecule according to the invention. Optionally, the vector according to the invention is a gene therapy vector.

Preferably, the a gene therapy vector is a viral gene therapy vector, e.g. a viral gene therapy vector selected from gene therapy vectors based on an adenovirus, an adeno-associated virus (AAV), a herpes virus, a pox virus, an oncolytic virus vector and a retrovirus. A preferred viral gene therapy vector is an AAV or Lentiviral vector.

In a fourth aspect, the invention relates to a host cell comprising a vector according to the invention, which host cell expresses a fusion protein according to invention.

The cell preferably is an isolated cell or a cultured cell. Among the host cells that may be employed are prokaryotes, yeast or higher eukaryotic cells. Prokaryotes include gram negative or gram positive organisms, for example *Escherichia coli* or bacilli. Higher eukaryotic cells include insect cells and established cell lines of mammalian origin. Examples of suitable mammalian host cell lines include the COS-7 line of monkey kidney cells (Gluzman et al., 1981, Cell 23:175), L cells, HEK 293 cells, C127 cells, 3T3 cells, Chinese hamster ovary (CHO) cells, HeLa cells, BHK cell lines, and the CVI/EBNA cell line derived from the African green monkey kidney cell line CVI as described by McMahan et al., 1991, EMBO J. 10: 2821. Appropriate cloning and expression vectors for use with bacterial, fungal, yeast, and mammalian cellular hosts are described by Pouwels et al. (Cloning Vectors: A Laboratory Manual, Elsevier, New York, 1985).

The transformed cells can be cultured under conditions that promote which host cell expresses a fusion protein according to invention. Thus in one aspect the invention relates to a method for producing a fusion protein according to invention, the method comprising the step of cultivating a cell comprising at least one expression vector as defined herein, under conditions conducive to expression of a fusion protein according to invention, optionally, recovering the fusion protein according to invention.

A fusion protein according to invention can be recovered by conventional protein purification procedures, including e.g. protein A-Sepharose, hydroxylapatite chromatography, gel electrophoresis, dialysis, or affinity chromatography, using e.g. strepavidin/biotin (see e.g. Low et al., 2007, J. Chromatography B, 848:48-63; Shukla et al., 2007, J. Chromatography B, 848:28-39).

In a fifth aspect, the invention relates to a pharmaceutical composition comprising and/or consisting of a fusion protein according to the invention, a nucleic acid according to the invention, a vector or gene therapy vector according to the invention, or a host cell according to the invention and a pharmaceutically acceptable excipient.

The pharmaceutical composition further preferably comprises at least one pharmaceutically acceptable carrier. The pharmaceutically acceptable carrier such as an adjuvant, or vehicle, is for administration of the antibody or antibody fragment to a subject. Said pharmaceutical composition can be used in the methods of treatment described herein below by administration of an effective amount of the composition to a subject in need thereof. The term "subject", as used herein, refers to all animals classified as mammals and includes, but is not restricted to, primates and humans. The subject is preferably a male or female human of any age or race.

The term "pharmaceutically acceptable carrier", as used herein, is intended to include any and all solvents, dispersion media, coatings, antibacterial and antifungal agents, isotonic and absorption delaying agents, and the like, compatible with pharmaceutical administration (see e.g. "Handbook of Pharmaceutical Excipients", Rowe et al eds. 7$^{th}$ edition, 2012, www.pharmpress.com). The use of such media and agents for pharmaceutically active substances is well known in the art. Except insofar as any conventional media or agent is incompatible with the active compound, use thereof in the compositions is contemplated. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter ions such as sodium; metal complexes (e.g. $Zn^{2+}$-protein complexes); and/or non-ionic surfactants such as TWEEN™, PLURONICS™ or polyethylene glycol (PEG).

Supplementary active compounds can also be incorporated into the pharmaceutical composition of the invention. Thus, in a particular embodiment, the pharmaceutical composition of the invention may also contain more than one active compound as necessary for the particular indication being treated, preferably those with complementary activities that do not adversely affect each other. For example, it may be desirable to further provide a chemotherapeutic agent, a cytokine, an analgesic agent, a thrombolytic or an immunomodulating agent, e.g. an immunosuppressive agent or an immunostimulating agent. The effective amount of such other active agents depends, among other things, on the amount of antibody of the invention present in the pharmaceutical composition, the type of disease or disorder or treatment, etc.

In an embodiment, the fusion protein according to the invention is prepared with carriers that will protect said compound against rapid elimination from the body, such as a controlled release formulation, including implants and microencapsulated delivery systems, e.g. liposomes. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions, including targeted liposomes can also be used as pharmaceutically acceptable carriers. These can be prepared according to methods known to those skilled in the art, for example, as described in U.S. Pat. No. 4,522,811 or WO2010/095940.

The administration route of the fusion protein according to the invention can be parenteral. The term "parenteral" as used herein includes intravenous, intra-arterial, intralymphatic, intraperitoneal, intramuscular, subcutaneous, rectal or vaginal administration. The intravenous forms of parenteral administration are preferred. By "systemic administration" is meant oral, intravenous, intraperitoneal and intramuscular administration. The amount of the fusion protein required for therapeutic or prophylactic effect will, of course, vary with the fusion protein chosen, the nature and severity of the condition being treated and the patient. In addition, the fusion protein may suitably be administered by pulse infusion, e.g., with declining doses of the fusion protein. Preferably the dosing is given by injections, most preferably intravenous or subcutaneous injections, depending in part on whether the administration is brief or chronic.

Thus, in a particular embodiment, the pharmaceutical composition of the invention may be in a form suitable for parenteral administration, such as sterile solutions, suspensions or lyophilized products in the appropriate unit dosage form. Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, CremophorEM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol or sodium chloride in the composition.

Prolonged absorption of the injectable compositions can be brought about by including in the composition an agent which delays absorption, for example, aluminium monostearate and gelatin.

Sterile injectable solutions can be prepared by incorporating the active compound (e.g a fusion protein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In a particular embodiment, said pharmaceutical composition is administered via intravenous (IV) or subcutaneous (SC). Adequate excipients can be used, such as bulking agents, buffering agents or surfactants. The mentioned formulations will be prepared using standard methods for preparing parenterally administrable compositions as are well known in the art and described in more detail in various sources, including, for example, "Remington: The Science and Practice of Pharmacy" (Ed. Allen, L. V. 22nd edition, 2012, www.pharmpress.com).

It is especially advantageous to formulate the pharmaceutical compositions, namely parenteral compositions, in dosage unit form for ease administration and uniformity of dosage. Dosage unit form as used herein refers to physically discrete units suited as unitary dosages for the subject to be treated; each unit containing a predetermined quantity of active compound (antibody of the invention) calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Generally, for the prevention and/or treatment of the diseases and disorders mentioned herein and depending on the specific disease or condition to be treated and its severity, the potency of the specific fusion protein of the invention to be used, the specific route of administration and the specific pharmaceutical formulation or composition used, the fusion proteins of the invention will generally be administered in the range of from 0.001 to 1,000 mg/kg body weight/day, preferably about 0.01 to about 100 mg/kg body weight/day, most preferably from about 0.05 to 10 mg/kg body weight/day, such as about 1, 10, 100 or 1000 microgram per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment.

Aside from administration of a fusion protein according to the invention to the patient, the present application contemplates administration of a fusion proteins by gene therapy.

The pharmaceutical compositions can be included in a container, pack, or dispenser together with instructions for administration.

The fusion proteins and pharmaceutical compositions of this invention may be used with other drugs to provide a combination therapy. The other drugs may form part of the same composition, or be provided as a separate composition for administration at the same time or at different time.

In a sixth aspect, the invention pertains to at least one of a fusion protein, a gene therapy vector and a pharmaceutical composition, each as defined hereinabove, for use in the treatment or prevention of a disease or condition associated with thrombosis. The disease or condition to be prevented or treated can be any disease or condition associated with or involving thrombi comprising at least one of VWF and platelets. Such a disease or condition associated with thrombi comprising at least one of VWF and platelets can be any disease or condition involving macrovascular and/or microvascular thrombi (MVT), and/or involving sites of (yet) non-occlusive macro- or microvascular thrombi. Preferably, however, the disease or condition to be prevented or treated is a disease or condition associated with at least microvascular thrombosis (MVT). It is to be understood herein that the term "to prevent a disease or condition" includes and/or can be equal to reducing the risk of that disease or condition to occur or develop.

In a preferred embodiment the disease or condition associated with thrombi comprising at least one of VWF and platelets is a disease or condition is selected from the group consisting of: acquired or hereditary thrombotic thrombocytopenic purpura (TTP) complement-mediated thrombotic microangiopathy (as reviewed by George et al., 2014, N Engl J Med. 371(7):654-66) haemolytic uremic syndrome, antiphospholipid antibody syndrome, the formation of an occlusive thrombus, arterial thrombus formation, acute coronary occlusion, peripheral arterial occlusive disease, restenosis and disorders arising from coronary by-pass graft, coronary artery valve replacement and coronary interventions such angioplasty, stenting or atherectomy, hyperplasia after angioplasty, atherectomy or arterial stenting, occlusive syndrome in a vascular system or lack of patency of diseased arteries, transient cerebral ischemic attack, unstable or stable angina pectoris, cerebral infarction, HELLP syndrome (HELLP is Hemolysis, Elevated Liver enzymes, and Low Platelet count), carotid endarterectomy, carotid artery stenosis, critical limb ischemia, cardioembolism, peripheral vascular disease, restenosis, sickle cell disease and myocardial infarct.

Further diseases or conditions associated with thrombi comprising at least one of VWF and platelets to be treated or prevented in accordance with a method of the invention are diseases or conditions is selected from the group consisting of unstable angina, stable angina, angina pectoris, embolus formation, deep vein thrombosis, hemolytic anemia, acute renal failure, thrombolytic complications, disseminated intravascular coagulopathy (DIC), thrombosis, coronary heart disease, thromboembolic complications, myocardial infarction, restenosis, and atrial thrombosis formation in atrial fibrillation, chronic unstable angina, transient ischemic attacks and strokes, peripheral vascular disease, arterial thrombosis, pre-eclampsia, embolism, restenosis and/or thrombosis following angioplasty, anastomosis of vascular grafts, and chronic exposure to cardiovascular devices. Such conditions may also result from thromboembolism and reocclusion during and after thrombolytic therapy, after angioplasty, and after coronary artery bypass.

In a further embodiment a fusion protein, a gene therapy vector and a pharmaceutical composition, each as defined hereinabove, for use in the treatment or prevention of a plaque or thrombus in an individual. Said plaque or thrombus formation may be under conditions of high shear. In both thrombosis and reocclusion, the reversible adhesion or tethering of the platelets at high shear rate is followed by a firm adhesion through the collagen receptor on platelets resulting in platelet activation; the tethering of platelets by VWF to collagen exposed in the damaged vessel wall is especially important under high shear conditions. A fusion protein of the present invention performs well under high shear conditions.

In a seventh aspect the invention relates to method for treating or reducing the risk of a disease or condition associated with thrombi comprising at least one of VWF and platelets, wherein the method comprises the step of administering to a subject in need thereof, an effective amount of fusion protein as defined hereinabove, a gene therapy vector as defined hereinabove or a pharmaceutical composition as defined hereinabove, and wherein preferably with the disease or condition associated with microvascular thrombosis. Preferably, in the method the disease or condition associated with thrombi comprising at least one of VWF and platelets is selected from the group consisting of: acquired or hereditary thrombotic thrombocytopenic purpura (TTP), complement-mediated thrombotic microangiopathy, haemolytic uremic syndrome, antiphospholipid antibody syndrome, non-occlusive thrombus, the formation of an occlusive thrombus, arterial thrombus formation, acute coronary occlusion, peripheral arterial occlusive disease, restenosis and disorders arising from coronary by-pass graft, coronary artery valve replacement and coronary interventions such angioplasty, stenting or atherectomy, hyperplasia after angioplasty, atherectomy or arterial stenting, occlusive syndrome in a vascular system or lack of patency of diseased arteries, transient cerebral ischemic attack, unstable or stable angina pectoris, cerebral infarction, HELLP syndrome, carotid endarterectomy, carotid artery stenosis, critical limb ischemia, cardioembolism, peripheral vascular disease, restenosis, sickle cell disease and myocardial infarct, or a further diseases or conditions defined hereinabove.

In an eighth aspect the invention relates to method for treating or reducing the risk of at least one of microvascular thrombi, fibrin-independent thrombi and thrombi comprising at least one of VWF and platelets. Preferably, in the method at least one these thrombi is treated or the risk of its occurrence is reduced in a disease or condition is selected from the group consisting of: acquired or hereditary thrombotic thrombocytopenic purpura (TTP), complement-mediated thrombotic microangiopathy, haemolytic uremic syndrome, antiphospholipid antibody syndrome, non-occlusive thrombus, the formation of an occlusive thrombus, arterial thrombus formation, acute coronary occlusion, peripheral arterial occlusive disease, restenosis and disorders arising from coronary by-pass graft, coronary artery valve replacement and coronary interventions such angioplasty, stenting or atherectomy, hyperplasia after angioplasty, atherectomy or arterial stenting, occlusive syndrome in a vascular system or lack of patency of diseased arteries, transient cerebral ischemic attack, unstable or stable angina pectoris, cerebral infarction, HELLP syndrome, carotid endarterectomy, carotid artery stenosis, critical limb ischemia, cardioembolism, peripheral vascular disease, restenosis, sickle cell disease and myocardial infarct, or a further diseases or conditions defined hereinabove.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 0.1% of the value.

All patent and literature references cited in the present specification are hereby incorporated by reference in their entirety.

The present invention is further described by the following examples which should not be construed as limiting the scope of the invention.

EXAMPLES

Example 1

Methods and Materials

Nanobody-mUPA Construction

The cDNA sequence for both human and mouse urokinase (PLAU) was obtained from the NCBI database (NM_002658.4 and NM_008873.3 respectively). The sequence for the signal peptide, EGF-like and Kringle domain were removed as well as the first part of the connecting peptide. To the remaining connecting peptide and S1 peptidase domain (Catalytic domain) a N-terminal sequence coding for a Tobacco Etch Virus cleavage site followed by an GGGGS linker was added. In the GGGGS linked a PstI and BamHI digestion site were incorporated without disturbing the amino acid sequence. At the 5' side an EcoRI digestion site was added and at the 3' side and NotI digestion was added after the STOP codon of PLAU. The construct was obtained from IDT (Integrated DNA Technologies, Leuven, Belgium) as a custom gene construct.

Coding sequences for nanobodies (also known as VHH) were codon optimized via IDT for expression in a human host cells. At the N-terminal side of the VHH coding sequence, a sequence coding for a Tobacco Etch Virus cleavage site was placed and at the C-terminal side a GGGGS linker (encoding a PstI and BamHI digestion site). These DNA segments were obtained from IDT as Double stranded DNA fragments (gBLocks).

The custom gene construct was propagated in *E. coli* TOP10 and selected by ampicillin resistance. Obtained plasmid DNA was digested by EcoRI and NotI. The resulting insert (886) was separated on and isolated from agarose gel and ligated into a modified pcDNA6 expression vector (pSM2) (De Maat et al, 2016 J Allergy Clin Immunol November; 30; 138(5):1414-23)). pSM2 encodes a N-terminal murine IgK secretion signal and a double STREP isolation tag whereafter the modified UPA construct is ligated.

Figures 1A, 1B:
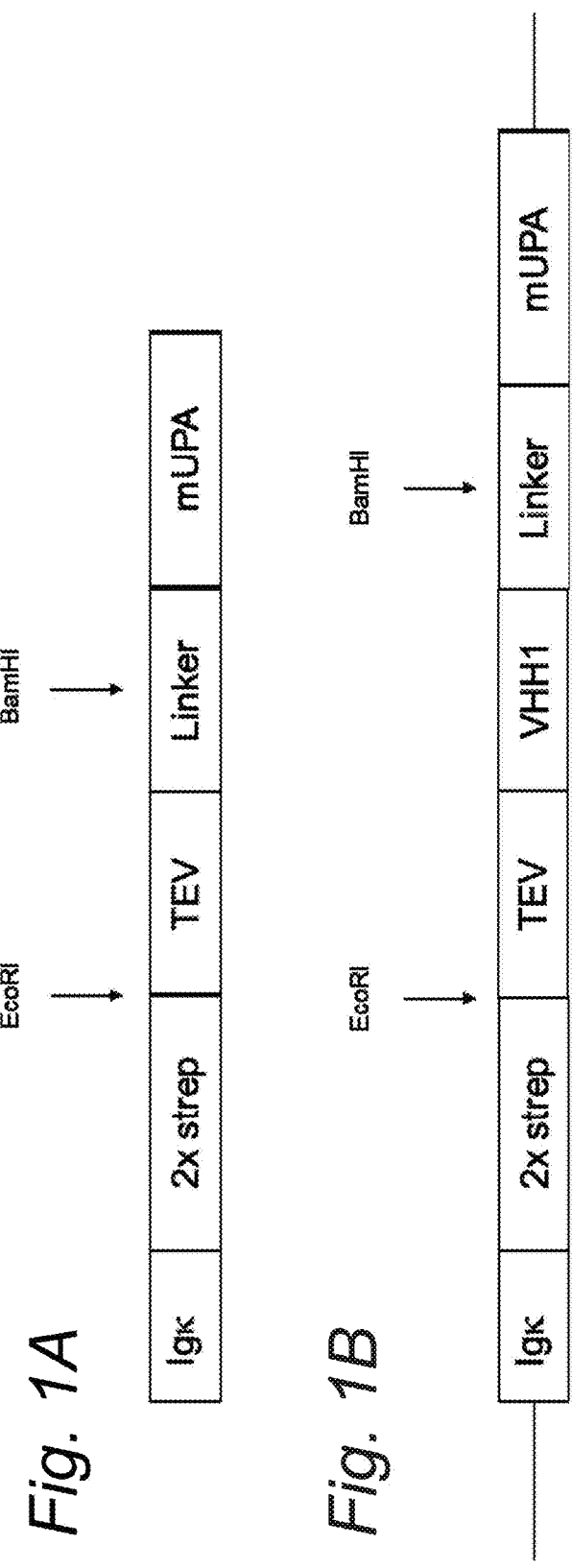
FIG. 1A: Schematic representation of an mUPA construct.
FIG. 1B: Schematic representation of an mUPA construct comprising a VHH coding sequence (VHH-mUPA).

The gBlocks were ligated into the pJET1.2 cloning vector according to manufacturer instructions (CloneJET PCR Cloning Kit; Thermo Fisher). The constructs were propagated in *E. coli* TOP10 and selected by ampicillin resistance. Obtained plasmid DNA was digested by EcoRI and BamHI. The resulting insert was separated on and isolated from agarose gel and ligated into the pSM2 vector containing the miniUPA construct. The gene constructs are schematically depicted in in FIG. 1.

Table 1 lists the nanobody-mUPA fusion protein constructs that were prepared, including the targets of their nanobodies and their names.

TABLE 1

| Description of nanobody-mUPA fusion protein constructs | | |
|---|---|---|
| Specificity | Name | Target |
| VWF | sVWF-mUPA | globular and unfolded VWF |
| | D3-mUPA | D3 domain of VWF |
| | A11-mUPA | A1 domain of VWF |
| | A12-mUPA | A1 domain of VWF |
| Platelets | GP1B17-mUPA | platelet GP1B receptor |
| Negative control | R2-mUPA | no binding to VWF or platelets |

Nanobody-mUPA Production

The nanobody/mUPA-pSM2 constructs were transfected into HEK293 FreeStyle™ cells using 239Fectin as instructed by the manufacturer (ThermoFisher). After 1 day cells were expanded to a 20 mL. 2 Days hereafter the cells were placed under blasticidin (5 µg/mL) selection. Transfected cells were further cultured according to manufacturer instructions until the constructs were stably integrated into the HEK genome. Cell were expanded (to $1.1*10^6$ cells/mL) and after 7 days of protein production, the cells were spun down at 2000×g for 5 minutes. Hereafter the supernatant was collected and benzamine (0.174 mg/mL) was added, where after the supernatant was stored at −20° C. until further use.

Nanobody-mUPA Purification

Collected supernatant (400 mL) was concentrated on a Quixstand to 150 mL using a 10 kDA cutoff membrane (GE healthcare). Hereafter the concentrate was dialyzed against 2 L of 1×STREP buffer containing benzamidine (100 mM Tris, 150 mM NaCl, 0.174 mg/mL Benzamidine, pH 8.0). The concentrate was flowed over a column containing 8 mL Strep-Tactin superflow beads (IBA). After washing the column with 20 mL of 1×STREP buffer, the protein was eluted via d-Desthiobiotin (2.5 mM; Sigma Aldrich) in 1×STREP buffer. The purified proteins were dialyzed against 2 L sodium acetate (4 mM sodium acetate, 150 mM NaCl, pH 5.4) and stored at −80° C.

Results

Purified Nanobody-mUPA Constructs on Western Blot

Figure 2:
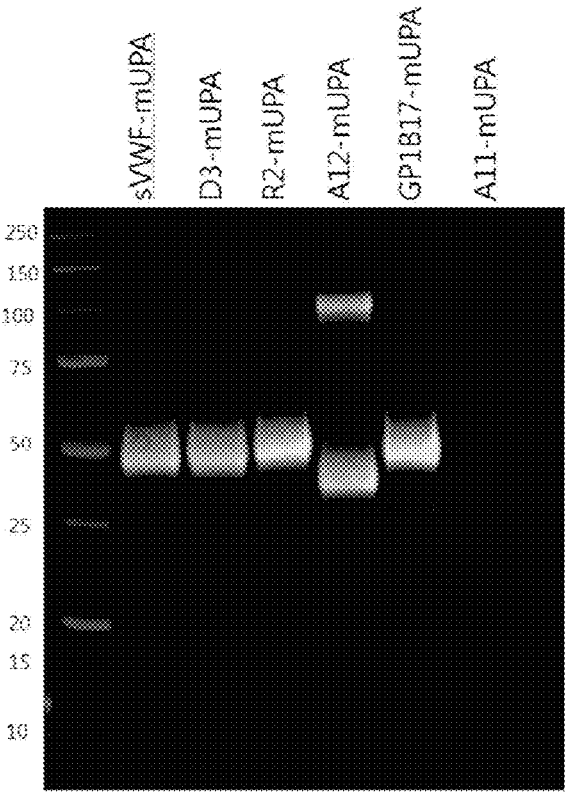
FIG. 2: Western Blot of purified VHH-mUPA constructs.

The nanobody-mUPA constructs were diluted in sample buffer (25 mM DTT) to a concentration of 100 μg/mL. 10 μL sample was loaded onto a 4-12% gradient Bis-Tris gel in MES buffer. Sample separation was performed at 165 Volt for 50 minutes. The gel is transferred onto a Immobilon-FL membrane in blotting buffer for 1 hour at 125 Volt. The membrane is blocked with 0.5× Odyssey blocking buffer where after the constructs are detected with a rabbit polyclonal anti human UPA antibody in combination with an IR800 labeled Goat-anti-Rabbit antibody. Results were analyzed via the near-infrared odyssey scanner (Licor) according to manufacturer instructions. FIG. 2 shows that all fusion proteins except for A11-mUPA were expressed at near-equal levels.

Urokinase Activity of Nanobody-mUPA Constructs

The nanobody-mUPA constructs should display no spontaneous (i.e. non-induced) activity but should be activatable through molecular cleavage by plasmin.

To verify that none of the nanobody-mUPA constructs shows any spontaneous activity, the constructs (1 μg/mL) were incubated in 0.2% BSA-HBS in the presence of a 0.5 mM urokinase substrate (I1140; Bachem). Substrate conversion was measured according to manufacturer instruction at 37° C. None of the fusion proteins showed any detectable spontaneous activity towards the urokinase substrate (data not shown).

Figure 3:
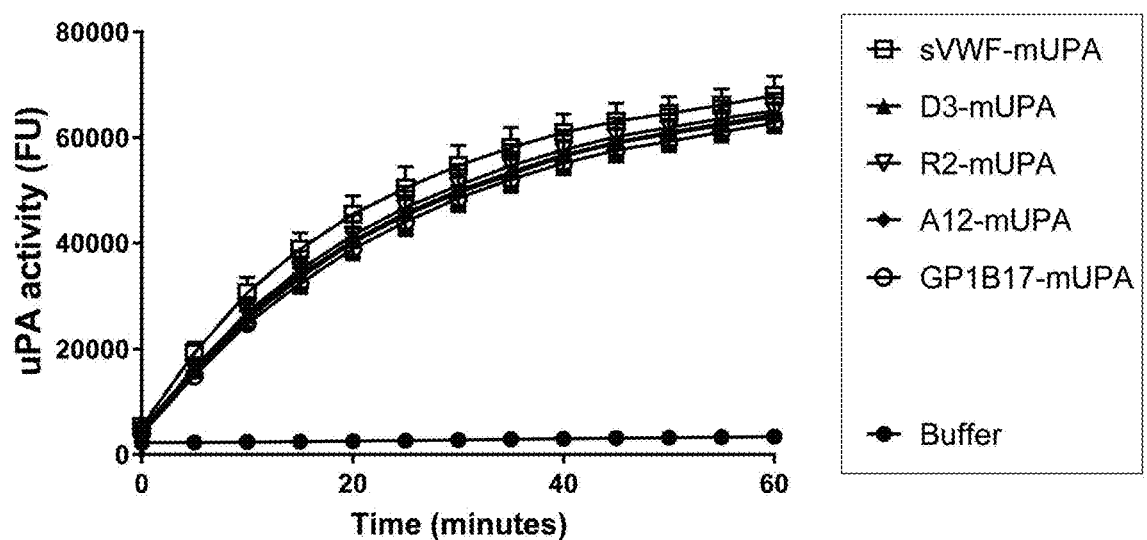
FIG. 3: VHH-mUPA construct activity after activation by plasmin.

To test whether nanobody-mUPA constructs are activatable by plasmin, plasminogen was pre-activated by streptokinase for 15 minutes at 37° C. (hereafter called plasmin). The nanobody-mUPA fusion constructs (1 μg/mL final concentration) were diluted in in 0.2% BSA-HBS and incubated for 12 minutes with plasmin (1 μg/mL final concentration). Subsequently, urokinase substrate (0.5 mM I1140, Bachem) was added and its conversion was measured according to manufacturer's instructions at 37° C. FIG. 3 shows that the fusion proteins are normally activatable.

Plasminogen Activation

Figure 4:
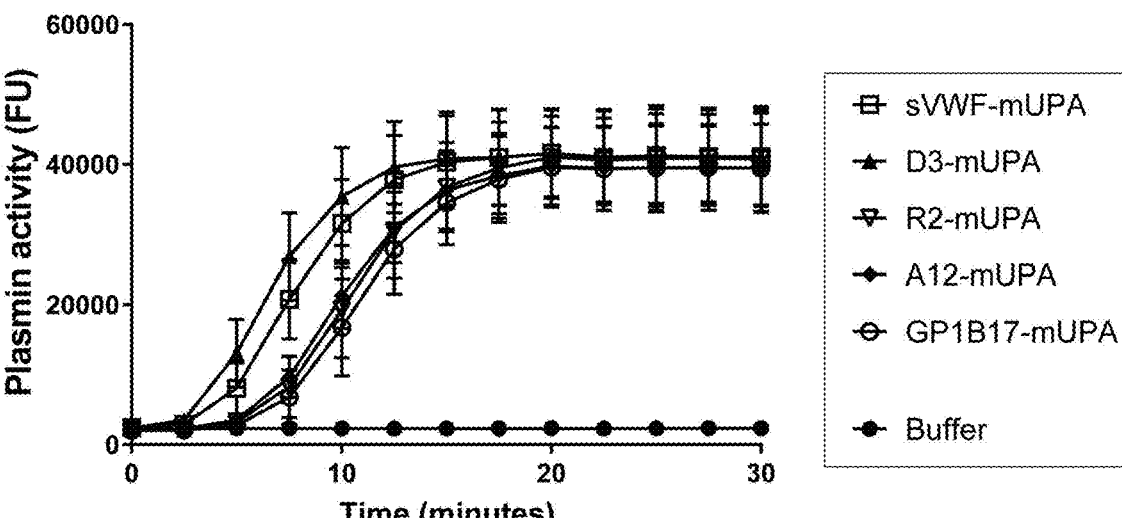
FIG. 4: Plasminogen activation by VHH-mUPA constructs.
Figure 5A:
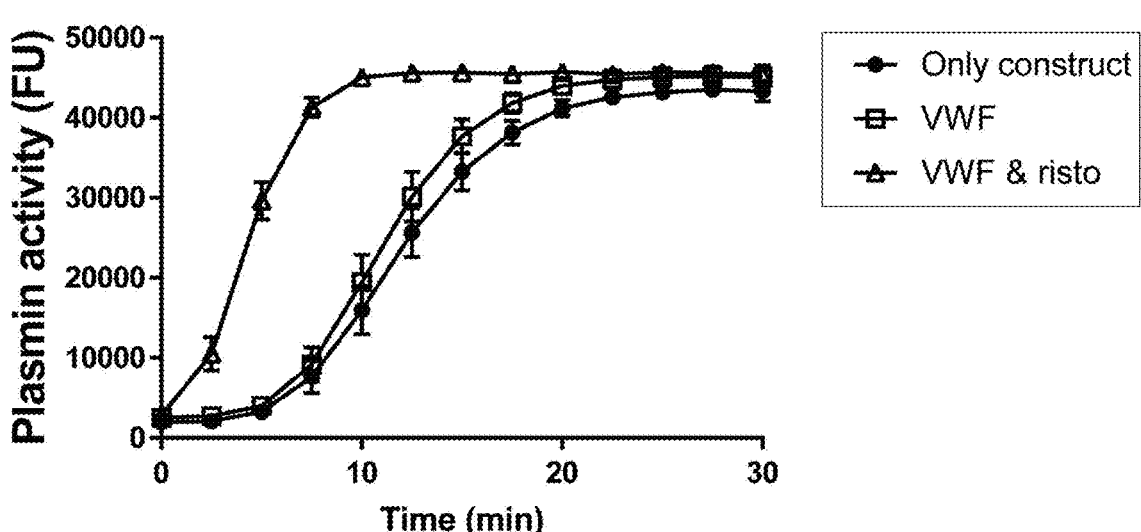
FIG. 5A: Plasminogen activation by VHH-sVWF constructs in the presence of globular or open VWF.
Figure 5B:
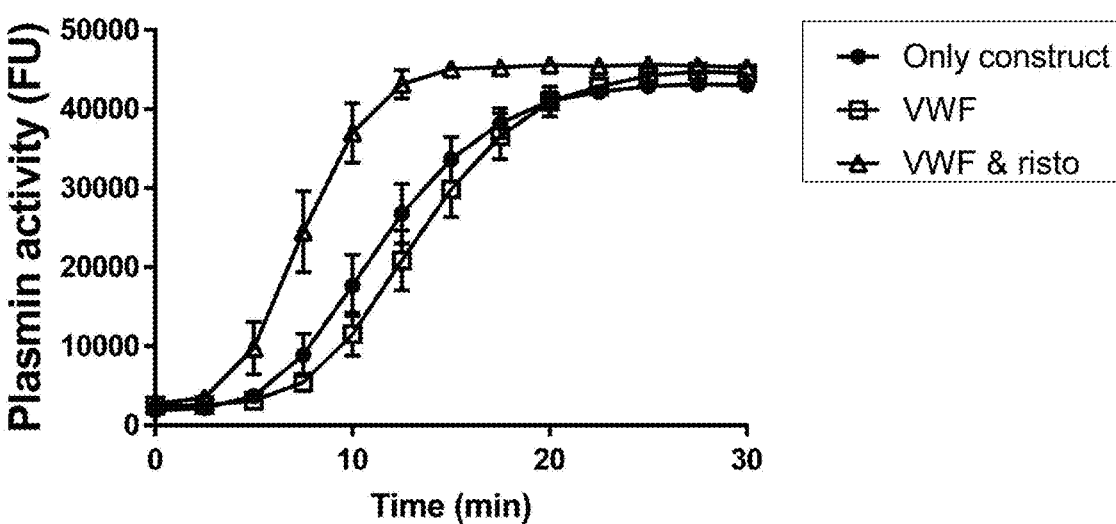
FIG. 5B: Plasminogen activation by VHH-D3 constructs in the presence of globular or open VWF.
Figure 5C:
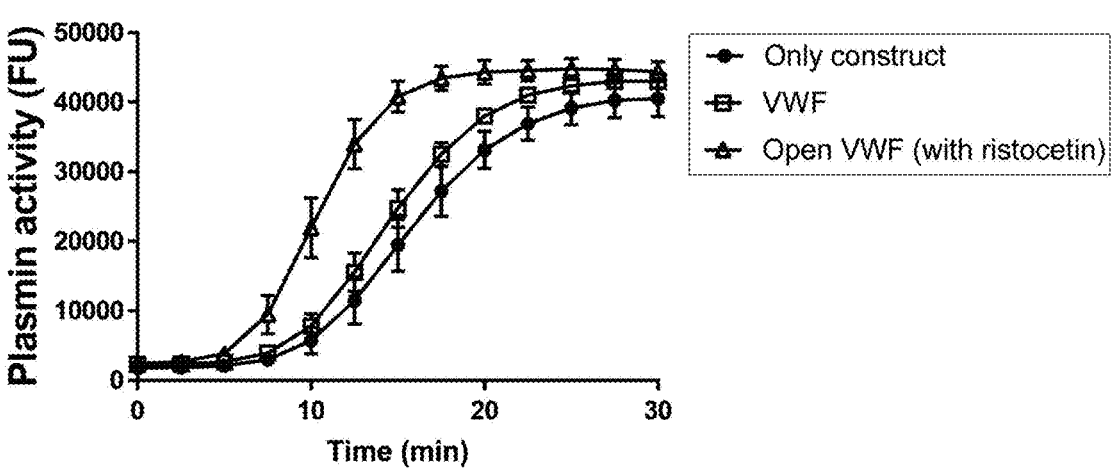
FIG. 5C: Plasminogen activation by VHH-GP1B17 constructs in the presence of globular or open VWF.
Figure 5D:
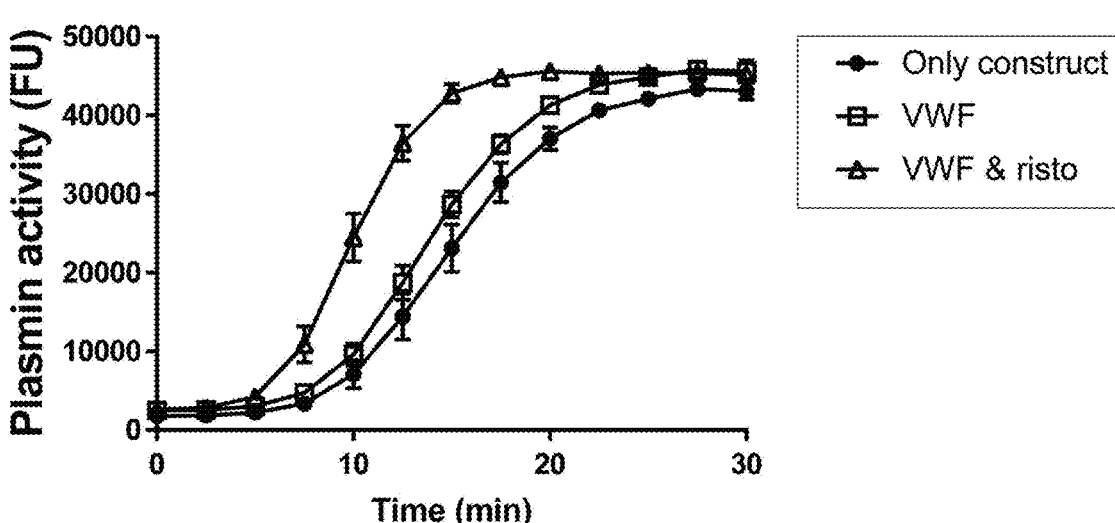
FIG. 5D: Plasminogen activation by VHH-R2 constructs in the presence of globular or open VWF.
Figure 5E:
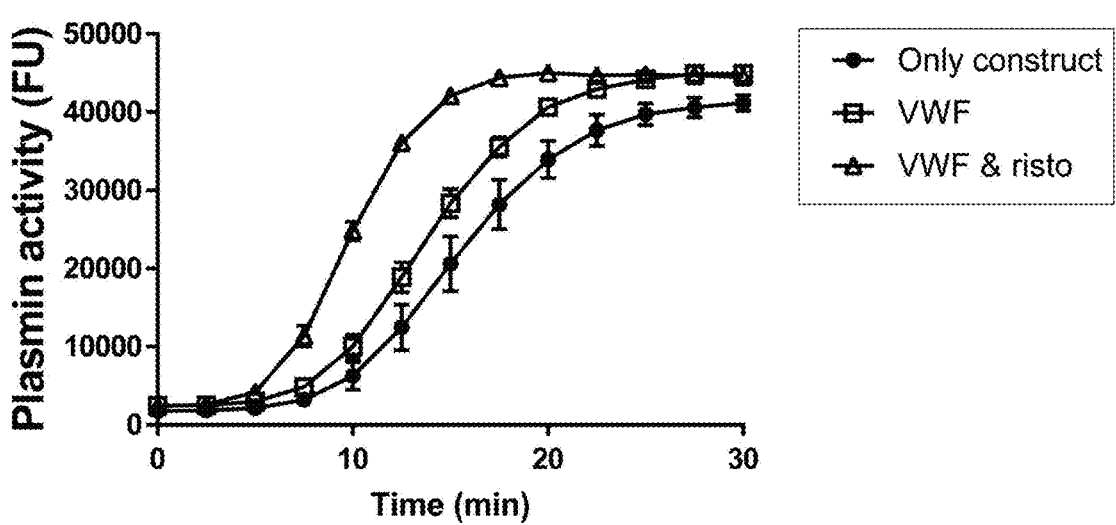
FIG. 5E: Plasminogen activation by VHH-A12 constructs in the presence of globular or open VWF.

The basis of plasminogen activation by urokinase depends on the reciprocal cleavage between urokinase and plasminogen. To test plasminogen activation by the nanobody-mUPA constructs, the constructs (1 μg/mL) were incubated in 0.2% BSA-HBS in the presence of 100 μg/mL plasminogen and 0.2 mM plasmin substrate (I1390; Bachem). Substrate conversion was measured according to manufacturer instruction at 37° C. FIG. 4 shows that all constructs showed development of comparable enzyme activity.

Binding of Anti-VWF Constructs to VWF as Determined by ELISA

A nunc maxisorp plate (Thermo) was coated overnight with 1 μg/mL VWF in PBS. The following day the plate was blocked with 1% BSA-PBS. The anti-VWF nanobody-mUPA fusion constructs were diluted in 1% BSA-PBS at various concentrations after which 50 uL is added to each well and incubated for 1 hours. Hereafter the plate is washed with PBS-Tween 20 (PBST; 0.05% v/v). Bound construct was detected via rabbit anti-UPA polyclonal antibody in combination Goat-anti-rabbit-HRP secondary antibody (Abcam). Wells were rinsed with PBST, after which 100 μl TMB was added at room temperature. Substrate was developed for 5 minutes after which 50 μl $H_2SO_4$ (0.3 M) was added. Results were analyzed at 450 nm by absorption. Results were analyzed by Graphpad Prism 7.02 and the $K_d$ (in nM) was determined via non-linear regression curve fit. Binding affinities are listed in Table 2.

TABLE 2

Binding affinities of anti-VWF nanobody-mUPA fusion constructs to VWF as determined by ELISA.

| Construct | $K_d$ (nM) | Standard deviation |
|---|---|---|
| sVWF-mUPA | 0.03055 | 0.02491 |
| D3-mUPA | 0.3279 | 0.2005 |
| A12-mUPA | 12.84 | 6.571 |
| R2-mUPA | 1039010 | 1798731 |

Plasminogen Activation in the Presence of Globular or Open VWF

Figure 6:
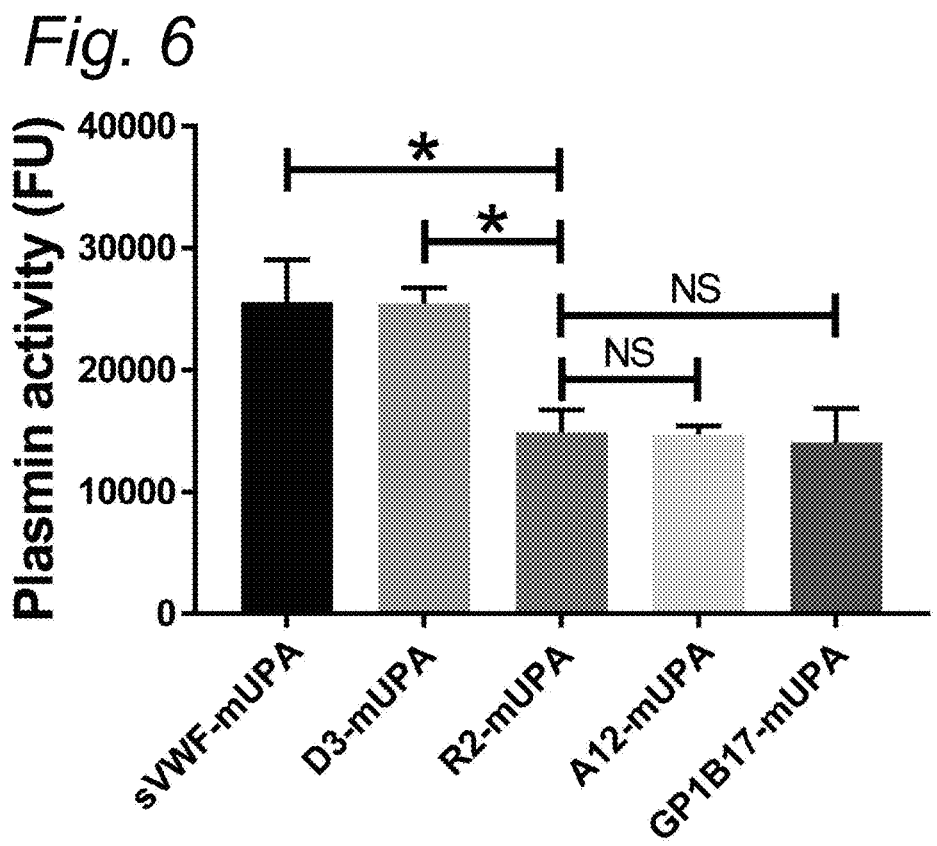
FIG. 6: Plasmin substrate conversion after 5 minutes incubation at 37° C. of the constructs VHH-sVWF, VHH-D3, VHH-GP1B17, VHH-R2, and VHH-A12.
Figure 7A:
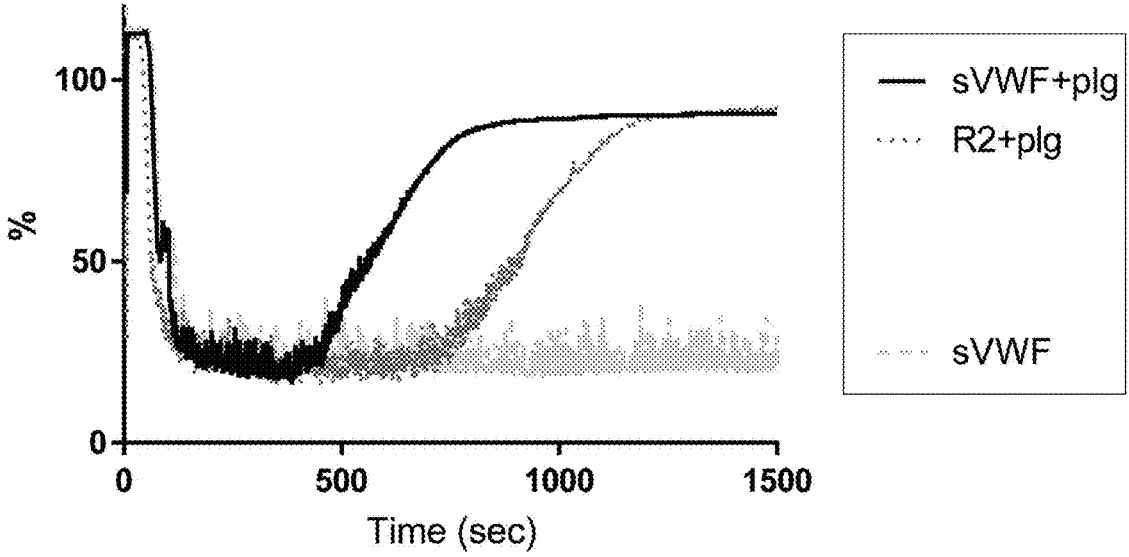
FIG. 7A: Micro-thrombolysis (i.e. enzymatic breakdown) of VWF-platelet agglutinates induced by VHH-sVWF. Lysis of the agglutinates was monitored overtime.
Figure 7B:
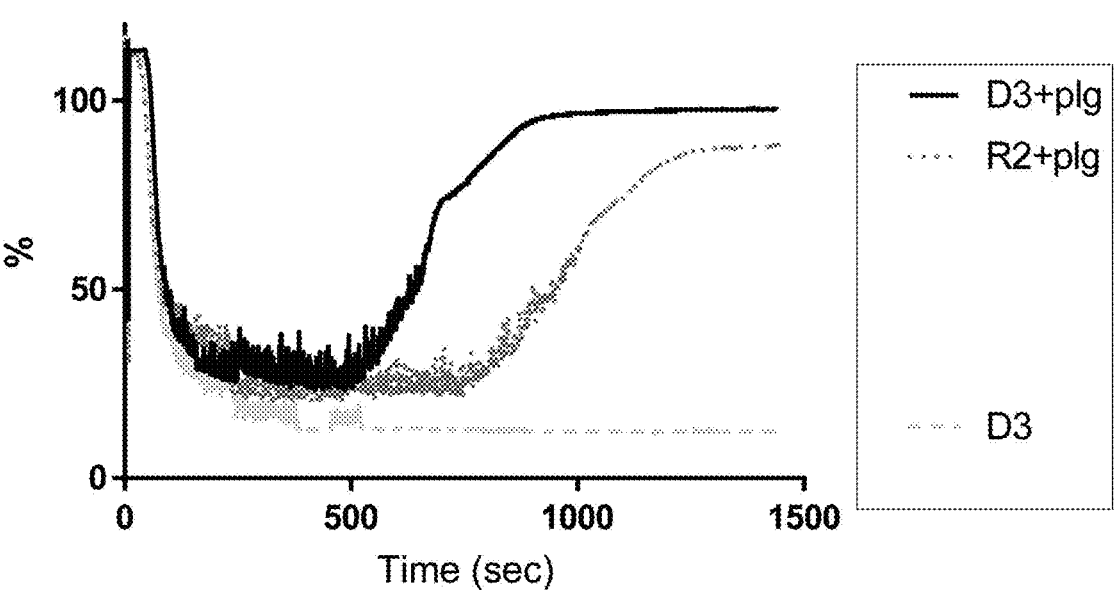
FIG. 7B: Micro-thrombolysis (i.e. enzymatic breakdown) of VWF-platelet agglutinates induced by VHH-D3. Lysis of the agglutinates was monitored overtime.
Figure 7C:
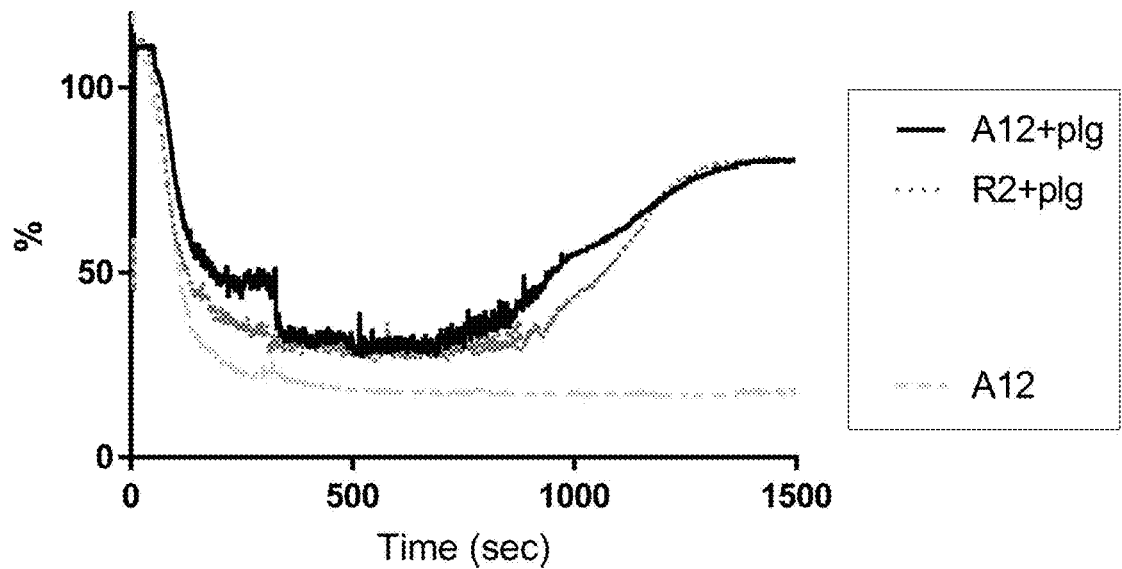
FIG. 7C: Micro-thrombolysis (i.e. enzymatic breakdown) of VWF-platelet agglutinates induced by VHH-R2. Lysis of the agglutinates was monitored overtime.
Figure 7D:
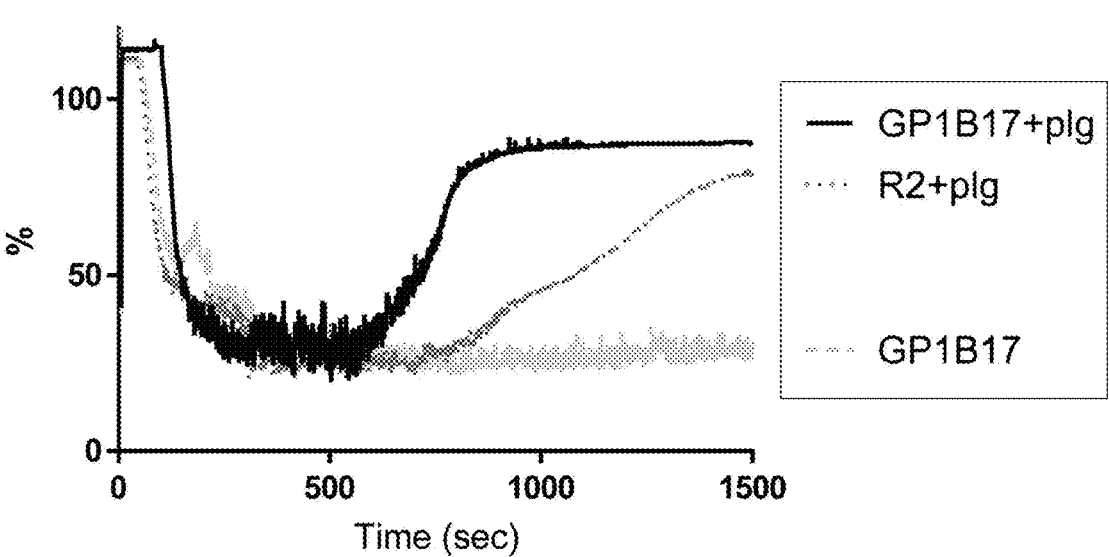
FIG. 7D: Micro-thrombolysis (i.e. enzymatic breakdown) of VWF-platelet agglutinates induced by VHH-GP1B17. Lysis of the agglutinates was monitored overtime.

VWF is the scaffold for microthrombus formation. It also has plasmin(ogen) binding properties that are dependent on protein conformation (Tersteeg et al., 2014, supra). VWF unfolds under shear stress (as well as during immobilization on microtiter plates—see previous experiment). This can be mimicked by incubation with the small molecule ristocetin. We asked whether plasminogen activation by our targeted fusion proteins is influenced by the conformation of VWF. The nanobody fusion constructs (0.25 μg/mL) and VWF (5 μg/mL) are diluted in 0.2% BSA-HBS. Hereafter, ristocetin (0.6 mg/mL) or buffer is added to open up the VWF or keep it globular, respectively, while incubating at 37° C. for 5 minutes. Hereafter plasminogen is added (100 μg/mL) followed by plasmin substrate (I1390 Bachem; 0.2 mM). Substrate conversion was measured according to manufacturer's instructions at 37° C. For comparison, the substrate at conversion after 5 minutes was shown for the different constructs. In the bar graph below. Data was processed in Graphpad Prism 7.02 and analyzed by one-way Anova. *P<0.05. FIGS. 5 and 6 show that the time to development of plasmin activity is significantly shorted by open VWF (in the presence of ristocetin) as compared to closed VWF.

Micro-Thrombolysis of VWF-Platelet Agglutinates.

Figure 8A:
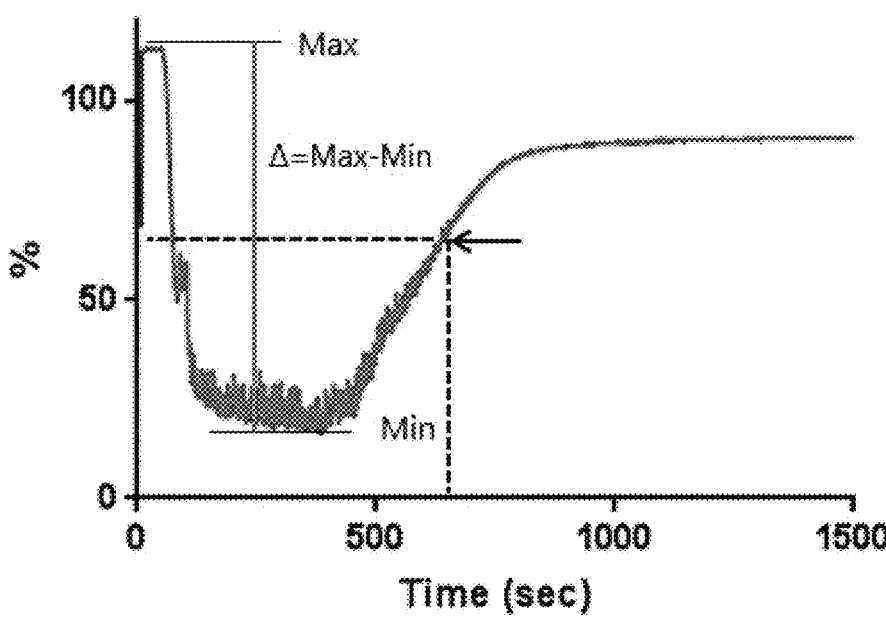
FIG. 8A: Graphic example of analytical method to determine time points by which 50% microthrombus degradation has occurred.
Figure 8B:
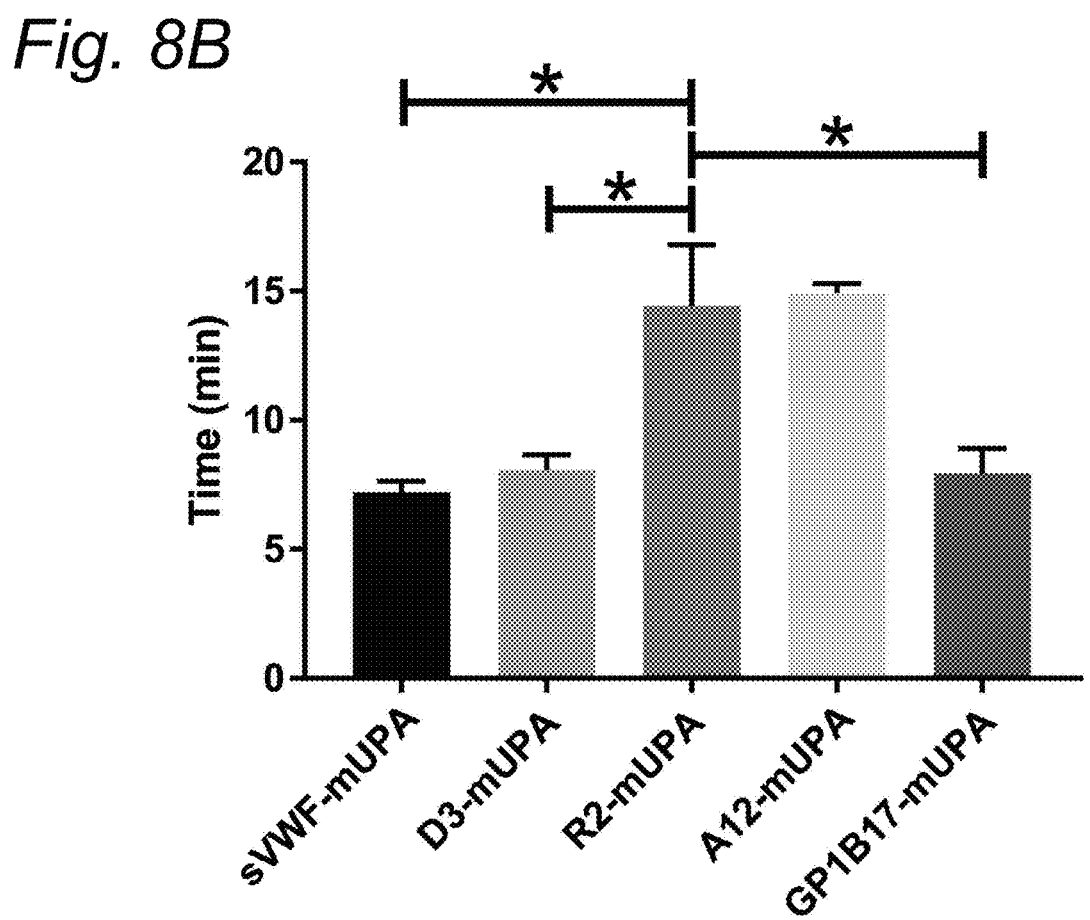
FIG. 8B: 50% microthrombus degradation of the constructs VHH-sVWF, VHH-D3, VHH-GP1B17, VHH-R2, and VHH-A12.

Blood platelets were isolated from citrated whole blood according to earlier described methods (Tersteeg et al., 2014, supra). Isolated blood platelets (200,000/mL) were incubated with VWF (5 μg/mL), plasminogen (100 μg/mL) and the aggregation inhibitors RGDW (200 μM) and Iloprost (0.4 μg/mL) for 15 minutes at 37° C. in a light transmission aggregometer. Agglutination was induced by the addition of ristocetin (0.6 mg/mL). 6 minutes hereafter, the nanobody-mUPA constructs (1 μg/mL) were added and lysis of the agglutinates was monitored overtime (FIG. 7). For all samples, time points were determined by which 50% microthrombus degradation has occurred (graphic example of analytical method is shown in FIG. 8A). Results were processed in Graphpad Prism 7.02 and analyzed by one-way Anova (*P<0.05) and are shown in FIG. 8B. Clearly, the targeting of plasminogen activation by at least the fusion proteins sVWF-mUPA, D3-mUPA and GP1B17-mUPA accelerates microthrombolysis.

Example 2: Micro-Thrombolysis of VWF-Platelet on Endothelial Cells in Flow Perfusion

Materials and Methods

Human Vascular Endothelial Cell (Huvecs) Culture on Cover Glasses

Huvecs (passage 0) stored in liquid nitrogen were thawed at 37° C. and added to medium 1:10 (EBM-2 Lonza or Promocel supplemented with huvec growth factors EGM2) and spun down 100 g for 5 minutes. Supernatant was discarded and cells were taken up in 5 mL medium and cultured in T25 flasks at 37 degrees Celsius, 5% $CO_2$. The following day the cells were passed to 3×T75 flasks. On day 6 the cells are passed 1:6 to the cover glasses pre-treated with 1.25% glutaraldehyde in HT-buffer pH 7.4 (HEPES Tyrode buffer: 10 mM HEPES, 0.5 mM $Na_2HPO_4$, 145 mM NaCl, 5 mM KCl, 1 mM $MgSO_4$).

To coat cover glasses with glutaraldehyde, coverglasses were rinsed with demi water and with ethanol. Cover glasses were then incubated in HCL 37%:methanol (1:1) for 30 minutes followed by a rinse with demi water for 5 minutes. Next cover glasses were incubated in aminopropyltriethoxysilane:ethanol (1:100) for 30 seconds followed by a rinse with demi water and with ethanol. Cover glasses were then dried and incubated with glutaraldehyde 20%:HT-buffer pH 7.4 (1:20) for 1 hour followed by a rinse with demi water and glasses are stored in ethanol until use.

Huvecs were cultured on the cover glasses for approximately 10-15 days prior to use.

Heat Inactivated Plasma Preparation

Heat inactivated plasma was prepared by mixing two bags of plasma (Ominplasma from octapharma both bloodtype AB Lot No: C442A9521, bags: X000214223782; X000214223577). 200 mL of this mix was divided over 10 falcon tubes (50 mL, 20 mL each) and were incubated in a water bath set at exactly 56° C. for 30 minutes (the 20 mL was completely submerged) and halfway through (15 min) the falcon tubes were mixed. Following the 30 min incubation the falcon tubes were covered in ice and kept on ice until centrifuging (note: when removing the tubes from ice for centrifugation the tubes were still rather warm). The tubes were centrifuged 5 minutes (without cooling) at 15,000 g. The supernatant was combined and kept on ice until aliquoting in 1 mL aliquots.

Flow Chamber Setup

A laminar-flow perfusion chamber was filled with pre-warmed medium to remove all air from the tubing prior to placing the coverslips. The inlet tube was cut to a length that corresponds with a volume of 90.6 µL so that during the perfusion the fluid that enters the inlet arrives into the perfusion chamber after exactly 1 minute. The syringe that is used has a diameter of 16 mm (only for braun 12 ml syringes) and the syringe pump is set to 90.6 µL per minute as this (with 3 mm tubing) results in a shear rate of 300 $s^{-1}$. The huvec coverslip is placed on the medium, attached with the vacuum set at 10 bar and the perfusion chamber is placed under an inverted microscope (Zeiss observer Z.1, Carl Zeiss) with heating module that keeps the perfusion chamber at 37° C. Any remaining air bubbles are removed by perfusing medium.

Washed Platelets in Heat Inactivated Plasma

Blood from healthy consenting volunteers was collected into 0.1 volume 3.2% 10.9 mM trisodium citrate. Platelet-rich plasma (PRP) was obtained by centrifugation (160 g for 15 min at RT). PRP supplemented with 10% (v/v) acid citrate dextrose, 85 mM tri-sodiumcitrate, 71 mM citric acid, 111 mM D-glucose, was centrifuged (400 g for 15 min at RT) and platelets were resuspended in HEPES tyrode buffer pH 6.5 containing 0.145M NaCl, 5 mM KCl, 0.5 mM $Na_2HPO_4$, 1 mM $MgSO_4$, 10 mM HEPES and 5.5 mM D-glucose. 10 µg/mL $PGI_2$ was added to the platelet suspension prior to another centrifugation step (400 g for 15 min at room temperature) and platelets were resuspended in heat inactivated plasma and platelet count was adjusted to a final count of 200 G/L.

Perfusion Experiment Setup

The heat inactivated plasma containing 200 G/L platelets (that is pre-warmed in 37° C. waterbath) is divided over 2 mL eppendorfcups (40 min experiment→2×2 mL required, etc). and prior to the start to all eppendorfcups illoprost (8 µL (250 fold dilution) of 0.1 mg/mL stock is added, final concentration 0.4 µg/mL, Bayer Schering Pharma AG) is added first, followed by histamine (4 µL (500 fold dilution) of 500 µM stock in medium, final concentration 100 µM). The perfusion is started immediately after the addition of Iloprost and histamine by transferring the inlet tube from the 2 mL eppendorfcup containing medium to the eppendorfcup containing heat inactivated plasma with platelets by squeezing the tube to ensure no air is introduced. The experiment is started with frame 1 after approximately 1 minute, when the first platelets enter the flow chamber (visible change). After 7 minutes the constructs are added to the remaining (2000−634.2=1365.8 µL because 7*90.6=634 µL is used at this point) by pipetting the required volume directly into the eppendorfcup and mixing with a plastic pipette, final concentration is 10 µg/mL. At this point the construct is also added to the additional Eppendorf cups to make sure the pre-incubation time with plasma remains equal. During the perfusion the 2 mL Eppendorf cup needs to be re-filled by carefully adding plasma with a plastic pipette drop by drop. This refill is done at frames 150, 250, etc. so that potential disturbances due to the refilling can be matched to the corresponding frames/time points. During the experiment every 5 seconds a DIC image is made and at the end of the experiment 5 screenshots are made of other regions in the perfusion chamber and the number of platelet-VWF complexes, visible in the form of "platelet-strings" are counted.

Results

Figure 9:
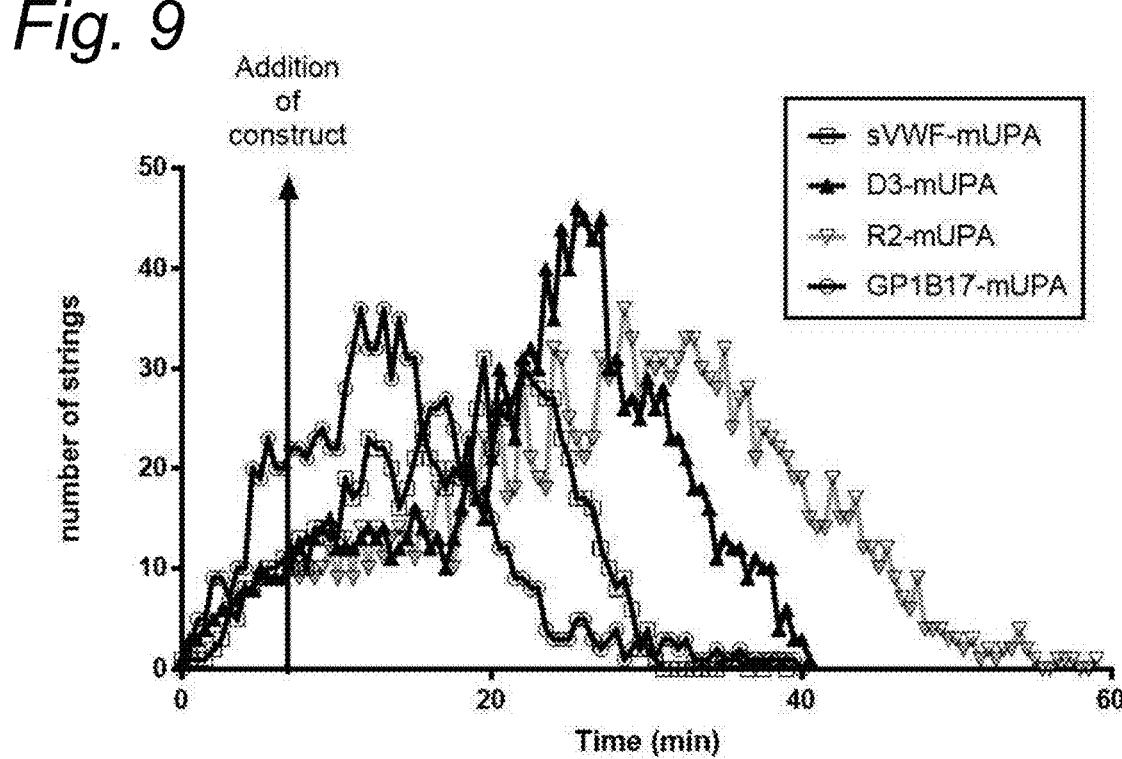
FIG. 9: Micro-thrombolysis of VWF-platelet complexes adhered to human vascular endothelial cells as analyzed in flow perfusion experiments. VWF-platelet complexes are visible as strings of platelets and the number of visible string are counted as a function of time in response to the addition of fusion proteins as indicated.

The results are shown in FIG. 9, which shows that targeted plasminogen activation by at least the fusion proteins GP1B17-mUPA, sVWF-mUPA and D3-mUPA accelerates thrombolysis of platelet-VWF complexes bound to Huvecs, as compared to the control fusion protein R2-mUPA. In particular fusion protein GP1B17-mUPA, rapidly clears platelet-VWF complexes, which demonstrates that in particular targeting of platelets is efficient in clearing platelet-VWF complexes in microthrombi.

Example 3

Methods and Materials

Caplacizumab Production

Cloning

Caplacizumab (a bi-valent variant of the Cablivi VHH) was produced in *E. coli* and purified via HIS-tag affinity chromatography. The Caplacizumab protein sequence was derived from its EMA assessment report (EMA/490172/2018; Procedure No. EMEA/H/C/004426/0000) and codon optimized for *E. coli* expression via the integrated DNA technologies (IDT) codon optimized tool. N-terminal BamHI and C-terminal NotI digestion sites were added to the constructs and ordered as a double stranded DNA fragment from IDT (SEQ ID NO:40).

The DNA fragment were dissolved in 5 mM Tris-buffer (pH=8.5) and heated at 50° C. for 20 minutes. Hereafter the DNA fragment was ligated into the pJET1.2 vector (CloneJET PCR Cloning Kit; Thermo Fisher) according to manufacturer instructions. The ligated product was transformed into chemically competent *E. coli* TOP10 (Thermo Fisher)

via heat shock according to manufacturer instructions. Transformed bacteria were cultured in 10 mL 2×YT media (containing 100 μg/mL ampicillin) and grown overnight at 37° C. Plasmid DNA was isolated via the plasmid isolation kit (M&N) according to manufacturer instructions. The insert was digested via BamHI-HF and NotI-HF (NEB) in Cutsmart buffer and separated on 0.7% (w/v) agarose gel (1×TBE buffer; 1:10.00 gel red) at 130V for 1 hours. The insert was excised from gel and purified via the PCR&Gel cleanup kit (M&N) according to manufacturer instructions.

The purified insert was ligated into the pTH4.0 vector. The pTH4.0 vector is a modified pET32a(+) vector encoding an N-terminal PelB signal peptide; a His6 tag for purification purposes and a sequence encoding a cleavage site for the tobacco etch virus (TEV) protease followed by a BamHI digestion site. After the C-terminal NotI digestion a myc-tag was placed for detection purposes followed by a stop-codon (Table 1). The pTH4.0 vector was digested via BamHI-HF and NotI-HF and subsequently purified as described for the fragments. The fragment were ligated into the digested pTH4.0 vector in a 3:1 ratio via T4 ligase in 1×T4 ligate buffer according to manufacturer instructions. The ligation mixture was transformed in TOP10 bacteria as described before, and the transformed bacteria were grown on YT-agar plate (100 μg/mL ampicillin, 2% (w/v) glucose) overnight at 37° C. Colonies were picked, and grown in 10 mL 2×YT media (containing 100 μg/mL ampicillin, 2% (w/v) glucose). Plasmid DNA was isolated as described before. The DNA sequence was confirmed by sanger-sequencing via Macrogen (SEQ ID NO: 41).

Production

Caplacizumab in pTH4.0 plasmid DNA was transformed into chemically competent BL21 pLysS *E. coli* (Thermo) according to manufacturer instructions. Transformed bacteria were cultured overnight at 37° C. in 10 mL 2×YT media (containing 100 μg/mL ampicillin, 34 μg/mL chloramphenicol and 2% (w/v) glucose). The overnight was diluted 1:10 in 2×YT media (containing 100 μg/mL ampicillin, 34 μg/mL chloramphenicol and 2% (w/v) glucose) and grown for 3 hours at 37° C. Hereafter the culture was diluted 1:100 in 2×YT media (containing 100 μg/mL ampicillin, 34 μg/mL chloramphenicol) and grown at 37° C. for ~3 hours. When the bacteria reached OD600 nm=0.6, protein production was induced by the addition of Isopropyl β-D-1-thiogalactopyranoside (0.1 mM final concentration). Protein production was performed overnight at 24° C. Bacteria were pelleted at 5000×g for 15 minutes and the supernatant was discarded. The bacteria pellet from 400 ml culture was resuspended in 25 mL dulbecco's phosphate buffer saline (PBS; 137 mM NaCl, 2.7 mM KCl, 1.5 mM KH2PO4, 8.2 mM Na2HPO4, pH=7.4) and frozen at −20° C.

Purification

The frozen bacteria were thawed at 37° C. and pelleted at 10,000×g for 15 min by centrifugation. The supernatant was transferred to new tubes. 5 mL of Cobalt-sepharose beads (TALON Superflow, G&E Healthcare; 50% solution) were washed by PBS according to manufacturer instructions, added to the supernatant and incubated for 2 hours at room temperature on a roller bench. The TALON was pelleted at 1000×g for 5 minutes by centrifugation. Supernatant was discarded and the pellets were dissolved in 20 mL of PBS. The TALON washing was repeated three times in total. After the last step, the TALON was dissolved in 8 mL of PBS and loaded into a PD-10 column. The column was rinsed with an excess of PBS. The column was eluted with Imidazole (150 mM in PBS) and 0.5 mL fractions were collected. Protein containing fraction were pooled and dialyzed overnight against HEPES-buffered saline (HBS: 10 mM HEPES, 150 mM NaCl, pH=7.4) via a 3.500 MWCO dialysis membrane (3 RC tubing; Spectra/Por). Protein concentration was determined by absorption at 280 nm on the DeNovix Spectrophotometer (DS-11), where after the concentrations were corrected for their extinction coefficient (calculated via ProtParam). Purity was assessed by SDS-PAGE with Coomassie Page Blue staining.

Microthrombolysis of VWF-Platelet Agglutinates.

Blood platelets were isolated from citrated whole blood according to earlier described methods (Tersteeg et al., 2014, supra). Isolated blood platelets (200,000/μL) were incubated with VWF (5 μg/mL), plasma-purified plasminogen (100 μg/mL) and the aggregation inhibitors RGDW (200 μM) and Iloprost (0.4 μg/mL) for 15 minutes at 37° C. in a light transmission aggregometer. Agglutination was induced by the addition of ristocetin (0.6 mg/mL). 6 minutes hereafter, the nanobody-mUPA constructs or Caplacizumab were added and lysis of the agglutinates was monitored overtime. For all samples, time points were determined by which 50% microthrombus degradation has occurred (graphic example of analytical method is shown in FIG. 8A). Results were processed in Graphpad Prism 7.02 and analyzed by one-way ANOVA (*P<0.05) and are shown in FIG. 10.

Results

Figure 10A:
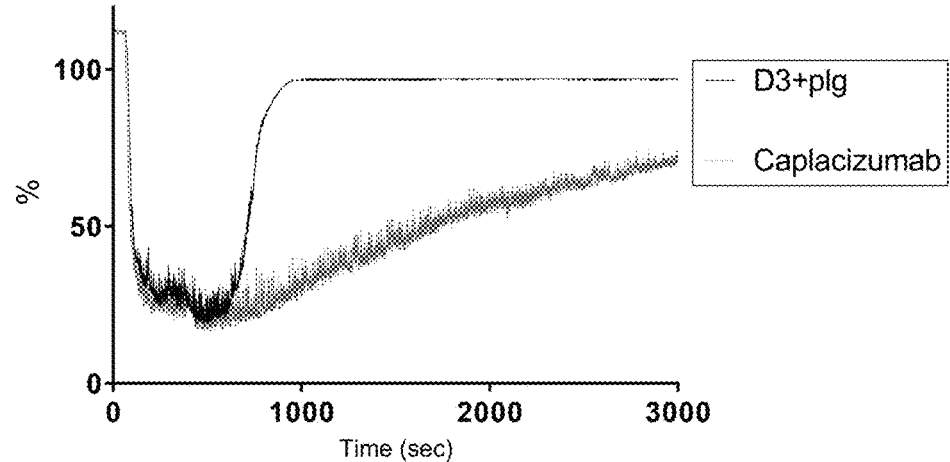
FIG. 10A: Micro-thrombolysis (i.e. enzymatic breakdown) of VWF-platelet agglutinates induced by (154.3 nM) Caplacizumab or (154.3 nM) VHH-D3 fusion protein with UPA in the presence of (100 µg/mL) plasminogen. Lysis of the agglutinates was monitored overtime on a light transmission aggregometer.
Figure 10B:
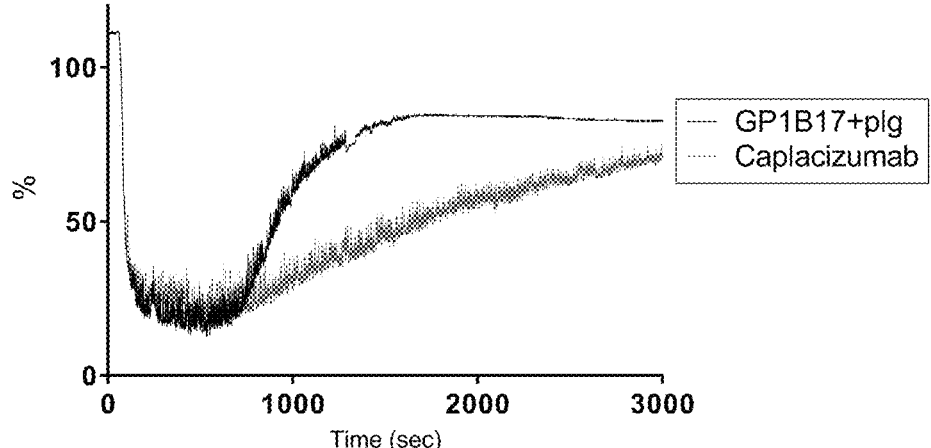
FIG. 10B: Micro-thrombolysis (i.e. enzymatic breakdown) of VWF-platelet agglutinates induced by (154.3 nM) Caplacizumab or (154.3 nM) VHH-GP1B17 fusion protein with UPA in the presence of (100 µg/mL) plasminogen. Lysis of the agglutinates was monitored overtime on a light transmission aggregometer.

Results are shown in FIG. 10 wherein it can be clearly seen that the targeting of plasminogen activation by at least the fusion proteins, D3-mUPA and GP1B17-mUPA accelerates microthrombolysis as compared to the microthrombolysis induced by Caplacizumab.

TABLE 3

Description of the sequences

| SEQ ID NO: | Seq name | Sequence |
|---|---|---|
| 1 | hmUPA | LKFQCGQKTLRPRFKIIGGEFTTIENQPWFAAIYRRHRGGSVTYVCGGSLIS PCWVISATHCFIDYPKKEDYIVYLGRSRLNSNTQGEMKFEVENLILHKDYSA DTLAHHNDIALLKIRSKEGRCAQPSRTIQTICLPSMYNDPQFGTSCEITGFG KENSTDYLYPEQLKMTVVKLISHRECQQPHYYGSEVTTKMLCAADPQWKT DSCQGDSGGPLVCSLQGRMTLTGIVSWGRGCALKDKPGVYTRVSHFLPW IRSHTKEENGLAL |
| 2 | mmUPA | QGFQCGQKALRPRFKIVGGEFTEVENQPWFAAIYQKNKGGSPPSFKCGGS LISPCWVASAAHCFIQLPKKENYVVYLGQSKESSYNPGEMKFEVEQLILHEY YREDSLAYHNDIALLKIRTSTGQCAQPSRSIQTICLPPRFTDAPFGSDCEITGF GKESESDYLYPKNLKMSVVKLVSHEQCMQPHYYGSEINYKMLCAADPEW KTDSCKGDSGGPLICNIEGRPTLSGIVSWGRGCAEKNKPGVYTRVSHFLD WIQSHIGEEKGLAF |

TABLE 3-continued

| | Description of the sequences | |
|---|---|---|
| SEQ ID NO: | Seq name | Sequence |

| SEQ ID NO: | Seq name | Sequence |
|---|---|---|
| 3 | secretion signal peptide | METDTLLLWVLLLWVPGSTGD |
| 4 | 2xSTREP | GSSAWSHPQFEKGSSAWSHPQFEK |
| 5 | TEV | EFENLYFQS |
| 6 | LINKER | SAAGGGGSGGGGSAAA |
| 7 | sVWF-hmUPA | METDTLLLWVLLLWVPGSTGDGSSAWSHPQFEKGSSAWSHPQFEKEFEN LYFQSEVQLVESGGGLVQAGGSLRLSCAASGRTFSSNAMGWFRQAPGKE REFVAAISWSGGSTYYLDSVKGRFTISRDNAKNTVYLQMNSLKPEDTAVYY CAGSAGLGYVGDPDAMDYWGKGTQVTVSSSAAGGGGSGGGGSAAALK FQCGQKTLRPRFKIIGGEFTTIENQPWFAAIYRRHRGGSVTYVCGGSLISPC WVISATHCFIDYPKKEDYIVYLGRSRLNSNTQGEMKFEVENLILHKDYSADT LAHHNDIALLKIRSKEGRCAQPSRTIQTICLPSMYNDPQFGTSCEITGFGKE NSTDYLYPEQLKMTVVKLISHRECQQPHYYGSEVTTKMLCAADPQWKTDS CQGDSGGPLVCSLQGRMTLTGIVSWGRGCALKDKPGVYTRVSHFLPWIR SHTKEENGLAL |
| 8 | D3-hmUPA | METDTLLLWVLLLWVPGSTGDGSSAWSHPQFEKGSSAWSHPQFEKEFEN LYFQSEVQLVESGGGLVQAGGSLRLSCAASGQTLSNYVMGWFRQAPGKE REFVAVISRVGGSTSYADSAKGRFTISRDNAKNTVYLQMNSLKPEDTAVYY CAAAYTIAVVTAMREYDFWGQGTQVTVSSSAAGGGGSGGGGSAAALKF QCGQKTLRPRFKIIGGEFTTIENQPWFAAIYRRHRGGSVTYVCGGSLISPC WVISATHCFIDYPKKEDYIVYLGRSRLNSNTQGEMKFEVENLILHKDYSADT LAHHNDIALLKIRSKEGRCAQPSRTIQTICLPSMYNDPQFGTSCEITGFGKE NSTDYLYPEQLKMTVVKLISHRECQQPHYYGSEVTTKMLCAADPQWKTDS CQGDSGGPLVCSLQGRMTLTGIVSWGRGCALKDKPGVYTRVSHFLPWIR SHTKEENGLAL |
| 9 | R2-hmUPA | METDTLLLWVLLLWVPGSTGDGSSAWSHPQFEKGSSAWSHPQFEKEFEN LYFQSQVQLQESGGGLVQAGGSLRLSCAASGRATSGHGHYGMGWFRQV PGKEREFVAAIRWSGKETWYKDSVKGRFTISRDNAKTTVYLQMNSLKPED TAVYYCAARPVRVDDISLPVGFDYWGQGTQVTVSSSAAGGGGSGGGGSA AALKFQCGQKTLRPRFKIIGGEFTTIENQPWFAAIYRRHRGGSVTYVCGGSL ISPCWVISATHCFIDYPKKEDYIVYLGRSRLNSNTQGEMKFEVENLILHKDYS ADTLAHHNDIALLKIRSKEGRCAQPSRTIQTICLPSMYNDPQFGTSCEITGF GKENSTDYLYPEQLKMTVVKLISHRECQQPHYYGSEVTTKMLCAADPQW KTDSCQGDSGGPLVCSLQGRMTLTGIVSWGRGCALKDKPGVYTRVSHFLP WIRSHTKEENGLAL |
| 10 | A11-hmUPA | METDTLLLWVLLLWVPGSTGDGSSAWSHPQFEKGSSAWSHPQFEKEFEN LYFQSAVQLVESGGRLVKAGASLRLSCAASGRTFSSLPMAWFRQAPGKER EFVAFIGSDSSTLYTSSVRGRFTISRDNGKNTVYLQMMNLKPEDTAVYYCA ARSSAFSSGIYYREGSYAYWGQGTQVTVSSSAAGGGGSGGGGSAAALKF QCGQKTLRPRFKIIGGEFTTIENQPWFAAIYRRHRGGSVTYVCGGSLISPC WVISATHCFIDYPKKEDYIVYLGRSRLNSNTQGEMKFEVENLILHKDYSADT LAHHNDIALLKIRSKEGRCAQPSRTIQTICLPSMYNDPQFGTSCEITGFGKE NSTDYLYPEQLKMTVVKLISHRECQQPHYYGSEVTTKMLCAADPQWKTDS CQGDSGGPLVCSLQGRMTLTGIVSWGRGCALKDKPGVYTRVSHFLPWIR SHTKEENGLAL |
| 11 | A12-hmUPA | METDTLLLWVLLLWVPGSTGDGSSAWSHPQFEKGSSAWSHPQFEKEFEN LYFQSQVQLVESGGGLVQAGGSLRLSCTASGRTFSTYALGWFRQVPGKGR EFIAVIYWRDGSSLYSDSVKGRFTISKDNAKNTVYLQMNSLKPEDTAVYYC ANRHDSRGTYYSSRGYDYWGQGTQVTVSSSAAGGGGSGGGGSAAALKF QCGQKTLRPRFKIIGGEFTTIENQPWFAAIYRRHRGGSVTYVCGGSLISPC WVISATHCFIDYPKKEDYIVYLGRSRLNSNTQGEMKFEVENLILHKDYSADT LAHHNDIALLKIRSKEGRCAQPSRTIQTICLPSMYNDPQFGTSCEITGFGKE NSTDYLYPEQLKMTVVKLISHRECQQPHYYGSEVTTKMLCAADPQWKTDS CQGDSGGPLVCSLQGRMTLTGIVSWGRGCALKDKPGVYTRVSHFLPWIR SHTKEENGLAL |
| 12 | GP1B-17 hmUPA | METDTLLLWVLLLWVPGSTGDGSSAWSHPQFEKGSSAWSHPQFEKEFEN LYFQSEVQLVESGGGLVQAGGSLRLSCAASDIFSINAMGWYRQAPGKQRE LVASITRGGDPWYADSVKGRFTISRDGAKNARNTVYLQMNSLKPEDTAVY YCNAMGIRGSGGDYAREAGGQGTQVTVSSSAAGGGGSGGGGSAAALKF QCGQKTLRPRFKIIGGEFTTIENQPWFAAIYRRHRGGSVTYVCGGSLISPC WVISATHCFIDYPKKEDYIVYLGRSRLNSNTQGEMKFEVENLILHKDYSADT LAHHNDIALLKIRSKEGRCAQPSRTIQTICLPSMYNDPQFGTSCEITGFGKE NSTDYLYPEQLKMTVVKLISHRECQQPHYYGSEVTTKMLCAADPQWKTDS CQGDSGGPLVCSLQGRMTLTGIVSWGRGCALKDKPGVYTRVSHFLPWIR SHTKEENGLAL |

TABLE 3-continued

Description of the sequences

| SEQ ID NO: | Seq name | Sequence |
|---|---|---|
| 13 | 12A5 | AVQLVESGGGLVQPGGSLRLSCLASGRIFSIGAMGMYRQAPGKQRELVAT ITSGGSTNYADPVKGRFTISRDGPKNTVYLQMNSLKPEDTAVYYCYANLKQ GSYGYRFNDYWGQGTQVTVSS |
| 14 | 12A5H1 | EVQLVESGGGLVQPGGSLRLSCAASGRIFSIGAMGMYRQAPGKGRELVAT ITSGGSTNYADPVKGRFTISRDGPKNTVYLQMNSLRAEDTAVYYCYANLKQ GSYGYRFNDYWGQGTQVTVSS |
| 15 | R2-mmUPA | METDTLLLWVLLLWVPGSTGDGSSAWSHPQFEKGSSAWSHPQFEKEFEN LYFQSQVQLQESGGGLVQAGGSLRLSCAASGRATSGHGHYGMGWFRQV PGKEREFVAAIRWSGKETWYKDSVKGRFTISRDNAKTTVYLQMNSLKPED TAVYYCAARPVRVDDISLPVGFDYWGQGTQVTVSSSAAGGGGSGGGGSA AAQGFQCGQKALRPRFKIVGGEFTEVENQPWFAAIYQKNKGGSPPSFKC GGSLISPCWVASAAHCFIQLPKKENYVVYLGQSKESSYNPGEMKFEVEQLIL HEYYREDSLAYHNDIALLKIRTSTGQCAQPSRSIQTICLPPRFTDAPFGSDCEI TGFGKESESDYLYPKNLKMSVVKLVSHEQCMQPHYYGSEINYKMLCAADP EWKTDSCKGDSGGPLICNIEGRPTLSGIVSWGRGCAEKNKPGVYTRVSHFL DWIQSHIGEEKGLAF |
| 16 | uPA connecting peptide | ADGKKPSSPPEELKFQCGQKTLRPRFK |
| 17 | tPA connecting peptide | STCGLRQYSQPQFR |
| 18 | Plasmin connecting peptide | PSFDCGKPQVEPKKCPGR |
| 19 | tPA calatytic domain sequence | STCGLRQYSQPQFRIKGGLFADIASHPWQAAIFAKHRRSPGERFLCGGILIS SCWILSAAHCFQERFPPHHLTVILGRTYRVVPGEEEQKFEVEKYIVHKEFDD DTYDNDIALLQLKSDSSRCAQESSVVRTVCLPPADLQLPDWTECELSGYGK HEALSPFYSERLKEAHVRLYPSSRCTSQHLLNRTVTDNMLCAGDTRSGGPQ ANLHDACQGDSGGPLVCLNDGRMTLVGIISWGLGCGQKDVPGVYTKVT NYLDWIRDNMRP |
| 20 | GPB1-1-hmUPA | METDTLLLWVLLLWVPGSTGDGSSAWSHPQFEKGSSAWSHPQFEKEFEN LYFQSEVQLVESGGGLVQPGGSLRLSCAASGFTFSSYWMYWVRQAPGKG LEWVSAINTGGGSTYYADSVKGRFTISRDNAKNTLYLQMNSLKSEDTAVYY CAKDLPNSDSLGYDYWGQGTQVTVSSSAAGGGGSGGGGSAAALKFQCG QKTLRPRFKIIGGEFTTIENQPWFAAIYRRHRGGSVTYVCGGSLISPCWVIS ATHCFIDYPKKEDYIVYLGRSRLNSNTQGEMKFEVENLILHKDYSADTLAHH NDIALLKIRSKEGRCAQPSRTIQTICLPSMYNDPQFGTSCEITGFGKENSTDY LYPEQLKMTVVKLISHRECQQPHYYGSEVTTKMLCAADPQWKTDSCQGD SGGPLVCSLQGRMTLTGIVSWGRGCALKDKPGVYTRVSHFLPWIRSHTKE ENGLAL |
| 21 | GPB1-2-hmUPA | METDTLLLWVLLLWVPGSTGDGSSAWSHPQFEKGSSAWSHPQFEKEFEN LYFQSEVQLVESGGGLVQPGGSLRLICVGSDRIFSNYSMGWFRQAPGKE RQFVSTISRHGTSTAYADSVRGRFTISRDNAENIVYLQMNSLEPEDTAVYYC AARPHTQHYVRVESYGVWGQGTQVTVSSSAAGGGGSGGGGSAAALKFQ CGQKTLRPRFKIIGGEFTTIENQPWFAAIYRRHRGGSVTYVCGGSLISPCWV ISATHCFIDYPKKEDYIVYLGRSRLNSNTQGEMKFEVENLILHKDYSADTLAH HNDIALLKIRSKEGRCAQPSRTIQTICLPSMYNDPQFGTSCEITGFGKENST DYLYPEQLKMTVVKLISHRECQQPHYYGSEVTTKMLCAADPQWKTDSCQ GDSGGPLVCSLQGRMTLTGIVSWGRGCALKDKPGVYTRVSHFLPWIRSHT KEENGLAL |
| 22 | GPB1-3-hmUPA | METDTLLLWVLLLWVPGSTGDGSSAWSHPQFEKGSSAWSHPQFEKEFEN LYFQSEVQLVESGGGLVQAGGSLRLSCAASGSINSIRAMGWYRQPPGKQR ELVATITRDGRTNYPDSVKGQFTISIDNARNTVSLQRNSLKPEDTAVYYCVA DWGEGYLTRVWGQGTQVTVSSSAAGGGGSGGGGSAAALKFQCGQKTL RPRFKIIGGEFTTIENQPWFAAIYRRHRGGSVTYVCGGSLISPCWVISATHC FIDYPKKEDYIVYLGRSRLNSNTQGEMKFEVENLILHKDYSADTLAHHNDIA LLKIRSKEGRCAQPSRTIQTICLPSMYNDPQFGTSCEITGFGKENSTDYLYPE QLKMTVVKLISHRECQQPHYYGSEVTTKMLCAADPQWKTDSCQGDSGG PLVCSLQGRMTLTGIVSWGRGCALKDKPGVYTRVSHFLPWIRSHTKEENG LAL |
| 23 | GPB1-4 hmUPA | METDTLLLWVLLLWVPGSTGDGSSAWSHPQFEKGSSAWSHPQFEKEFEN LYFQSEVQLVESGGGLVQAGGSLRLSCAASETFSIRAMGWYRQAPGKQRE LVAYITSGGSTNYADSVKGRFTISRDNDRNTVSLQMNSLKPEDTAVYYCYQ APRSGYDPVYWGQGTQVTVSSSAAGGGGSGGGGSAAALKFQCGQKTLR PRFKIIGGEFTTIENQPWFAAIYRRHRGGSVTYVCGGSLISPCWVISATHCFI DYPKKEDYIVYLGRSRLNSNTQGEMKFEVENLILHKDYSADTLAHHNDIALL KIRSKEGRCAQPSRTIQTICLPSMYNDPQFGTSCEITGFGKENSTDYLYPEQL |

TABLE 3-continued

| Description of the sequences | | |
|---|---|---|
| SEQ ID NO: | Seq name | Sequence |

| | | KMTVVKLISHRECQQPHYYGSEVTTKMLCAADPQWKTDSCQGDSGGPLV CSLQGRMTLTGIVSWGRGCALKDKPGVYTRVSHFLPWIRSHTKEENGLAL |
|---|---|---|
| 24 | GPB1-5 hmUPA | METDTLLLWVLLLWVPGSTGDGSSAWSHPQFEKGSSAWSHPQFEKEFEN LYFQSEVQLVESGGGLVQPGGSLRLSCAASEFTFSKHWMYWVRQAPGKG LEWVSGINLGGDSTYYADSVKGRFTISRDNAKNTLYLQMDSLKSEDTAVYY CAKGASSWFGDFGSWGQGTQVTVSSSAAGGGGSGGGGSAAALKFQCG QKTLRPRFKIIGGEFTTIENQPWFAAIYRRHRGGSVTYVCGGSLISPCWVIS ATHCFIDYPKKEDYIVYLGRSRLNSNTQGEMKFEVENLILHKDYSADTLAHH NDIALLKIRSKEGRCAQPSRTIQTICLPSMYNDPQFGTSCEITGFGKENSTDY LYPEQLKMTVVKLISHRECQQPHYYGSEVTTKMLCAADPQWKTDSCQGD SGGPLVCSLQGRMTLTGIVSWGRGCALKDKPGVYTRVSHFLPWIRSHTKE ENGLAL |
| 25 | GPB1-6 hmUPA | METDTLLLWVLLLWVPGSTGDGSSAWSHPQFEKGSSAWSHPQFEKEFEN LYFQSEVQLVESGGGLVQPGGSLRLSCAASGFTFSNFAMNWVRQAPGKG LEWVSFINRGGGSTGYADSVKGRFTISRDNAKNTLYLQMNSLKPEDTAVYY YCAKFSRSVPPYYGMDYWGKGTLVTVSSSAAGGGGSGGGGSAAALKFQC GQKTLRPRFKIIGGEFTTIENQPWFAAIYRRHRGGSVTYVCGGSLISPCWVI SATHCFIDYPKKEDYIVYLGRSRLNSNTQGEMKFEVENLILHKDYSADTLAH HNDIALLKIRSKEGRCAQPSRTIQTICLPSMYNDPQFGTSCEITGFGKENST DYLYPEQLKMTVVKLISHRECQQPHYYGSEVITKMLCAADPQWKTDSCQ GDSGGPLVCSLQGRMTLTGIVSWGRGCALKDKPGVYTRVSHFLPWIRSHT KEENGLAL |
| 26 | GPB1-7 hmUPA | METDTLLLWVLLLWVPGSTGDGSSAWSHPQFEKGSSAWSHPQFEKEFEN LYFQSEVQLVESGGGLVQAGGSLRLSCAASGRVDSMAWFRQAPGKEREF VATITWSDSKIYYADSVKGRFTISGERAKNTMYLQMNTLRPEDTAVYYCAA AHRPYRSGYYYMQSRYDYWGQGTQVTVSSSAAGGGGSGGGGSAAALKF QCGQKTLRPRFKIIGGEFTTIENQPWFAAIYRRHRGGSVTYVCGGSLISPC WVISATHCFIDYPKKEDYIVYLGRSRLNSNTQGEMKFEVENLILHKDYSADT LAHHNDIALLKIRSKEGRCAQPSRTIQTICLPSMYNDPQFGTSCEITGFGKE NSTDYLYPEQLKMTVVKLISHRECQQPHYYGSEVTTKMLCAADPQWKTDS CQGDSGGPLVCSLQGRMTLTGIVSWGRGCALKDKPGVYTRVSHFLPWIR SHTKEENGLAL |
| 27 | GPB1-8 hmUPA | METDTLLLWVLLLWVPGSTGDGSSAWSHPQFEKGSSAWSHPQFEKEFEN LYFQSEVQLVESGGGLVQAGGSLRLSCAAPSMFSINAMGWYRQAPGRQR ELVATITSGDSTYYADSVKGRFTISRDNAKYTKNTVYLQMNSLKPEDTAVYY CNAAHIRGSGGDYAREAWGQGTQVTVSSSAAGGGGSGGGGSAAALKFQ CGQKTLRPRFKIIGGEFTTIENQPWFAAIYRRHRGGSVTYVCGGSLISPCWV ISATHCFIDYPKKEDYIVYLGRSRLNSNTQGEMKFEVENLILHKDYSADTLAH HNDIALLKIRSKEGRCAQPSRTIQTICLPSMYNDPQFGTSCEITGFGKENST DYLYPEQLKMTVVKLISHRECQQPHYYGSEVTTKMLCAADPQWKTDSCQ GDSGGPLVCSLQGRMTLTGIVSWGRGCALKDKPGVYTRVSHFLPWIRSHT KEENGLAL |
| 28 | GPB1-9 hmUPA | METDTLLLWVLLLWVPGSTGDGSSAWSHPQFEKGSSAWSHPQFEKEFEN LYFQSEVQLVESGGGLVQAGGSLRLSCAASGPTVSNYYMGWFRQAPGKE RDFVAGISRSGVEKYYADSVKGRFTISRDNALNTVYLQMNSLKPEDTAAYY CAARERVGITFAHSTVDYWGKGTLVTVSSSAAGGGGSGGGGSAAALKFQ CGQKTLRPRFKIIGGEFTTIENQPWFAAIYRRHRGGSVTYVCGGSLISPCWV ISATHCFIDYPKKEDYIVYLGRSRLNSNTQGEMKFEVENLILHKDYSADTLAH HNDIALLKIRSKEGRCAQPSRTIQTICLPSMYNDPQFGTSCEITGFGKENST DYLYPEQLKMTVVKLISHRECQQPHYYGSEVTTKMLCAADPQWKTDSCQ GDSGGPLVCSLQGRMTLTGIVSWGRGCALKDKPGVYTRVSHFLPWIRSHT KEENGLAL |
| 29 | GPB1-10 hmUPA | METDTLLLWVLLLWVPGSTGDGSSAWSHPQFEKGSSAWSHPQFEKEFEN LYFQSEVQLVESGGGLVQPGGSLRLSCAASGFTFSKYGMSWVRQAPGKGL EWVSIIDSGGGAIGYADAVKGRFTISRDNVKNTLYLQMNSLKPEDTAVYHC VFGDYKGQGTQVTVSSSAAGGGGSGGGGSAAALKFQCGQKTLRPRFKIIG GEFTTIENQPWFAAIYRRHRGGSVTYVCGGSLISPCWVISATHCFIDYPKKE DYIVYLGRSRLNSNTQGEMKFEVENLILHKDYSADTLAHHNDIALLKIRSKE GRCAQPSRTIQTICLPSMYNDPQFGTSCEITGFGKENSTDYLYPEQLKMTV VKLISHRECQQPHYYGSEVTTKMLCAADPQWKTDSCQGDSGGPLVCSLQ GRMTLTGIVSWGRGCALKDKPGVYTRVSHFLPWIRSHTKEENGLAL |
| 30 | GPB1-11 hmUPA | METDTLLLWVLLLWVPGSTGDGSSAWSHPQFEKGSSAWSHPQFEKEFEN LYFQSEVQLVESGGGLVQPGGSLRLSCAASGFTFSSSAMTWVRQAPGKGL EWVSAINSGGSGTRYADSVKGRFTISRDNAKNTLYLQMNSLKPEDTAVYY CAKRRDGQNWYPGISYESMYRGQGTQVTVSSSAAGGGGSGGGGSAAAL KFQCGQKTLRPRFKIIGGEFTTIENQPWFAAIYRRHRGGSVTYVCGGSLISP CWVISATHCFIDYPKKEDYIVYLGRSRLNSNTQGEMKFEVENLILHKDYSAD TLAHHNDIALLKIRSKEGRCAQPSRTIQTICLPSMYNDPQFGTSCEITGFGKE NSTDYLYPEQLKMTVVKLISHRECQQPHYYGSEVTTKMLCAADPQWKTDS |

TABLE 3-continued

Description of the sequences

| SEQ ID NO: | Seq name | Sequence |
|---|---|---|

CQGDSGGPLVCSLQGRMTLTGIVSWGRGCALKDKPGVYTRVSHFLPWIR
SHTKEENGLAL

31   GPB1-12 hmUPA   METDTLLLWVLLLWVPGSTGDGSSAWSHPQFEKGSSAWSHPQFEKEFEN
LYFQSEVQLVESGGGLVQAGGSLRLSCAASGRTFSSYTMAWFRQAPGKER
EFVGLISWNAKSTYVTDSVKGRFTITRENAKDMVYLQMNSLKPEDSATYYC
AANRYGSSVPGAYNYWGQGTQVTVSSSAAGGGGSGGGGSAAALKFQCG
QKTLRPRFKIIGGEFTTIENQPWFAAIYRRHRGGSVTYVCGGSLISPCWVIS
ATHCFIDYPKKEDYIVYLGRSRLNSNTQGEMKFEVENLILHKDYSADTLAHH
NDIALLKIRSKEGRCAQPSRTIQTICLPSMYNDPQFGTSCEITGFGKENSTDY
LYPEQLKMTVVKLISHRECQQPHYYGSEVITKMLCAADPQWKTDSCQGD
SGGPLVCSLQGRMTLTGIVSWGRGCALKDKPGVYTRVSHFLPWIRSHTKE
ENGLAL

32   GPB1-13 hmUPA   METDTLLLWVLLLWVPGSTGDGSSAWSHPQFEKGSSAWSHPQFEKEFEN
LYFQSEVQLVESGGGLVQPGGSLRLSCAASGFTFSSYYMSWVRQAPGKGL
EWVSAINMGGGSTYYADSVKGRFTISRDNAKNTLYLQMSGLKPEDTALYY
CVRGGSAYSVRYEYAYWGQGTQVTVSSSAAGGGGSGGGGSAAALKFQC
GQKTLRPRFKIIGGEFTTIENQPWFAAIYRRHRGGSVTYVCGGSLISPCWVI
SATHCFIDYPKKEDYIVYLGRSRLNSNTQGEMKFEVENLILHKDYSADTLAH
HNDIALLKIRSKEGRCAQPSRTIQTICLPSMYNDPQFGTSCEITGFGKENST
DYLYPEQLKMTVVKLISHRECQQPHYYGSEVTTKMLCAADPQWKTDSCQ
GDSGGPLVCSLQGRMTLTGIVSWGRGCALKDKPGVYTRVSHFLPWIRSHT
KEENGLAL

33   GPB1-14 hmUPA   METDTLLLWVLLLWVPGSTGDGSSAWSHPQFEKGSSAWSHPQFEKEFEN
LYFQSEVQLVESGGGLVQAGGSLRLSCAAAASWFSIYAMGWYRQAPGKQ
RELVAIILSDGDTDYADSVKGRFTISRDNAKNTKNTVYLQMNSLKPEDTAV
YYCNARGIRGSGGDYAREAWGQGTQVTVSSSAAGGGGSGGGGSAAALK
FQCGQKTLRPRFKIIGGEFTTIENQPWFAAIYRRHRGGSVTYVCGGSLISPC
WVISATHCFIDYPKKEDYIVYLGRSRLNSNTQGEMKFEVENLILHKDYSADT
LAHHNDIALLKIRSKEGRCAQPSRTIQTICLPSMYNDPQFGTSCEITGFGKE
NSTDYLYPEQLKMTVVKLISHRECQQPHYYGSEVTTKMLCAADPQWKTDS
CQGDSGGPLVCSLQGRMTLTGIVSWGRGCALKDKPGVYTRVSHFLPWIR
SHTKEENGLAL

34   GPB1-15 hmUPA   METDTLLLWVLLLWVPGSTGDGSSAWSHPQFEKGSSAWSHPQFEKEFEN
LYFQSEVQLVESGGGLVQAGGSLRLSCAASGSMFSINDMGWYRQAPGK
QRELVATITRGGNTYYADSVKGRFTISRDNATYTKNTVYLQMNSLKPEDTA
VYYCNARHIRGSGGDYAREAWGQGTQVTVSSSAAGGGGSGGGGSAAAL
KFQCGQKTLRPRFKIIGGEFTTIENQPWFAAIYRRHRGGSVTYVCGGSLISP
CWVISATHCFIDYPKKEDYIVYLGRSRLNSNTQGEMKFEVENLILHKDYSAD
TLAHHNDIALLKIRSKEGRCAQPSRTIQTICLPSMYNDPQFGTSCEITGFGKE
NSTDYLYPEQLKMTVVKLISHRECQQPHYYGSEVTTKMLCAADPQWKTDS
CQGDSGGPLVCSLQGRMTLTGIVSWGRGCALKDKPGVYTRVSHFLPWIR
SHTKEENGLAL

35   GPB1-16 hmUPA   METDTLLLWVLLLWVPGSTGDGSSAWSHPQFEKGSSAWSHPQFEKEFEN
LYFQSEVQLVESGGGLVQAGGSLRLSCAASRRTFSNYVMGWFRQAPGKE
RESVTAIGRSGTILYADSMKGRITISRDNAKNTVYLQMNSLTPDDTAVYYC
AASSGSMQQFWRMEYDYEGQGTQVTVSSSAAGGGGSGGGGSAAALKF
QCGQKTLRPRFKIIGGEFTTIENQPWFAAIYRRHRGGSVTYVCGGSLISPC
WVISATHCFIDYPKKEDYIVYLGRSRLNSNTQGEMKFEVENLILHKDYSADT
LAHHNDIALLKIRSKEGRCAQPSRTIQTICLPSMYNDPQFGTSCEITGFGKE
NSTDYLYPEQLKMTVVKLISHRECQQPHYYGSEVTTKMLCAADPQWKTDS
CQGDSGGPLVCSLQGRMTLTGIVSWGRGCALKDKPGVYTRVSHFLPWIR
SHTKEENGLAL

36   GPB1-19 hmUPA   METDTLLLWVLLLWVPGSTGDGSSAWSHPQFEKGSSAWSHPQFEKEFEN
LYFQSEVQLVESGGGLVQAGGSLRLSCAASGRTFGSYVMGWFRQAPGKE
REFVAAIGRSGTTYYLDSVKGRFTISRDNAKNTVYLQMNSLKSEDTAVYYC
GASLKGTVLGIARYEYDVRGQGTQVTVSSSAAGGGGSGGGGSAAALKFQ
CGQKTLRPRFKIIGGEFTTIENQPWFAAIYRRHRGGSVTYVCGGSLISPCWV
ISATHCFIDYPKKEDYIVYLGRSRLNSNTQGEMKFEVENLILHKDYSADTLAH
HNDIALLKIRSKEGRCAQPSRTIQTICLPSMYNDPQFGTSCEITGFGKENST
DYLYPEQLKMTVVKLISHRECQQPHYYGSEVTTKMLCAADPQWKTDSCQ
GDSGGPLVCSLQGRMTLTGIVSWGRGCALKDKPGVYTRVSHFLPWIRSHT
KEENGLAL

37   GPB1-20 hmUPA   METDTLLLWVLLLWVPGSTGDGSSAWSHPQFEKGSSAWSHPQFEKEFEN
LYFQSEVQLVESGGGSVQAGGSLRLSCAASGRTLSSLAMGWFRQAPGKER
EFVAADRRNGGYTVVADYTDSVKGRFTIFRDNAKNTVYLQMNNLKPEDT
AVYYCAADSDRTMSLRSTDYDYWGQGTQVIVSSSAAGGGGSGGGGSAA
ALKFQCGQKTLRPRFKIIGGEFTTIENQPWFAAIYRRHRGGSVTYVCGGSLI
SPCWVISATHCFIDYPKKEDYIVYLGRSRLNSNTQGEMKFEVENLILHKDYS
ADTLAHHNDIALLKIRSKEGRCAQPSRTIQTICLPSMYNDPQFGTSCEITGF

TABLE 3-continued

| | Description of the sequences | |
|---|---|---|
| SEQ ID NO: | Seq name | Sequence |

| | | |
|---|---|---|
| | | GKENSTDYLYPEQLKMTVVKLISHRECQQPHYYGSEVTTKMLCAADPQW<br>KTDSCQGDSGGPLVCSLQGRMTLTGIVSWGRGCALKDKPGVYTRVSHFLP<br>WIRSHTKEENGLAL |
| 38 | Flexible linker | KESGSVSSEQLAQFRSLD |
| 39 | Flexible linker | EGKSSGSGSESKST |
| 40 | Caplacizumab<br>double stranded<br>DNA fragment | GGATCCGAAGTCCAGCTTGTAGAATCAGGAGGAGGCCTTGTCCAGCCA<br>GGTGGTAGCCTTCGTCTGTCGTGTGCTGCTTCGGGCCGCACATTTTCGT<br>ATAACCCTATGGGTTGGTTTCGCCAAGCACCCGGCAAGGGACGCGAGT<br>TGGTGGCCGCGATTAGTCGTACGGGTGGTTCCACCTACTACCCGGATTC<br>AGTGGAAGGACGCTTTACGATTAGCCGTGATAACGCGAAGCGTATGGT<br>CTACTTACAGATGAATAGCTTGCGCGCGGAAGACACCGCGGTATACTA<br>TTGTGCTGCAGCAGGAGTCCGTGCTGAGGATGGACGCGTCCGCACGTT<br>ACCTAGTGAGTATACATTCTGGGGCCAGGGCACCCAAGTTACCGTATCC<br>AGTGCAGCAGCGGAAGTACAACTGGTCGAATCTGGAGGAGGACTTGT<br>ACAACCAGGGGGTTCCTTACGTTTGTCATGTGCGGCAAGTGGGCGCAC<br>ATTTAGTTACAACCCTATGGGCTGGTTCCGTCAAGCCCCGGGAAAAGG<br>GCGCGAACTTGTAGCCGCCATTTCGCGTACAGGGGGAAGTACCTATTA<br>CCCGGACTCAGTAGAGGGACGCTTCACGATTTCTCGTGACAACGCAAA<br>GCGCATGGTTTATCTGCAAATGAATAGTTTTACGCGCCAAGATACAGC<br>AGTTTACTATTGCGCCGCAGCTGGAGTCCGCGCCGAAGACGGCCGTGT<br>ACGCACCTTGCCTTCTGAATACACTTTTTGGGGTCAAGGAACACAGGTG<br>ACCGTGTCATCTGCGGCCGC |
| 41 | Caplacizumab in<br>pTH4.0 protein<br>sequence | MKYLLPTAAAGLLLLAAQPAMAQSGHHHHHHHDYDIPSSENLYFQGSE<br>VQLVESGGGLVQPGGSLRLSCAASGRTFSYNPMGWFRQAPGKGRELVAA<br>ISRTGGSTYYPDSVEGRFTISRDNAKRMVYLQMNSLRAEDTAVYYCAAAG<br>VRAEDGRVRTLPSEYTFWGQGTQVTVSSAAAEVQLVESGGGLVQPGGSL<br>RLSCAASGRTFSYNPMGWFRQAPGKGRELVAAISRTGGSTYYPDSVEGRF<br>TISRDNAKRMVYLQMNSLRAEDTAVYYCAAAGVRAEDGRVRTLPSEYTF<br>WGQGTQVTVSSAAAEQKLISEEDL |
| 42 | Primer Fw | TAATACGACTCACTATAGGG |
| 43 | Primer Rv | GCTAGTTATTGCTCAGCGG |
| 44 | Cablivi-hmUPA | METDTLLLWVLLLWVPGSTGDGSSAWSHPQFEKGSSAWSHPQFEKEFEN<br>LYFQSEVQLVESGGGLVQPGGSLRLSCAASGRTFSYNPMGWFRQAPGKG<br>RELVAAISRTGGSTYYPDSVEGRFTISRDNAKRMVYLQMNSLRAEDTAVYY<br>CAAAGVRAEDGRVRTLPSEYTFWGQGTQVTVSSSAAGGGGSGGGGSAA<br>ALKFQCGQKTLRPRFKIIGGEFTTIENQPWFAAIYRRHRGGSVTYVCGGSLI<br>SPCWVISATHCFIDYPKKEDYIVYLGRSRLNSNTQGEMKFEVENLILHKDYS<br>ADTLAHHNDIALLKIRSKEGRCAQPSRTIQTICLPSMYNDPQFGTSCEITGF<br>GKENSTDYLYPEQLKMTVVKLISHRECQQPHYYGSEVTTKMLCAADPQW<br>KTDSCQGDSGGPLVCSLQGRMTLTGIVSWGRGCALKDKPGVYTRVSHFLP<br>WIRSHTKEENGLAL |
| 45 | Cablivi-mmUPA | METDTLLLWVLLLWVPGSTGDGSSAWSHPQFEKGSSAWSHPQFEKEFEN<br>LYFQSEVQLVESGGGLVQPGGSLRLSCAASGRTFSYNPMGWFRQAPGKG<br>RELVAAISRTGGSTYYPDSVEGRFTISRDNAKRMVYLQMNSLRAEDTAVYY<br>CAAAGVRAEDGRVRTLPSEYTFWGQGTQVTVSSSAAGGGGSGGGGSAA<br>AQGFQCGQKALRPRFKIVGGEFTEVENQPWFAAIYQKNKGGSPPSFKCG<br>GSLISPCWVASAAHCFIQLPKKENYVVYLGQSKESSYNPGEMKFEVEQLIL |
| 46 | Cablivi | EVQLVESGGGLVQPGGSLRLSCAASGRTFSYNPMGWFRQAPGKGRELVA<br>AISRTGGSTYYPDSVEGRFTISRDNAKRMVYLQMNSLRAEDTAVYYCAAA<br>GVRAEDGRVRTLPSEYTFWGQGTQVTVSS |

SEQUENCE LISTING

Sequence total quantity: 46
SEQ ID NO: 1          moltype = AA   length = 268
FEATURE               Location/Qualifiers
REGION                1..268
                      note = hmUPA
source                1..268
                      mol_type = protein
                      organism = synthetic construct
SEQUENCE: 1

```
LKFQCGQKTL RPRFKIIGGE FTTIENQPWF AAIYRRHRGG SVTYVCGGSL ISPCWVISAT  60
HCFIDYPKKE DYIVYLGRSR LNSNTQGEMK FEVENLILHK DYSADTLAHH NDIALLKIRS  120
KEGRCAQPSR TIQTICLPSM YNDPQFGTSC EITGFGKENS TDYLYPEQLK MTVVKLISHR  180
ECQQPHYYGS EVTTKMLCAA DPQWKTDSCQ GDSGGPLVCS LQGRMTLTGI VSWGRGCALK  240
DKPGVYTRVS HFLPWIRSHT KEENGLAL                                     268

SEQ ID NO: 2               moltype = AA  length = 269
FEATURE                    Location/Qualifiers
REGION                     1..269
                           note = mmUPA
source                     1..269
                           mol_type = protein
                           organism = synthetic construct
SEQUENCE: 2
QGFQCGQKAL RPRFKIVGGE FTEVENQPWF AAIYQKNKGG SPPSFKCGGS LISPCWVASA  60
AHCFIQLPKK ENYVVYLGQS KESSYNPGEM KFEVEQLILH EYYREDSLAY HNDIALLKIR  120
TSTGQCAQPS RSIQTICLPP RFTDAPFGSD CEITGFGKES ESDYLYPKNL KMSVVKLVSH  180
EQCMQPHYYG SEINYKMLCA ADPEWKTDSC KGDSGGPLIC NIEGRPTLSG IVSWGRGCAE  240
KNKPGVYTRV SHFLDWIQSH IGEEKGLAF                                    269

SEQ ID NO: 3               moltype = AA  length = 21
FEATURE                    Location/Qualifiers
REGION                     1..21
                           note = secretion signal peptide
source                     1..21
                           mol_type = protein
                           organism = synthetic construct
SEQUENCE: 3
METDTLLLWV LLLWVPGSTG D                                            21

SEQ ID NO: 4               moltype = AA  length = 24
FEATURE                    Location/Qualifiers
REGION                     1..24
                           note = STREP
source                     1..24
                           mol_type = protein
                           organism = synthetic construct
SEQUENCE: 4
GSSAWSHPQF EKGSSAWSHP QFEK                                         24

SEQ ID NO: 5               moltype = AA  length = 9
FEATURE                    Location/Qualifiers
REGION                     1..9
                           note = TEV
source                     1..9
                           mol_type = protein
                           organism = synthetic construct
SEQUENCE: 5
EFENLYFQS                                                          9

SEQ ID NO: 6               moltype = AA  length = 16
FEATURE                    Location/Qualifiers
REGION                     1..16
                           note = linker
source                     1..16
                           mol_type = protein
                           organism = synthetic construct
SEQUENCE: 6
SAAGGGGSGG GGSAAA                                                  16

SEQ ID NO: 7               moltype = AA  length = 462
FEATURE                    Location/Qualifiers
REGION                     1..462
                           note = sVWF-hmUPA
source                     1..462
                           mol_type = protein
                           organism = synthetic construct
SEQUENCE: 7
METDTLLLWV LLLWVPGSTG DGSSAWSHPQ FEKGSSAWSH PQFEKEFENL YFQSEVQLVE  60
SGGGLVQAGG SLRLSCAASG RTFSSNAMGW FRQAPGKERE FVAAISWSGG STYYLDSVKG  120
RFTISRDNAK NTVYLQMNSL KPEDTAVYYC AGSAGLGYVG DPDAMDYWGK GTQVTVSSSA  180
AGGGGSGGGG SAAALKFQCG QKTLRPRFKI IGGEFTTIEN QPWFAAIYRR HRGGSVTYVC  240
GGSLISPCWV ISATHCFIDY PKKEDYIVYL GRSRLNSNTQ GEMKFEVENL ILHKDYSADT  300
LAHHNDIALL KIRSKEGRCA QPSRTIQTIC LPSMYNDPQF GTSCEITGFG KENSTDYLYP  360
EQLKMTVVKL ISHRECQQPH YYGSEVTTKM LCAADPQWKT DSCQGDSGGP LVCSLQGRMT  420
LTGIVSWGRG CALKDKPGVY TRVSHFLPWI RSHTKEENGL AL                     462

SEQ ID NO: 8               moltype = AA  length = 462
FEATURE                    Location/Qualifiers
```

-continued

```
REGION                  1..462
                        note = D3-hmUPA
source                  1..462
                        mol_type = protein
                        organism = synthetic construct
SEQUENCE: 8
METDTLLLWV LLLWVPGSTG DGSSAWSHPQ FEKGSSAWSH PQFEKEFENL YFQSEVQLVE      60
SGGGLVQAGG SLRLSCAASG QTLSNYVMGW FRQAPGKERE FVAVISRVGG STSYADSAKG     120
RFTISRDNAK NTVYLQMNSL KPEDTAVYYC AAAYTIAVVT AMREYDFWGQ GTQVTVSSSA     180
AGGGGSGGGG SAAALKFQCG QKTLRPRFKI IGGEFTTIEN QPWFAAIYRR HRGGSVTYVC     240
GGSLISPCWV ISATHCFIDY PKKEDYIVYL GRSRLNSNTQ GEMKFEVENL ILHKDYSADT     300
LAHHNDIALL KIRSKEGRCA QPSRTIQTIC LPSMYNDPQF GTSCEITGFG KENSTDYLYP     360
EQLKMTVVKL ISHRECQQPH YYGSEVTTKM LCAADPQWKT DSCQGDSGGP LVCSLQGRMT     420
LTGIVSWGRG CALKDKPGVY TRVSHFLPWI RSHTKEENGL AL                       462

SEQ ID NO: 9            moltype = AA  length = 466
FEATURE                 Location/Qualifiers
REGION                  1..466
                        note = R2-hmUPA
source                  1..466
                        mol_type = protein
                        organism = synthetic construct
SEQUENCE: 9
METDTLLLWV LLLWVPGSTG DGSSAWSHPQ FEKGSSAWSH PQFEKEFENL YFQSQVQLQE      60
SGGGLVQAGG SLRLSCAASG RATSGHGHYG MGWFRQVPGK EREFVAAIRW SGKETWYKDS     120
VKGRFTISRD NAKTTVYLQM NSLKPEDTAV YYCAARPVRV DDISLPVGFD YWGQGTQVTV     180
SSSAAGGGGS GGGGSAAALK FQCGQKTLRP RFKIIGGEFT TIENQPWFAA IYRRHRGGSV     240
TYVCGGSLIS PCWVISATHC FIDYPKKEDY IVYLGRSRLN SNTQGEMKFE VENLILHKDY     300
SADTLAHHND IALLKIRSKE GRCAQPSRTI QTICLPSMYN DPQFGTSCEI TGFGKENSTD     360
YLYPEQLKMT VVKLISHREC QQPHYYGSEV TTKMLCAADP QWKTDSCQGD SGGPLVCSLQ     420
GRMTLTGIVS WGRGCALKDK PGVYTRVSHF LPWIRSHTKE ENGLAL                   466

SEQ ID NO: 10           moltype = AA  length = 464
FEATURE                 Location/Qualifiers
REGION                  1..464
                        note = A11-hmUPA
source                  1..464
                        mol_type = protein
                        organism = synthetic construct
SEQUENCE: 10
METDTLLLWV LLLWVPGSTG DGSSAWSHPQ FEKGSSAWSH PQFEKEFENL YFQSAVQLVE      60
SGGRLVKAGA SLRLSCAASG RTFSSLPMAW FRQAPGKERE FVAFIGSDSS TLYTSSVRGR     120
FTISRDNGKN TVYLQMMNLK PEDTAVYYCA ARSSAFSSGI YYREGSYAYW GQGTQVTVSS     180
SAAGGGGSGG GGSAAALKFQ CGQKTLRPRF KIIGGEFTTI ENQPWFAAIY RRHRGGSVTY     240
VCGGSLISPC WVISATHCFI DYPKKEDYIV YLGRSRLNSN TQGEMKFEVE NLILHKDYSA     300
DTLAHHNDIA LLKIRSKEGR CAQPSRTIQT ICLPSMYNDP QFGTSCEITG FGKENSTDYL     360
YPEQLKMTVV KLISHRECQQ PHYYGSEVTT KMLCAADPQW KTDSCQGDSG GPLVCSLQGR     420
MTLTGIVSWG RGCALKDKPG VYTRVSHFLP WIRSHTKEEN GLAL                     464

SEQ ID NO: 11           moltype = AA  length = 463
FEATURE                 Location/Qualifiers
REGION                  1..463
                        note = A12-hmUPA
source                  1..463
                        mol_type = protein
                        organism = synthetic construct
SEQUENCE: 11
METDTLLLWV LLLWVPGSTG DGSSAWSHPQ FEKGSSAWSH PQFEKEFENL YFQSQVQLVE      60
SGGGLVQAGG SLRLSCTASG RTFSTYALGW FRQVPGKGRE FIAVIYWRDG SSLYSDSVKG     120
RFTISKDNAK NTVYLQMNSL KPEDTAVYYC ANRHDSRGTY YSSRGYDYWG QGTQVTVSSS     180
AAGGGGSGGG GSAAALKFQC GQKTLRPRFK IIGGEFTTIE NQPWFAAIYR RHRGGSVTYV     240
CGGSLISPCW VISATHCFID YPKKEDYIVY LGRSRLNSNT QGEMKFEVEN LILHKDYSAD     300
TLAHHNDIAL LKIRSKEGRC AQPSRTIQTI CLPSMYNDPQ FGTSCEITGF GKENSTDYLY     360
PEQLKMTVVK LISHRECQQP HYYGSEVTTK MLCAADPQWK TDSCQGDSGG PLVCSLQGRM     420
TLTGIVSWGR GCALKDKPGV YTRVSHFLPW IRSHTKEENG LAL                      463

SEQ ID NO: 12           moltype = AA  length = 462
FEATURE                 Location/Qualifiers
REGION                  1..462
                        note = GP1B-17 hmUPA
source                  1..462
                        mol_type = protein
                        organism = synthetic construct
SEQUENCE: 12
METDTLLLWV LLLWVPGSTG DGSSAWSHPQ FEKGSSAWSH PQFEKEFENL YFQSEVQLVE      60
SGGGLVQAGG SLRLSCAASD IFSINAMGWY RQAPGKQREL VASITRGGDP WYADSVKGRF     120
TISRDGAKNA RNTVYLQMNS LKPEDTAVYY CNAMGIRGSG GDYAREAGGQ GTQVTVSSSA     180
AGGGGSGGGG SAAALKFQCG QKTLRPRFKI IGGEFTTIEN QPWFAAIYRR HRGGSVTYVC     240
GGSLISPCWV ISATHCFIDY PKKEDYIVYL GRSRLNSNTQ GEMKFEVENL ILHKDYSADT     300
```

```
LAHHNDIALL KIRSKEGRCA QPSRTIQTIC LPSMYNDPQF GTSCEITGFG KENSTDYLYP   360
EQLKMTVVKL ISHRECQQPH YYGSEVTTKM LCAADPQWKT DSCQGDSGGP LVCSLQGRMT   420
LTGIVSWGRG CALKDKPGVY TRVSHFLPWI RSHTKEENGL AL                      462

SEQ ID NO: 13              moltype = AA   length = 122
FEATURE                    Location/Qualifiers
REGION                     1..122
                           note = 12A5
source                     1..122
                           mol_type = protein
                           organism = synthetic construct
SEQUENCE: 13
AVQLVESGGG LVQPGGSLRL SCLASGRIFS IGAMGMYRQA PGKQRELVAT ITSGGSTNYA   60
DPVKGRFTIS RDGPKNTVYL QMNSLKPEDT AVYYCYANLK QGSYGYRFND YWGQGTQVTV   120
SS                                                                 122

SEQ ID NO: 14              moltype = AA   length = 122
FEATURE                    Location/Qualifiers
REGION                     1..122
                           note = 12A5H1
source                     1..122
                           mol_type = protein
                           organism = synthetic construct
SEQUENCE: 14
EVQLVESGGG LVQPGGSLRL SCAASGRIFS IGAMGMYRQA PGKGRELVAT ITSGGSTNYA   60
DPVKGRFTIS RDGPKNTVYL QMNSLRAEDT AVYYCYANLK QGSYGYRFND YWGQGTQVTV   120
SS                                                                 122

SEQ ID NO: 15              moltype = AA   length = 467
FEATURE                    Location/Qualifiers
REGION                     1..467
                           note = R2-mmUPA
source                     1..467
                           mol_type = protein
                           organism = synthetic construct
SEQUENCE: 15
METDTLLLWV LLLWVPGSTG DGSSAWSHPQ FEKGSSAWSH PQFEKEFENL YFQSQVQLQE   60
SGGGLVQAGG SLRLSCAASG RATSGHGHYG MGWFRQVPGK EREFVAAIRW SGKETWYKDS   120
VKGRFTISRD NAKTTVYLQM NSLKPEDTAV YYCAARPVRV DDISLPVGFD YWGQGTQVTV   180
SSSAAGGGGS GGGGSAAAQG FQCGQKALRP RFKIVGGEFT EVENQPWFAA IYQKNKGGSP   240
PSFKCGGSLI SPCWVASAAH CFIQLPKKEN YVVYLGQSKE SSYNPGEMKF EVEQLILHEY   300
YREDSLAYHN DIALLKIRTS TGQCAQPSRS IQTICLPPRF TDAPFGSDCE ITGFGKESES   360
DYLYPKNLKM SVVKLVSHEQ CMQPHYYGSE INYKMLCAAD PEWKTDSCKG DSGGPLICNI   420
EGRPTLSGIV SWGRGCAEKN KPGVYTRVSH FLDWIQSHIG EEKGLAF                467

SEQ ID NO: 16              moltype = AA   length = 27
FEATURE                    Location/Qualifiers
REGION                     1..27
                           note = human uPA connecting peptide
source                     1..27
                           mol_type = protein
                           organism = synthetic construct
SEQUENCE: 16
ADGKKPSSPP EELKFQCGQK TLRPRFK                                       27

SEQ ID NO: 17              moltype = AA   length = 14
FEATURE                    Location/Qualifiers
REGION                     1..14
                           note = human tPA connecting peptide
source                     1..14
                           mol_type = protein
                           organism = synthetic construct
SEQUENCE: 17
STCGLRQYSQ PQFR                                                     14

SEQ ID NO: 18              moltype = AA   length = 18
FEATURE                    Location/Qualifiers
REGION                     1..18
                           note = human plasminogen connecting peptide
source                     1..18
                           mol_type = protein
                           organism = synthetic construct
SEQUENCE: 18
PSFDCGKPQV EPKKCPGR                                                 18

SEQ ID NO: 19              moltype = AA   length = 266
FEATURE                    Location/Qualifiers
REGION                     1..266
                           note = tPA catalytic domain
```

```
source                      1..266
                            mol_type = protein
                            organism = synthetic construct
SEQUENCE: 19
STCGLRQYSQ PQFRIKGGLF ADIASHPWQA AIFAKHRRSP GERFLCGGIL ISSCWILSAA   60
HCFQERFPPH HLTVILGRTY RVVPGEEEQK FEVEKYIVHK EFDDDTYDND IALLQLKSDS  120
SRCAQESSVV RTVCLPPADL QLPDWTECEL SGYGKHEALS PFYSERLKEA HVRLYPSSRC  180
TSQHLLNRTV TDNMLCAGDT RSGGPQANLH DACQGDSGGP LVCLNDGRMT LVGIISWGLG  240
CGQKDVPGVY TKVTNYLDWI RDNMRP                                       266

SEQ ID NO: 20               moltype = AA   length = 459
FEATURE                     Location/Qualifiers
REGION                      1..459
                            note = GPB1-1 - hmUPA
source                      1..459
                            mol_type = protein
                            organism = synthetic construct
SEQUENCE: 20
METDTLLLWV LLLWVPGSTG DGSSAWSHPQ FEKGSSAWSH PQFEKEFENL YFQSEVQLVE   60
SGGGLVQPGG SLRLSCAASG FTFSSYWMYW VRQAPGKGLE WVSAINTGGG STYYADSVKG  120
RFTISRDNAK NTLYLQMNSL KSEDTAVYYC AKDLPNSDSL GYDYWGQGTQ VTVSSSAAGG  180
GGSGGGGSAA ALKFQCGQKT LRPRFKIIGG EFTTIENQPW FAAIYRRHRG GSVTYVCGGS  240
LISPCWVISA THCFIDYPKK EDYIVYLGRS RLNSNTQGEM KFEVENLILH KDYSADTLAH  300
HNDIALLKIR SKEGRCAQPS RTIQTICLPS MYNDPQFGTS CEITGFGKEN STDYLYPEQL  360
KMTVVKLISH RECQQPHYYG SEVTTKMLCA ADPQWKTDSC QGDSGGPLVC SLQGRMTLTG  420
IVSWGRGCAL KDKPGVYTRV SHFLPWIRSH TKEENGLAL                         459

SEQ ID NO: 21               moltype = AA   length = 462
FEATURE                     Location/Qualifiers
REGION                      1..462
                            note = GPB1-2-hmUPA
source                      1..462
                            mol_type = protein
                            organism = synthetic construct
SEQUENCE: 21
METDTLLLWV LLLWVPGSTG DGSSAWSHPQ FEKGSSAWSH PQFEKEFENL YFQSEVQLVE   60
SGGGLVQPGG SLRLTCVGSD RTFSNYSMGW FRQAPGKERQ FVSTISRHGT STAYADSVRG  120
RFTISRDNAE NIVYLQMNSL EPEDTAVYYC AARPHTQHYV RVESYGVWGQ GTQVTVSSSA  180
AGGGGSGGGG SAAALKFQCG QKTLRPRFKI IGGEFTTIEN QPWFAAIYRR HRGGSVTYVC  240
GGSLISPCWV ISATHCFIDY PKKEDYIVYL GRSRLNSNTQ GEMKFEVENL ILHKDYSADT  300
LAHHNDIALL KIRSKEGRCA QPSRTIQTIC LPSMYNDPQF GTSCEITGFG KENSTDYLYP  360
EQLKMTVVKL ISHRECQQPH YYGSEVTTKM LCAADPQWKT DSCQGDSGGP LVCSLQGRMT  420
LTGIVSWGRG CALKDKPGVY TRVSHFLPWI RSHTKEENGL AL                     462

SEQ ID NO: 22               moltype = AA   length = 456
FEATURE                     Location/Qualifiers
REGION                      1..456
                            note = GPB1-3- hmUPA
source                      1..456
                            mol_type = protein
                            organism = synthetic construct
SEQUENCE: 22
METDTLLLWV LLLWVPGSTG DGSSAWSHPQ FEKGSSAWSH PQFEKEFENL YFQSEVQLVE   60
SGGGLVQAGG SLRLSCAASG SINSIRAMGW YRQPPGKQRE LVATITRDGR TNYPDSVKGQ  120
FTISIDNARN TVSLQRNSLK PEDTAVYYCV ADWGEGYLTR VWGQGTQVTV SSSAAGGGGS  180
GGGGSAAALK FQCGQKTLRP RFKIIGGEFT TIENQPWFAA IYRRHRGGSV TYVCGGSLIS  240
PCWVISATHC FIDYPKKEDY IVYLGRSRLN SNTQGEMKFE VENLILHKDY SADTLAHHND  300
IALLKIRSKE GRCAQPSRTI QTICLPSMYN DPQFGTSCEI TGFGKENSTD YLYPEQLKMT  360
VVKLISHREC QQPHYYGSEV TTKMLCAADP QWKTDSCQGD SGGPLVCSLQ GRMTLTGIVS  420
WGRGCALKDK PGVYTRVSHF LPWIRSHTKE ENGLAL                            456

SEQ ID NO: 23               moltype = AA   length = 455
FEATURE                     Location/Qualifiers
REGION                      1..455
                            note = GPB1-4 hmUPA
source                      1..455
                            mol_type = protein
                            organism = synthetic construct
SEQUENCE: 23
METDTLLLWV LLLWVPGSTG DGSSAWSHPQ FEKGSSAWSH PQFEKEFENL YFQSEVQLVE   60
SGGGLVQAGG SLRLSCAASE TFSIRAMGWY RQAPGKQREL VAYITSGGST NYADSVKGRF  120
TISRDNDRNT VSLQMNSLKP EDTAVYYCYQ APRSGYDPVY WGQGTQVTVS SSAAGGGGSG  180
GGGSAAALKF QCGQKTLRPR FKIIGGEFTT IENQPWFAAI YRRHRGGSVT YVCGGSLISP  240
CWVISATHCF IDYPKKEDYI VYLGRSRLNS NTQGEMKFEV ENLILHKDYS ADTLAHHNDI  300
ALLKIRSKEG RCAQPSRTIQ TICLPSMYND PQFGTSCEIT GFGKENSTDY LYPEQLKMTV  360
VKLISHRECQ QPHYYGSEVT TKMLCAADPQ WKTDSCQGDS GGPLVCSLQG RMTLTGIVSW  420
GRGCALKDKP GVYTRVSHFL PWIRSHTKEE NGLAL                             455

SEQ ID NO: 24               moltype = AA   length = 458
```

-continued

```
FEATURE          Location/Qualifiers
REGION           1..458
                 note = GPB1-5 hmUPA
source           1..458
                 mol_type = protein
                 organism = synthetic construct
SEQUENCE: 24
METDTLLLWV LLLWVPGSTG DGSSAWSHPQ FEKGSSAWSH PQFEKEFENL YFQSEVQLVE    60
SGGGLVQPGG SLRLSCAASE FTFSKHWMYW VRQAPGKGLE WVSGINLGGD STYYADSVKG   120
RFTISRDNAK NTLYLQMDSL KSEDTAVYYC AKGASSWFGD FGSWGQGTQV TVSSSAAGGG   180
GSGGGGGSAAA LKFQCGQKTL RPRFKIIGGE FTTIENQPWF AAIYRRHRGG SVTYVCGGSL   240
ISPCWVISAT HCFIDYPKKE DYIVYLGRSR LNSNTQGEMK FEVENLILHK DYSADTLAHH   300
NDIALLKIRS KEGRCAQPSR TIQTICLPSM YNDPQFGTSC EITGFGKENS TDYLYPEQLK   360
MTVVKLISHR ECQQPHYYGS EVTTKMLCAA DPQWKTDSCQ GDSGGPLVCS LQGRMTLTGI   420
VSWGRGCALK DKPGVYTRVS HFLPWIRSHT KEENGLAL                           458

SEQ ID NO: 25         moltype = AA   length = 460
FEATURE          Location/Qualifiers
REGION           1..460
                 note = GPB1-6 hmUPA
source           1..460
                 mol_type = protein
                 organism = synthetic construct
SEQUENCE: 25
METDTLLLWV LLLWVPGSTG DGSSAWSHPQ FEKGSSAWSH PQFEKEFENL YFQSEVQLVE    60
SGGGLVQPGG SLRLSCAASG FTFSNFAMNW VRQAPGKGLE WVSFINRGGG STGYADSVKG   120
RFTISRDNAK NTLYLQMNSL KPEDTAVYYC AKFSRSVPPY YGMDYWGKGT LVTVSSSAAG   180
GGGSGGGGSA AALKFQCGQK TLRPRFKIIG GEFTTIENQP WFAAIYRRHR GGSVTYVCGG   240
SLISPCWVIS ATHCFIDYPK KEDYIVYLGR SRLNSNTQGE MKFEVENLIL HKDYSADTLA   300
HHNDIALLKI RSKEGRCAQP SRTIQTICLP SMYNDPQFGT SCEITGFGKE NSTDYLYPEQ   360
LKMTVVKLIS HRECQQPHYY GSEVTTKMLC AADPQWKTDS CQGDSGGPLV CSLQGRMTLT   420
GIVSWGRGCA LKDKPGVYTR VSHFLPWIRS HTKEENGLAL                         460

SEQ ID NO: 26         moltype = AA   length = 462
FEATURE          Location/Qualifiers
REGION           1..462
                 note = GPB1 - 7 hmUPA
source           1..462
                 mol_type = protein
                 organism = synthetic construct
SEQUENCE: 26
METDTLLLWV LLLWVPGSTG DGSSAWSHPQ FEKGSSAWSH PQFEKEFENL YFQSEVQLVE    60
SGGGLVQAGG SLRLSCAASG RVDSMAWFRQ APGKEREFVA TITWSDSKIY YADSVKGRFT   120
ISGERAKNTM YLQMNTLRPE DTAVYYCAAA HRPYRSGYYY MQSRYDYWGQ GTQVTVSSSA   180
AGGGGSGGGG SAAALKFQCG QKTLRPRFKI IGGEFTTIEN QPWFAAIYRR HRGGSVTYVC   240
GGSLISPCWV ISATHCFIDY PKKEDYIVYL GRSRLNSNTQ GEMKFEVENL ILHKDYSADT   300
LAHHNDIALL KIRSKEGRCA QPSRTIQTIC LPSMYNDPQF GTSCEITGFG KENSTDYLYP   360
EQLKMTVVKL ISHRECQQPH YYGSEVTTKM LCAADPQWKT DSCQGDSGGP LVCSLQGRMT   420
LTGIVSWGRG CALKDKPGVY TRVSHFLPWI RSHTKEENGL AL                      462

SEQ ID NO: 27         moltype = AA   length = 462
FEATURE          Location/Qualifiers
REGION           1..462
                 note = GPB1-8 hmUPA
source           1..462
                 mol_type = protein
                 organism = synthetic construct
SEQUENCE: 27
METDTLLLWV LLLWVPGSTG DGSSAWSHPQ FEKGSSAWSH PQFEKEFENL YFQSEVQLVE    60
SGGGLVQAGG SLRLSCAAPS MFSINAMGWY RQAPGRQREL VATITSGDST YYADSVKGRF   120
TISRDNAKYT KNTVYLQMNS LKPEDTAVYY CNAAHIRGSG GDYAREAWGQ GTQVTVSSSA   180
AGGGGSGGGG SAAALKFQCG QKTLRPRFKI IGGEFTTIEN QPWFAAIYRR HRGGSVTYVC   240
GGSLISPCWV ISATHCFIDY PKKEDYIVYL GRSRLNSNTQ GEMKFEVENL ILHKDYSADT   300
LAHHNDIALL KIRSKEGRCA QPSRTIQTIC LPSMYNDPQF GTSCEITGFG KENSTDYLYP   360
EQLKMTVVKL ISHRECQQPH YYGSEVTTKM LCAADPQWKT DSCQGDSGGP LVCSLQGRMT   420
LTGIVSWGRG CALKDKPGVY TRVSHFLPWI RSHTKEENGL AL                      462

SEQ ID NO: 28         moltype = AA   length = 462
FEATURE          Location/Qualifiers
REGION           1..462
                 note = GPB1-9 hmUPA
source           1..462
                 mol_type = protein
                 organism = synthetic construct
SEQUENCE: 28
METDTLLLWV LLLWVPGSTG DGSSAWSHPQ FEKGSSAWSH PQFEKEFENL YFQSEVQLVE    60
SGGGLVQAGG SLRLSCAASG PTVSNYYMGW FRQAPGKERD FVAGISRSGV EKYYADSVKG   120
RFTISRDNAL NTVYLQMNSL KPEDTAAYYC AARERVGITF AHSTVDYWGK GTLVTVSSSA   180
AGGGGSGGGG SAAALKFQCG QKTLRPRFKI IGGEFTTIEN QPWFAAIYRR HRGGSVTYVC   240
```

```
GGSLISPCWV ISATHCFIDY PKKEDYIVYL GRSRLNSNTQ GEMKFEVENL ILHKDYSADT    300
LAHHNDIALL KIRSKEGRCA QPSRTIQTIC LPSMYNDPQF GTSCEITGFG KENSTDYLYP    360
EQLKMTVVKL ISHRECQQPH YYGSEVTTKM LCAADPQWKT DSCQGDSGGP LVCSLQGRMT    420
LTGIVSWGRG CALKDKPGVY TRVSHFLPWI RSHTKEENGL AL                      462

SEQ ID NO: 29            moltype = AA   length = 450
FEATURE                  Location/Qualifiers
REGION                   1..450
                         note = GPB1-10 hmUPA
source                   1..450
                         mol_type = protein
                         organism = synthetic construct
SEQUENCE: 29
METDTLLLWV LLLWVPGSTG DGSSAWSHPQ FEKGSSAWSH PQFEKEFENL YFQSEVQLVE    60
SGGGLVQPGG SLRLSCAASG FTFSKYGMSW VRQAPGKGLE WVSIIDSGGG AIGYADAVKG    120
RFTISRDNVK NTLYLQMNSL KPEDTAVYHC VFGDYKGQGT QVTVSSSAAG GGGSGGGGSA    180
AALKFQCGQK TLRPRFKIIG GEFTTIENQP WFAAIYRRHR GGSVTYVCGG SLISPCWVIS    240
ATHCFIDYPK KEDYIVYLGR SRLNSNTQGE MKFEVENLIL HKDYSADTLA HHNDIALLKI    300
RSKEGRCAQP SRTIQTICLP SMYNDPQFGT SCEITGFGKE NSTDYLYPEQ LKMTVVKLIS    360
HRECQQPHYY GSEVTTKMLC AADPQWKTDS CQGDSGGPLV CSLQGRMTLT GIVSWGRGCA    420
LKDKPGVYTR VSHFLPWIRS HTKEENGLAL                                     450

SEQ ID NO: 30            moltype = AA   length = 464
FEATURE                  Location/Qualifiers
REGION                   1..464
                         note = GPB1-11 hmUPA
source                   1..464
                         mol_type = protein
                         organism = synthetic construct
SEQUENCE: 30
METDTLLLWV LLLWVPGSTG DGSSAWSHPQ FEKGSSAWSH PQFEKEFENL YFQSEVQLVE    60
SGGGLVQPGG SLRLSCAASG FTFSSSAMTW VRQAPGKGLE WVSAINSGGS GTRYADSVKG    120
RFTISRDNAK NTLYLQMNSL KPEDTAVYYC AKRRDGQNWY PGISYESMYR GQGTQVTVSS    180
SAAGGGGSGG GGSAAALKFQ CGQKTLRPRF KIIGGEFTTI ENQPWFAAIY RRHRGGSVTY    240
VCGGSLISPC WVISATHCFI DYPKKEDYIV YLGRSRLNSN TQGEMKFEVE NLILHKDYSA    300
DTLAHHNDIA LLKIRSKEGR CAQPSRTIQT ICLPSMYNDP QFGTSCEITG FGKENSTDYL    360
YPEQLKMTVV KLISHRECQQ PHYYGSEVTT KMLCAADPQW KTDSCQGDSG GPLVCSLQGR    420
MTLTGIVSWG RGCALKDKPG VYTRVSHFLP WIRSHTKEEN GLAL                     464

SEQ ID NO: 31            moltype = AA   length = 460
FEATURE                  Location/Qualifiers
REGION                   1..460
                         note = GPB1-12 hmUPA
source                   1..460
                         mol_type = protein
                         organism = synthetic construct
SEQUENCE: 31
METDTLLLWV LLLWVPGSTG DGSSAWSHPQ FEKGSSAWSH PQFEKEFENL YFQSEVQLVE    60
SGGGLVQAGG SLRLSCAASG RTFSSYTMAW FRQAPGKERE FVGLISWNAK STYVTDSVKG    120
RFTITRENAK DMVYLQMNSL KPEDSATYYC AANRYGSSVP GAYNYWGQGT QVTVSSSAAG    180
GGGSGGGGSA AALKFQCGQK TLRPRFKIIG GEFTTIENQP WFAAIYRRHR GGSVTYVCGG    240
SLISPCWVIS ATHCFIDYPK KEDYIVYLGR SRLNSNTQGE MKFEVENLIL HKDYSADTLA    300
HHNDIALLKI RSKEGRCAQP SRTIQTICLP SMYNDPQFGT SCEITGFGKE NSTDYLYPEQ    360
LKMTVVKLIS HRECQQPHYY GSEVTTKMLC AADPQWKTDS CQGDSGGPLV CSLQGRMTLT    420
GIVSWGRGCA LKDKPGVYTR VSHFLPWIRS HTKEENGLAL                          460

SEQ ID NO: 32            moltype = AA   length = 460
FEATURE                  Location/Qualifiers
REGION                   1..460
                         note = GPB1-13 hmUPA
source                   1..460
                         mol_type = protein
                         organism = synthetic construct
SEQUENCE: 32
METDTLLLWV LLLWVPGSTG DGSSAWSHPQ FEKGSSAWSH PQFEKEFENL YFQSEVQLVE    60
SGGGLVQPGG SLRLSCAASG FTFSSYMSW VRQAPGKGLE WVSAINMGGG STYYADSVKG     120
RFTISRDNAK NTLYLQMSGL KPEDTALYYC VRGGSAYSVR YEYAYWGQGT QVTVSSSAAG    180
GGGSGGGGSA AALKFQCGQK TLRPRFKIIG GEFTTIENQP WFAAIYRRHR GGSVTYVCGG    240
SLISPCWVIS ATHCFIDYPK KEDYIVYLGR SRLNSNTQGE MKFEVENLIL HKDYSADTLA    300
HHNDIALLKI RSKEGRCAQP SRTIQTICLP SMYNDPQFGT SCEITGFGKE NSTDYLYPEQ    360
LKMTVVKLIS HRECQQPHYY GSEVTTKMLC AADPQWKTDS CQGDSGGPLV CSLQGRMTLT    420
GIVSWGRGCA LKDKPGVYTR VSHFLPWIRS HTKEENGLAL                          460

SEQ ID NO: 33            moltype = AA   length = 463
FEATURE                  Location/Qualifiers
REGION                   1..463
                         note = GPB1-14 hmUPA
source                   1..463
                         mol_type = protein
```

```
                              organism = synthetic construct
SEQUENCE: 33
METDTLLLWV LLLLWVPGSTG DGSSAWSHPQ FEKGSSAWSH PQFEKEFENL YFQSEVQLVE    60
SGGGLVQAGG SLRLSCAAAA SWFSIYAMGW YRQAPGKQRE LVAIILSDGD TDYADSVKGR   120
FTISRDNAKN TKNTVYLQMN SLKPEDTAVY YCNARGIRGS GGDYAREAWG QGTQVTVSSS   180
AAGGGGSGGG GSAAALKFQC GQKTLRPRFK IIGGEFTTIE NQPWFAAIYR RHRGGSVTYV   240
CGGSLISPCW VISATHCFID YPKKEDYIVY LGRSRLNSNT QGEMKFEVEN LILHKDYSAD   300
TLAHHNDIAL LKIRSKEGRC AQPSRTIQTI CLPSMYNDPQ FGTSCEITGF GKENSTDYLY   360
PEQLKMTVVK LISHRECQQP HYYGSEVTTK MLCAADPQWK TDSCQGDSGG PLVCSLQGRM   420
TLTGIVSWGR GCALKDKPGV YTRVSHFLPW IRSHTKEENG LAL                     463

SEQ ID NO: 34          moltype = AA  length = 463
FEATURE                Location/Qualifiers
REGION                 1..463
                       note = GPB1- 15 hmUPA
source                 1..463
                       mol_type = protein
                       organism = synthetic construct
SEQUENCE: 34
METDTLLLWV LLLLWVPGSTG DGSSAWSHPQ FEKGSSAWSH PQFEKEFENL YFQSEVQLVE    60
SGGGLVQAGG SLRLSCAASG SMFSINDMGW YRQAPGKQRE LVATITRGGN TYYADSVKGR   120
FTISRDNATY TKNTVYLQMN SLKPEDTAVY YCNARHIRGS GGDYAREAWG QGTQVTVSSS   180
AAGGGGSGGG GSAAALKFQC GQKTLRPRFK IIGGEFTTIE NQPWFAAIYR RHRGGSVTYV   240
CGGSLISPCW VISATHCFID YPKKEDYIVY LGRSRLNSNT QGEMKFEVEN LILHKDYSAD   300
TLAHHNDIAL LKIRSKEGRC AQPSRTIQTI CLPSMYNDPQ FGTSCEITGF GKENSTDYLY   360
PEQLKMTVVK LISHRECQQP HYYGSEVTTK MLCAADPQWK TDSCQGDSGG PLVCSLQGRM   420
TLTGIVSWGR GCALKDKPGV YTRVSHFLPW IRSHTKEENG LAL                     463

SEQ ID NO: 35          moltype = AA  length = 461
FEATURE                Location/Qualifiers
REGION                 1..461
                       note = GPB1- 16 hmUPA
source                 1..461
                       mol_type = protein
                       organism = synthetic construct
SEQUENCE: 35
METDTLLLWV LLLLWVPGSTG DGSSAWSHPQ FEKGSSAWSH PQFEKEFENL YFQSEVQLVE    60
SGGGLVQAGG SLRLSCAASR RTFSNYVMGW FRQAPGKERE SVTAIGRSGT ILYADSMKGR   120
ITISRDNAKN TVYLQMNSLT PDDTAVYYCA ASSGSMQQFW RMEYDYEGQG TQVTVSSSAA   180
GGGGSGGGGS AAALKFQCGQ KTLRPRFKII GGEFTTIENQ PWFAAIYRRH RGGSVTYVCG   240
GSLISPCWVI SATHCFIDYP KKEDYIVYLG RSRLNSNTQG EMKFEVENLI LHKDYSADTL   300
AHHNDIALLK IRSKEGRCAQ PSRTIQTICL PSMYNDPQFG TSCEITGFGK ENSTDYLYPE   360
QLKMTVVKLI SHRECQQPHY YGSEVTTKML CAADPQWKTD SCQGDSGGPL VCSLQGRMTL   420
TGIVSWGRGC ALKDKPGVYT RVSHFLPWIR SHTKEENGLA L                       461

SEQ ID NO: 36          moltype = AA  length = 462
FEATURE                Location/Qualifiers
REGION                 1..462
                       note = GPB1- 19 hmUPA
source                 1..462
                       mol_type = protein
                       organism = synthetic construct
SEQUENCE: 36
METDTLLLWV LLLLWVPGSTG DGSSAWSHPQ FEKGSSAWSH PQFEKEFENL YFQSEVQLVE    60
SGGGLVQAGG SLRLSCAASG RTFGSYVMGW FRQAPGKERE FVAAIGRSGT TYYLDSVKGR   120
FTISRDNAKN TVYLQMNSLK SEDTAVYYCG ASLKGTVLGI ARYEYDVRGQ GTQVTVSSSA   180
AGGGGSGGGG SAAALKFQCG QKTLRPRFKI IGGEFTTIEN QPWFAAIYRR HRGGSVTYVC   240
GGSLISPCWV ISATHCFIDY PKKEDYIVYL GRSRLNSNTQ GEMKFEVENL ILHKDYSADT   300
LAHHNDIALL KIRSKEGRCA QPSRTIQTIC LPSMYNDPQF GTSCEITGFG KENSTDYLYP   360
EQLKMTVVKL ISHRECQQPH YYGSEVTTKM LCAADPQWKT DSCQGDSGGP LVCSLQGRMT   420
LTGIVSWGRG CALKDKPGVY TRVSHFLPWI RSHTKEENGL AL                      462

SEQ ID NO: 37          moltype = AA  length = 465
FEATURE                Location/Qualifiers
REGION                 1..465
                       note = GPB1- 20 hmUPA
source                 1..465
                       mol_type = protein
                       organism = synthetic construct
SEQUENCE: 37
METDTLLLWV LLLLWVPGSTG DGSSAWSHPQ FEKGSSAWSH PQFEKEFENL YFQSEVQLVE    60
SGGGSVQAGG SLRLSCAASG RTLSSSLAMGW FRQAPGKERE FVAADRRNGG YTVVADYTDS   120
VKGRFTIFRD NAKNTVYLQM NNLKPEDTAV YYCAADSDRT MSLRSTDYDY WGQGTQVTVS   180
SSAAGGGGSG GGGSAAALKF QCGQKTLRPR FKIIGGEFTT IENQPWFAAI YRRHRGGSVT   240
YVCGGSLISP CWVISATHCF IDYPKKEDYI VYLGRSRLNS NTQGEMKFEV ENLILHKDYS   300
ADTLAHHNDI ALLKIRSKEG RCAQPSRTIQ TICLPSMYND PQFGTSCEIT GFGKENSTDY   360
LYPEQLKMTV VKLISHRECQ QPHYYGSEVT TKMLCAADPQ WKTDSCQGDS GGPLVCSLQG   420
RMTLTGIVSW GRGCALKDKP GVYTRVSHFL PWIRSHTKEE NGLAL                   465
```

-continued

```
SEQ ID NO: 38            moltype = AA   length = 18
FEATURE                  Location/Qualifiers
REGION                   1..18
                         note = flexible linker
source                   1..18
                         mol_type = protein
                         organism = synthetic construct
SEQUENCE: 38
KESGSVSSEQ LAQFRSLD                                                   18

SEQ ID NO: 39            moltype = AA   length = 14
FEATURE                  Location/Qualifiers
REGION                   1..14
                         note = flexible linker
source                   1..14
                         mol_type = protein
                         organism = synthetic construct
SEQUENCE: 39
EGKSSGSGSE SKST                                                       14

SEQ ID NO: 40            moltype = DNA   length = 791
FEATURE                  Location/Qualifiers
misc_feature             1..791
                         note = dsDNA
source                   1..791
                         mol_type = other DNA
                         organism = synthetic construct
SEQUENCE: 40
ggatccgaag tccagcttgt agaatcagga ggaggccttg tccagccagg tggtagcctt    60
cgtctgtcgt gtgctgcttc gggccgcaca ttttcgtata accctatggg ttggtttcgc   120
caagcacccg gcaagggacg cgagttggtg gccgcgatta gtcgtacggg tggttccacc   180
tactacccgg attcagtgga aggacgcttt acgattagcc gtgataacgc gaagcgtatg   240
gtctacttac agatgaatag cttgcgcgcg aagacaccg cggtatacta ttgtgctgca    300
gcaggagtcc gtgctgagga tggacgcgtc cgcacgttac ctagtgagta tacattctgg   360
ggccagggca cccaagttac cgtatccagt gcagcagcgg aagtacaact ggtcgaatct   420
ggaggaggac ttgtacaacc aggggggttcc ttacgtttgt catgtgcggc aagtgggcgc   480
acatttagtt acaaccctat gggctggttc cgtcaagccc cgggaaaagg cgcgcgaactt   540
gtagccgcca tttcgcgtac aggggggaagt acctattacc cggactcagt agagggacgc   600
ttcacgattt ctcgtgacaa cgcaaagcgc atggtttatc tgcaaatgaa tagtttacgc   660
gccgaagata cagcagttta ctattgcgcc gcagctggag tccgcgccga agacggccgt   720
gtacgcacct tgccttctga atacactttt tggggtcaag gaacacaggt gaccgtgtca   780
tctgcggccg c                                                        791

SEQ ID NO: 41            moltype = AA   length = 320
FEATURE                  Location/Qualifiers
REGION                   1..320
                         note = Caplacizumab in pTH4.0 protein sequence
source                   1..320
                         mol_type = protein
                         organism = synthetic construct
SEQUENCE: 41
MKYLLPTAAA GLLLLAAQPA MAQSGHHHHH HHHDYDIPSS ENLYFQGSEV QLVESGGGLV    60
QPGGSLRLSC AASGRTFSYN PMGWFRQAPG KGRELVAAIS RTGGSTYYPD SVEGRFTISR   120
DNAKRMVYLQ MNSLRAEDTA VYYCAAAGVR AEDGRVRTLP SEYTFWGQGT QVTVSSAAAE   180
VQLVESGGGL VQPGGSLRLS CAASGRTFSY NPMGWFRQAP GKGRELVAAI SRTGGSTYYP   240
DSVEGRFTIS RDNAKRMVYL QMNSLRAEDT AVYYCAAAGV RAEDGRVRTL PSEYTFWGQG   300
TQVTVSSAAA EQKLISEEDL                                               320

SEQ ID NO: 42            moltype = DNA   length = 20
FEATURE                  Location/Qualifiers
misc_feature             1..20
                         note = primer
source                   1..20
                         mol_type = other DNA
                         organism = synthetic construct
SEQUENCE: 42
taatacgact cactataggg                                                20

SEQ ID NO: 43            moltype = DNA   length = 19
FEATURE                  Location/Qualifiers
misc_feature             1..19
                         note = primer Rv
source                   1..19
                         mol_type = other DNA
                         organism = synthetic construct
SEQUENCE: 43
gctagttatt gctcagcgg                                                 19

SEQ ID NO: 44            moltype = AA   length = 466
```

-continued

```
FEATURE              Location/Qualifiers
REGION               1..466
                     note = Cablivi-hmUPA
source               1..466
                     mol_type = protein
                     organism = synthetic construct
SEQUENCE: 44
METDTLLLWV LLLWVPGSTG DGSSAWSHPQ FEKGSSAWSH PQFEKEFENL YFQSEVQLVE   60
SGGGLVQPGG SLRLSCAASG RTFSYNPMGW FRQAPGKGRE LVAAISRTGG STYYPDSVEG  120
RFTISRDNAK RMVYLQMNSL RAEDTAVYYC AAAGVRAEDG RVRTLPSEYT FWGQGTQVTV  180
SSSAAGGGGS GGGGSAAALK FQCGQKTLRP RFKIIGGEFT TIENQPWFAA IYRRHRGGSV  240
TYVCGGSLIS PCWVISATHC FIDYPKKEDY IVYLGRSRLN SNTQGEMKFE VENLILHKDY  300
SADTLAHHND IALLKIRSKE GRCAQPSRTI QTICLPSMYN DPQFGTSCEI TGFGKENSTD  360
YLYPEQLKMT VVKLISHREC QQPHYYGSEV TTKMLCAADP QWKTDSCQGD SGGPLVCSLQ  420
GRMTLTGIVS WGRGCALKDK PGVYTRVSHF LPWIRSHTKE ENGLAL              466

SEQ ID NO: 45        moltype = AA   length = 297
FEATURE              Location/Qualifiers
REGION               1..297
                     note = Cablivi-mmUPA
source               1..297
                     mol_type = protein
                     organism = synthetic construct
SEQUENCE: 45
METDTLLLWV LLLWVPGSTG DGSSAWSHPQ FEKGSSAWSH PQFEKEFENL YFQSEVQLVE   60
SGGGLVQPGG SLRLSCAASG RTFSYNPMGW FRQAPGKGRE LVAAISRTGG STYYPDSVEG  120
RFTISRDNAK RMVYLQMNSL RAEDTAVYYC AAAGVRAEDG RVRTLPSEYT FWGQGTQVTV  180
SSSAAGGGGS GGGGSAAAQG FQCGQKALRP RFKIVGGEFT EVENQPWFAA IYQKNKGGSP  240
PSFKCGGSLI SPCWVASAAH CFIQLPKKEN YVVYLGQSKE SSYNPGEMKF EVEQLIL     297

SEQ ID NO: 46        moltype = AA   length = 128
FEATURE              Location/Qualifiers
REGION               1..128
                     note = Cablivi VHH
source               1..128
                     mol_type = protein
                     organism = synthetic construct
SEQUENCE: 46
EVQLVESGGG LVQPGGSLRL SCAASGRTFS YNPMGWFRQA PGKGRELVAA ISRTGGSTYY   60
PDSVEGRFTI SRDNAKRMVY LQMNSLRAED TAVYYCAAAG VRAEDGRVRT LPSEYTFWGQ  120
GTQVTVSS                                                           128
```

The invention claimed is:

1. A fusion protein comprising a plasminogen activator and a targeting agent for targeting the plasminogen activator to a site of a thrombus comprising Von Willebrand factor (VWF), wherein the targeting agent is a heavy chain antibody (VHH) that comprises an amino acid sequence at least 90% identical to amino acids 55-178 of SEQ ID NO:7, and wherein the plasminogen activator comprises the protease domain of urokinase plasminogen activator.

2. The fusion protein of claim 1, wherein the fusion protein comprises from the N-terminus to the C-terminus (a) the targeting agent, (b) a linker, and (c) the plasminogen activator.

3. A composition comprising the fusion protein according to claim 1 and a pharmaceutically acceptable excipient.

* * * * *